(12) United States Patent
Ferguson et al.

(10) Patent No.: US 7,893,221 B2
(45) Date of Patent: Feb. 22, 2011

(54) PROTEIN FOLDING

(75) Inventors: Mark William James Ferguson, Manchester (GB); Phillip Mellors, Manchester (GB); Hugh Gerard Laverty, Manchester (GB); Nick Occleston, Manchester (GB); Sharon O'Kane, Manchester (GB); Simon Higginbottom, Manchester (GB)

(73) Assignee: Renovo Limited, Manchester (GB)

( * ) Notice: Subject to any disclaimer, the term of this patent is extended or adjusted under 35 U.S.C. 154(b) by 0 days.

(21) Appl. No.: 12/282,456

(22) PCT Filed: Mar. 9, 2007

(86) PCT No.: PCT/GB2007/000814

§ 371 (c)(1),
(2), (4) Date: Sep. 10, 2008

(87) PCT Pub. No.: WO2007/104934

PCT Pub. Date: Sep. 20, 2007

(65) Prior Publication Data

US 2009/0181430 A1 Jul. 16, 2009

(30) Foreign Application Priority Data

Mar. 11, 2006 (GB) ................... 0604964.7

(51) Int. Cl.
*C08H 1/00* (2006.01)
(52) U.S. Cl. ...................... 530/402; 530/350
(58) Field of Classification Search ............... None
See application file for complete search history.

(56) References Cited

U.S. PATENT DOCUMENTS

| | | | |
|---|---|---|---|
| 4,051,848 A | 10/1977 | Levine | |
| 5,135,915 A | 8/1992 | Czarniecki et al. | |
| 5,411,940 A | 5/1995 | Nixon et al. | |
| 5,650,494 A | 7/1997 | Cerletti et al. | |
| 5,922,846 A | 7/1999 | Cerletti et al. | |
| 5,958,411 A | 9/1999 | Logan et al. | |
| 6,054,122 A | 4/2000 | MacPhee et al. | |
| 6,057,430 A | 5/2000 | Cerletti | |
| 6,132,759 A | 10/2000 | Schacht et al. | |
| 6,331,298 B1 | 12/2001 | Ferguson et al. | |
| 6,559,123 B1 | 5/2003 | Iwata et al. | |
| 7,341,994 B2 | 3/2008 | Ishikawa et al. | |
| 7,691,816 B2 | 4/2010 | Ferguson et al. | |
| 2004/0078851 A1 | 4/2004 | Huang et al. | |

FOREIGN PATENT DOCUMENTS

| | | |
|---|---|---|
| EP | 0200341 | 11/1986 |
| EP | 0 433 225 | 6/1991 |
| EP | 0 943 690 | 9/1999 |
| EP | 1557468 | 7/2005 |
| WO | WO90/03812 | 4/1990 |
| WO | WO-91/05565 | 5/1991 |
| WO | WO93/19769 | 10/1993 |
| WO | WO-95/16034 | 6/1995 |
| WO | WO96/03432 | 2/1996 |
| WO | WO96/32131 | 10/1996 |
| WO | WO-97/05166 | 2/1997 |
| WO | WO-99/18196 | 4/1999 |
| WO | WO-00/20607 | 4/2000 |
| WO | WO00/20612 | 4/2000 |
| WO | WO00/54797 | 9/2000 |
| WO | WO00/56879 | 9/2000 |
| WO | WO01/75132 | 10/2001 |
| WO | WO-01/92298 | 12/2001 |
| WO | WO-02/12336 | 2/2002 |
| WO | WO02/076494 | 10/2002 |
| WO | WO02/099067 | 12/2002 |
| WO | WO-2006/023782 | 3/2006 |
| WO | WO2006/118617 | 11/2006 |
| WO | WO-2007/007098 | 1/2007 |
| WO | WO-2007/104945 | 9/2007 |
| WO | WO-2007/104946 | 9/2007 |
| WO | WO-2008/032035 | 3/2008 |

OTHER PUBLICATIONS

Ejima et al. "A novel revers screening to identify refolding additives for activin-A". Protein Expression and Purification, in printed formate, (2006) 47, pp. 45-51; and on line Sep. 20, 2005.*
International Search Report for PCT/GB2007/00814, mailed Nov. 7, 2007.
International Search Report for PCT/GB2007/00833, mailed Mar. 14, 2008.
International Search Report for PCT/GB2007/00834, mailed Apr. 3, 2008.
O'Kane et al. "Transforming Growth Factor βs and Wound Healing" Int. J. Biochem. Cell Biol. vol. 29, No. 1, pp. 63-78 (1997).
Schmid et al. "TGF-βs and TGF-β Type II Receptor in Human Epidermis: Differential Expression in Acute and Chronic Skin Wounds" J. of Pathology, vol. 171, pp. 191-197 (993).
Vallejo et al. "Optimized procedure for renaturation of recombinant human bone morphogenetic protein-2 at high protein concentration," Biotechnology and Bioengineering, Interscience Publishers, London, GB, vol. 85, No. 6., pp. 601-609, (2004).

(Continued)

*Primary Examiner*—Nashaat T Nashed
(74) *Attorney, Agent, or Firm*—McDermott Will & Emery LLP

(57) ABSTRACT

The present invention concerns a method for folding a Transforming Growth Factor Beta, or a functional analogue thereof, into a dimeric, biologically active form. The method involves adding solubilized, unfolded monomeric growth factor to a solution containing 2-(cyclohexylamino)-ethanesulfonic acid (CHES) or a functional analogue thereof and a low molecular weight sulfhydryl/disulfide redox system. The solution is then incubated under conditions suitable for generating dimeric biologically active Transforming Growth Factor Beta.

1 Claim, 42 Drawing Sheets

OTHER PUBLICATIONS

Figure 1:
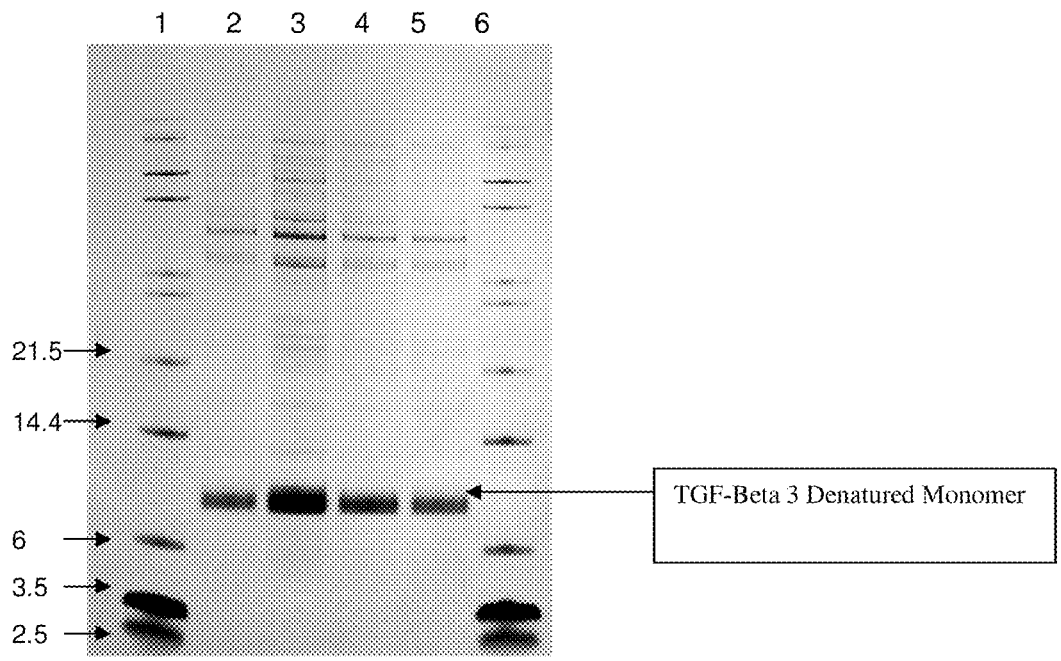

Vallejo et al. "Renaturation and purification of bone morphogenetic protein-2 produced as inclusion bodies in high-cell density cultures of recombinant *Escherichia coli*," J. of Biotech., Elsevier Science Publishes B.V., Amsterdam, NL vol. 94, No. 2., pp. 185-194, (2002).

U.S. Appl. No. 12/282,472—Non-Final Office Action dated Sep. 10, 2008, including Form PTO-892 (documents cited therein included by reference).

Bowie et al., "Deciphering the Message in Protein Sequences: Tolerance to Amino Acid Substitutions," *Science*, vol. 247, No. 4948, pp. 1306-1310 (1990).

Brannon, "Skin Anatomy," dermatology.about.com/cs/skinanatomy/a/anatomy.htm, downloaded Aug. 16, 2009.

Hao et al., TGF-β3: "A promising growth factor in engineered organogenesis," *Expert Opin. Boil. Ther.*, vol. 8, No. 10, pp. 1485-1493 (2008).

Hirshberg, TGF-β in the Treatment of Pressure Ulcers: A Preliminary Report, *Advances in Skin & Wound Care*, vol. 14, No. 2, pp. 91-95, www.woundcarenet.com (Mar./Apr. 2001).

International Search Report for WO2007/007098 (PCT/GB2006/002577) dated Mar. 3, 2007 (4 pages).

International Search Report for WO2008/032035 (PCT/GB2007/003416) dated Dec. 18, 2007 (6 pages).

Martin, "Wound Healing—Aiming for Perfect Skin Regeneration," *Science*, vol. 276, pp. 75-81 (1997).

Ngo et al., "Computational Complexity, Protein Structure Prediction, and the Levinthal Paradox," *The Protein Folding Problem and Tertiary Structure Prediction*, Merz et al, eds, Birkhauser, Boston, pp. 433-506 (1994).

Schmid et al., "TGF-βs and TGF-β Type II Receptor in Human Epidermis: Differential Expression in Acute and Chronic Skin Wounds," *Journal of Pathology*, vol. 171, pp. 191-197 (1993).

Shah et al., "Neutralisation of TGF-$\beta_1$ and TGF-$\beta_2$ or exogenous addition of TGF-$\beta_3$ to cutaneous rat wounds reduces scarring," *Journal of Cell Science*, vol. 108, pp. 985-1002 (1995).

Singer et al., "Cutaneous Wound Healing," *The New England Journal of Medicine*, vol. 341, No. 10, pp. 738-746 (1999).

Tyrone et al., "Transforming Growth Factor $\beta_3$ Promotes Fascial Wound Healing in a New Animal Model," *Arch. Surg.*, vol. 135, pp. 1154-1159, www.archsurg.com, (Oct. 2000).

U.S. Appl. No. 11/995,380: File History of all prosecution documents to date, including Bibliographic Data Page and Image File Wrapper Pages from PAIR as downloaded on Aug. 3, 2010.

U.S. Appl. No. 12/282,463: File History of all prosecution documents to date, including Bibliographic Data Page and Image File Wrapper Pages from PAIR as downloaded on Aug. 3, 2010.

U.S. Appl. No. 12/282,472: Non-Final Office Action dated Jan. 29, 2010 (8 pages).

U.S. Appl. No. 12/282,472: Non-Final Office Action dated Jun. 18, 2010 (14 pages).

U.S. Appl. No. 12/440,688: File History of all prosecution documents to date, including Bibliographic Data Page and Image File Wrapper Pages from PAIR as downloaded on Aug. 3, 2010.

Vooijs et al., "Transforming growth factor-$\beta_3$-loaded microtextured membranes for skini regeneration in dermal wounds," *Journal of biomedical Materials Research*, vol. 70, No. 3, pp. 402-411 (2004).

Wang et al., "A Single Amino Acid Determines Lysophospholipid Specificity of the $S1P_1$ (EDG1) and $LPA_1$ (EDG2) Phospholipid Growth Factor Receptors," *The Journal of Biological Chemistry*, vol. 276, No. 52, pp. 49213-49220 (2001).

Wells, "Additivity of Mutational Effects in Proteins," *Biochemistry*, vol. 29, No. 37, pp. 8509-8517 (1990).

* cited by examiner

| Lane | Sample |
|---|---|
| 1 | Mark 12 Standard |
| 2 | Clone 1 3hr Post-Induction (3μL) |
| 3 | Clone 2 3hr Post-Induction (3μL) |
| 4 | Clone 3 3hr Post-Induction (3μL) |
| 5 | Clone 4 3hr Post-Induction (3μL) |
| 6 | Mark 12 standard |

FIG. 3
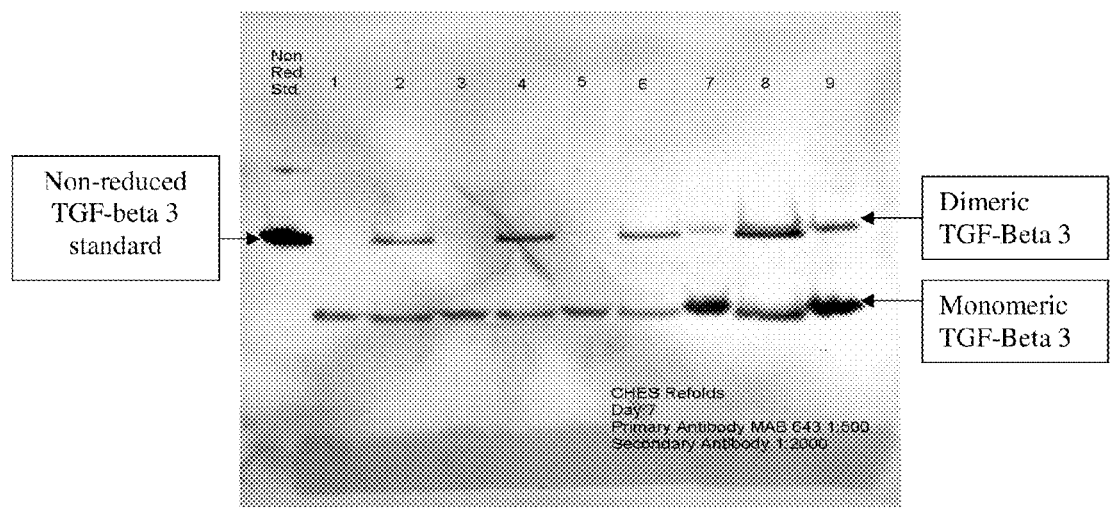
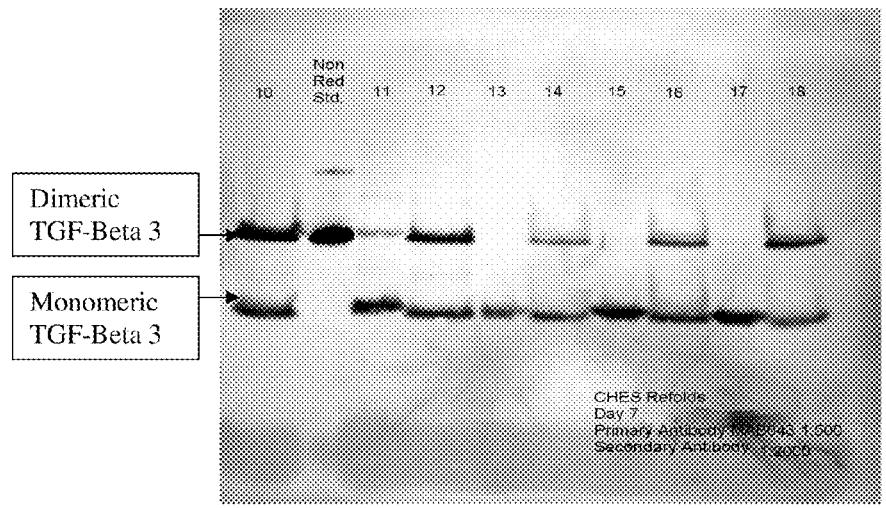

| Lane | Sample |
|---|---|
| 1 | Day 0 Re-fold |
| 2 | Day 1 re-fold |
| 3 | Day 2 re-fold |
| 4 | Day 3 re-fold |
| 5 | TGF-Beta 3 Standard |

| Lane | Sample |
|---|---|
| 1 | Day 1 re-fold |
| 2 | Day 2 re-fold |
| 3 | Day 3 re-fold |
| 4 | Day 4 re-fold |
| 5 | Day 7 re-fold |

FIG. 7
(A)
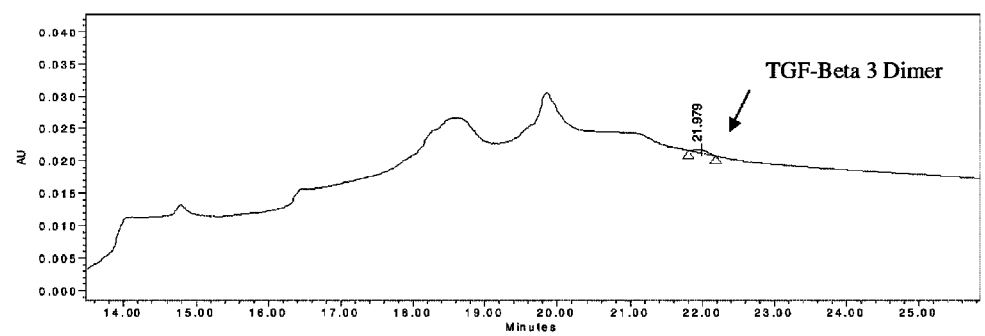
(B)
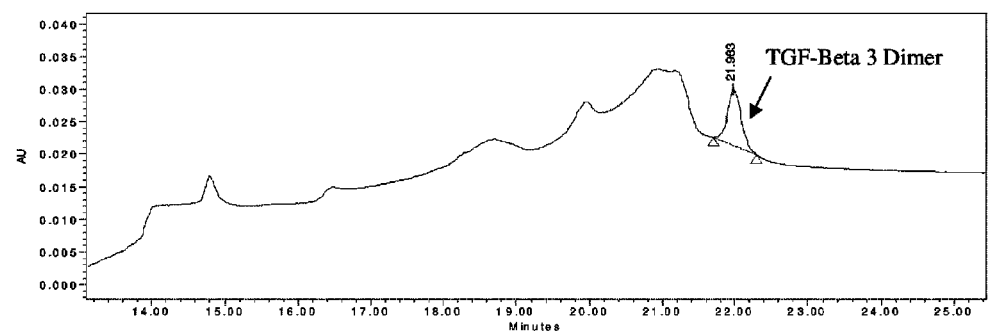
(C)
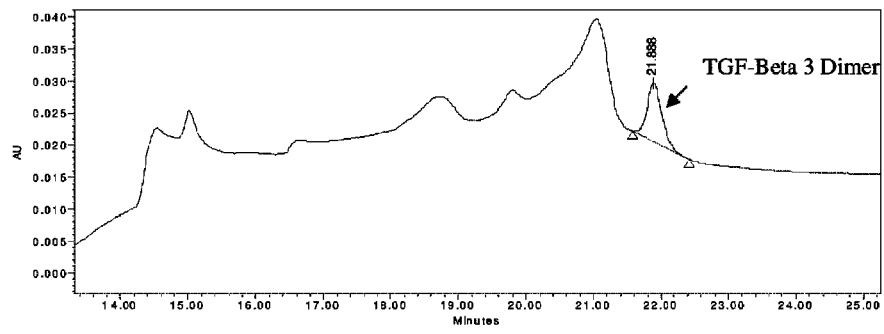

FIG 15
(A)
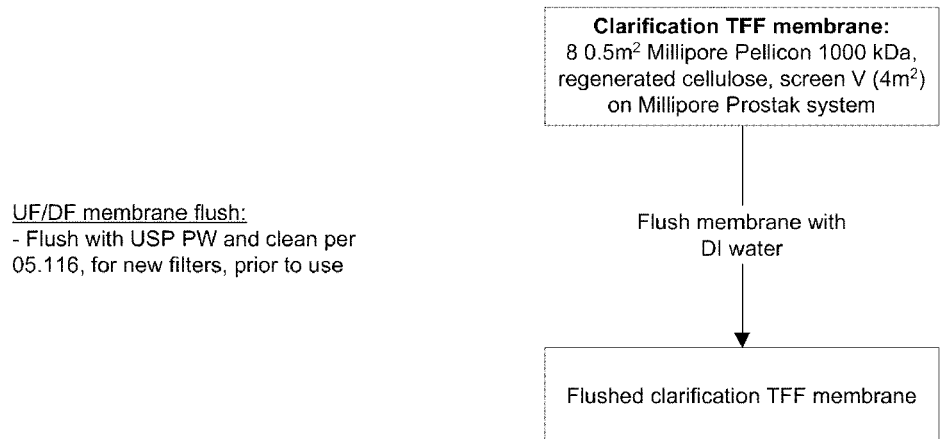
(B)
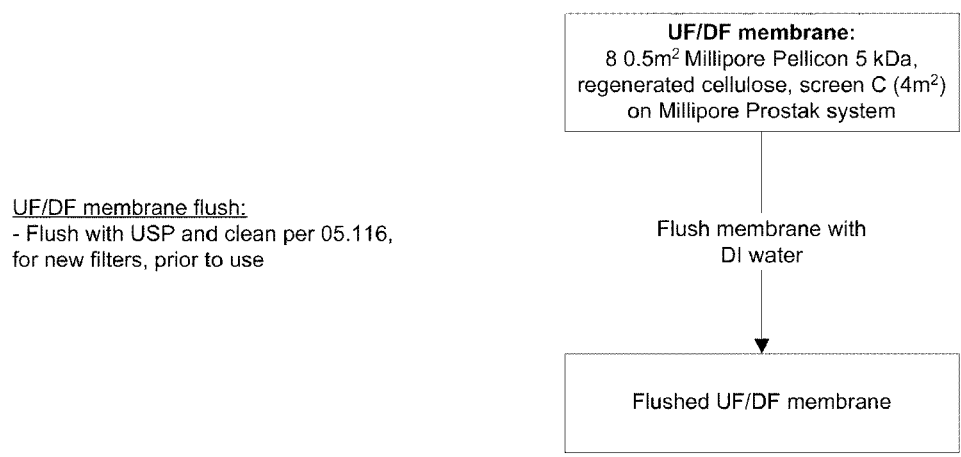

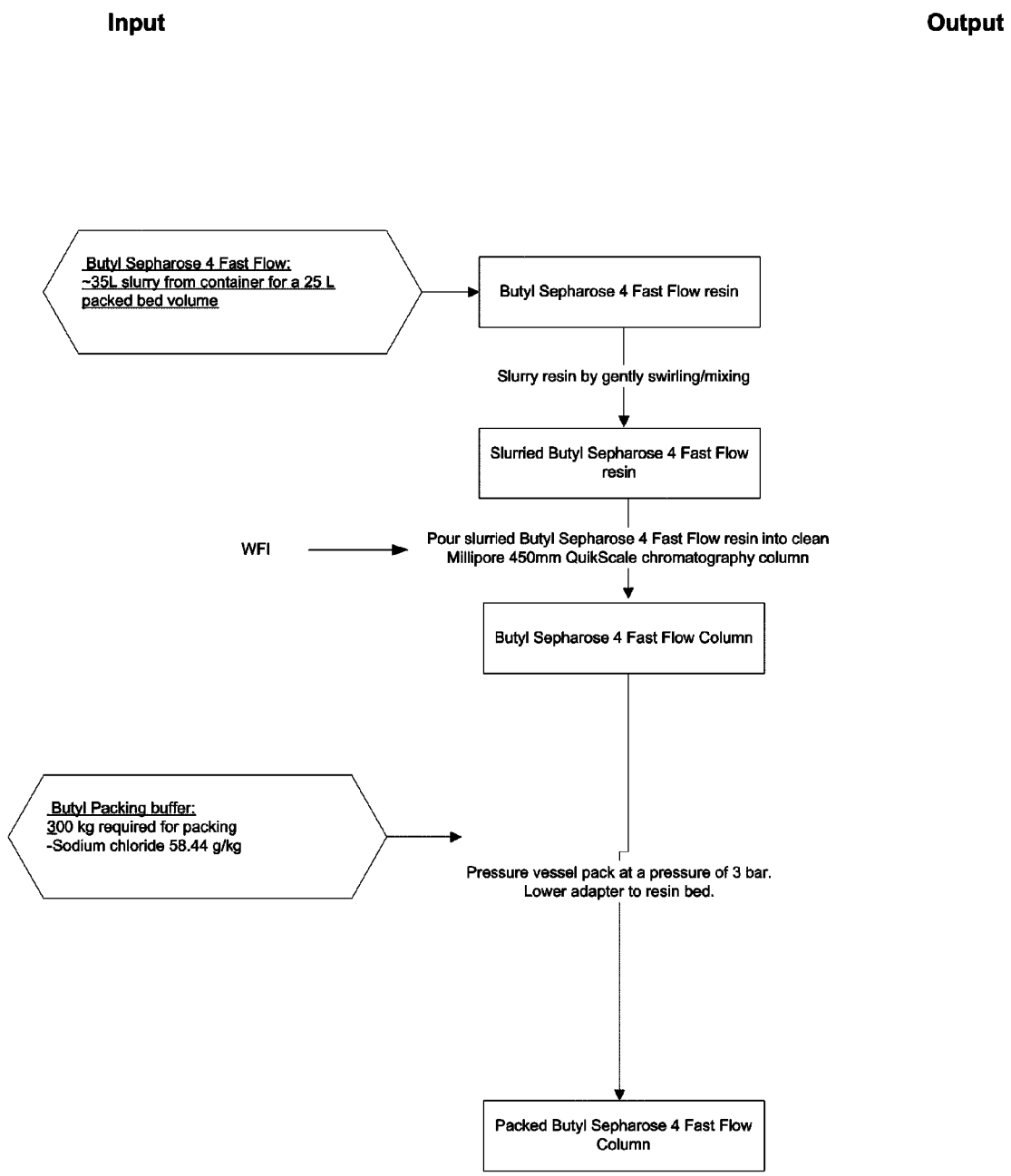

Figure 22A:
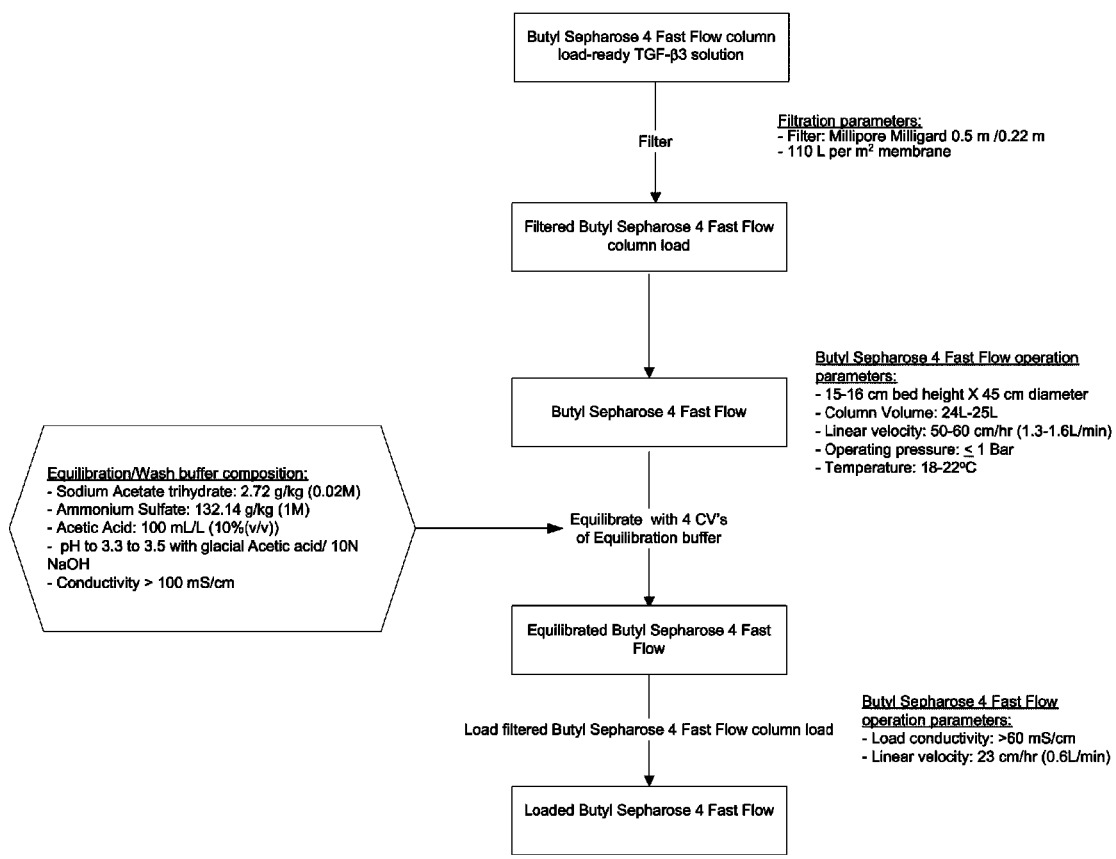

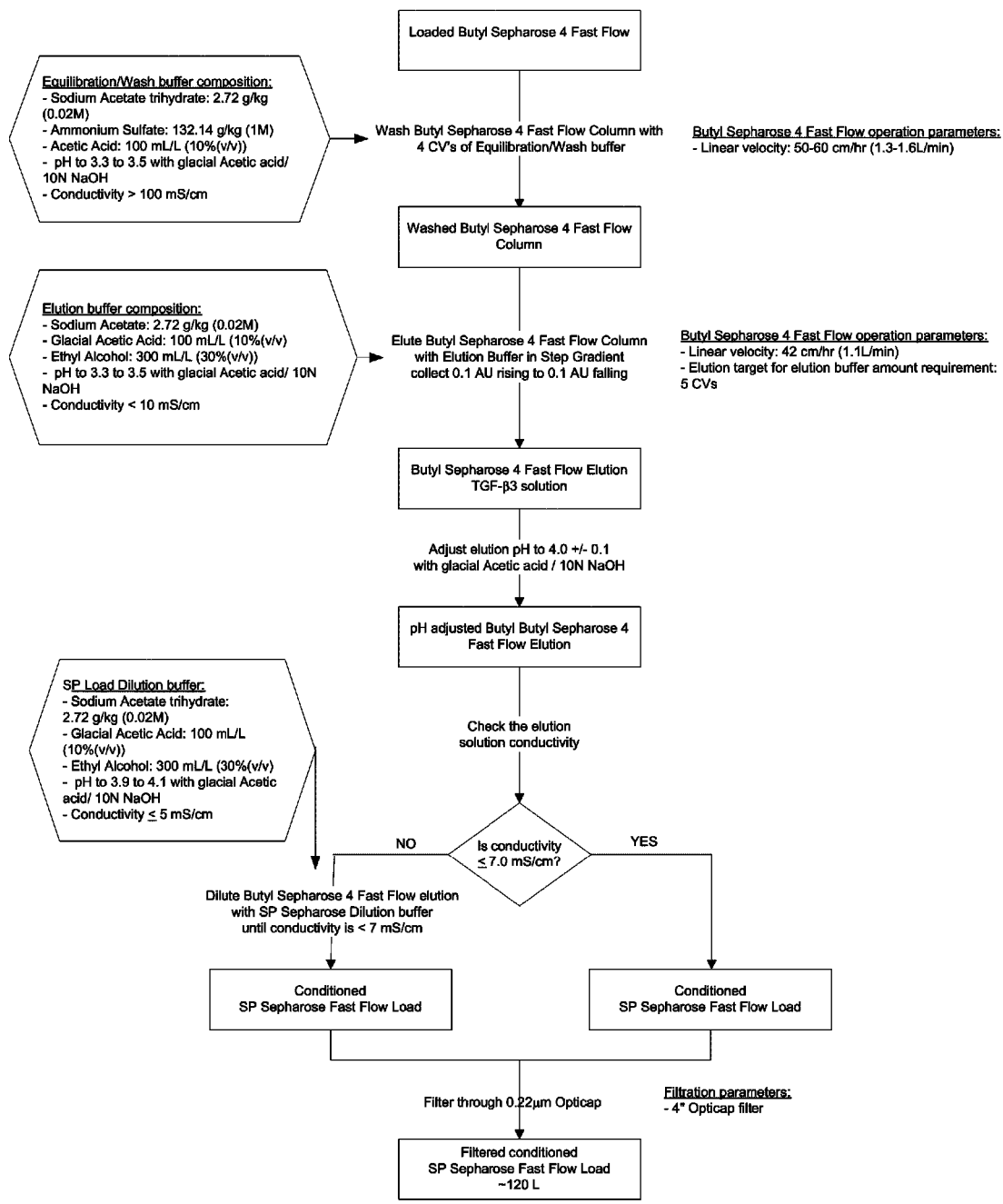
FIG 22A continued — Butyl Sepharose 4 Fast Flow (cont)

FIG 23A  Butyl Sepharose 4 Fast Flow Cleaning Post-Use
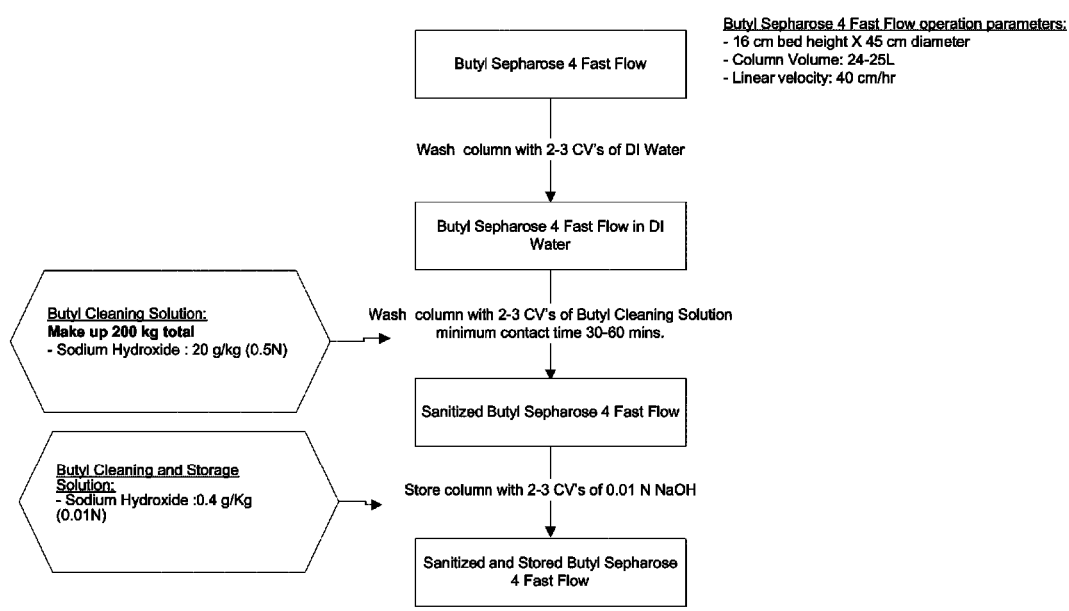
Butyl Sepharose 4 Fast Flow Cleaning Pre-Use/Regeneration
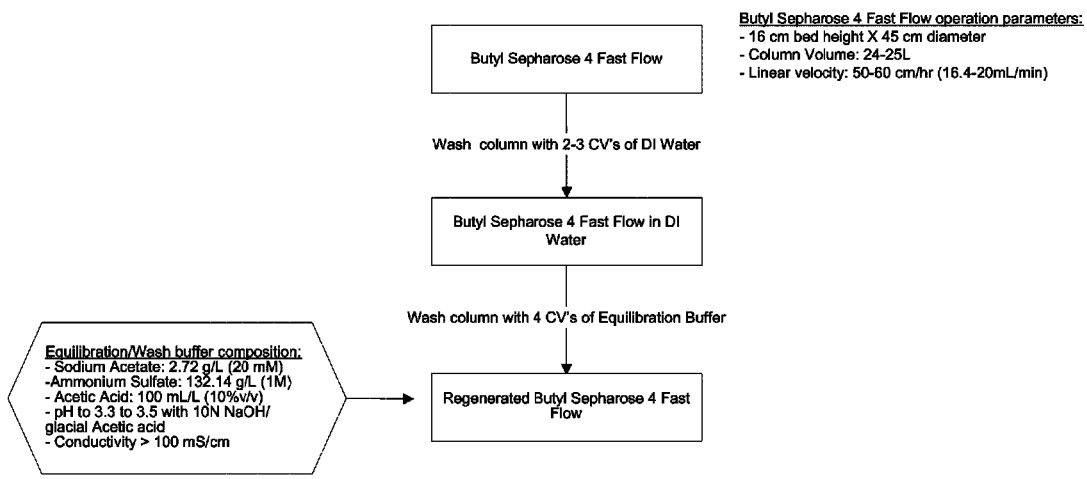

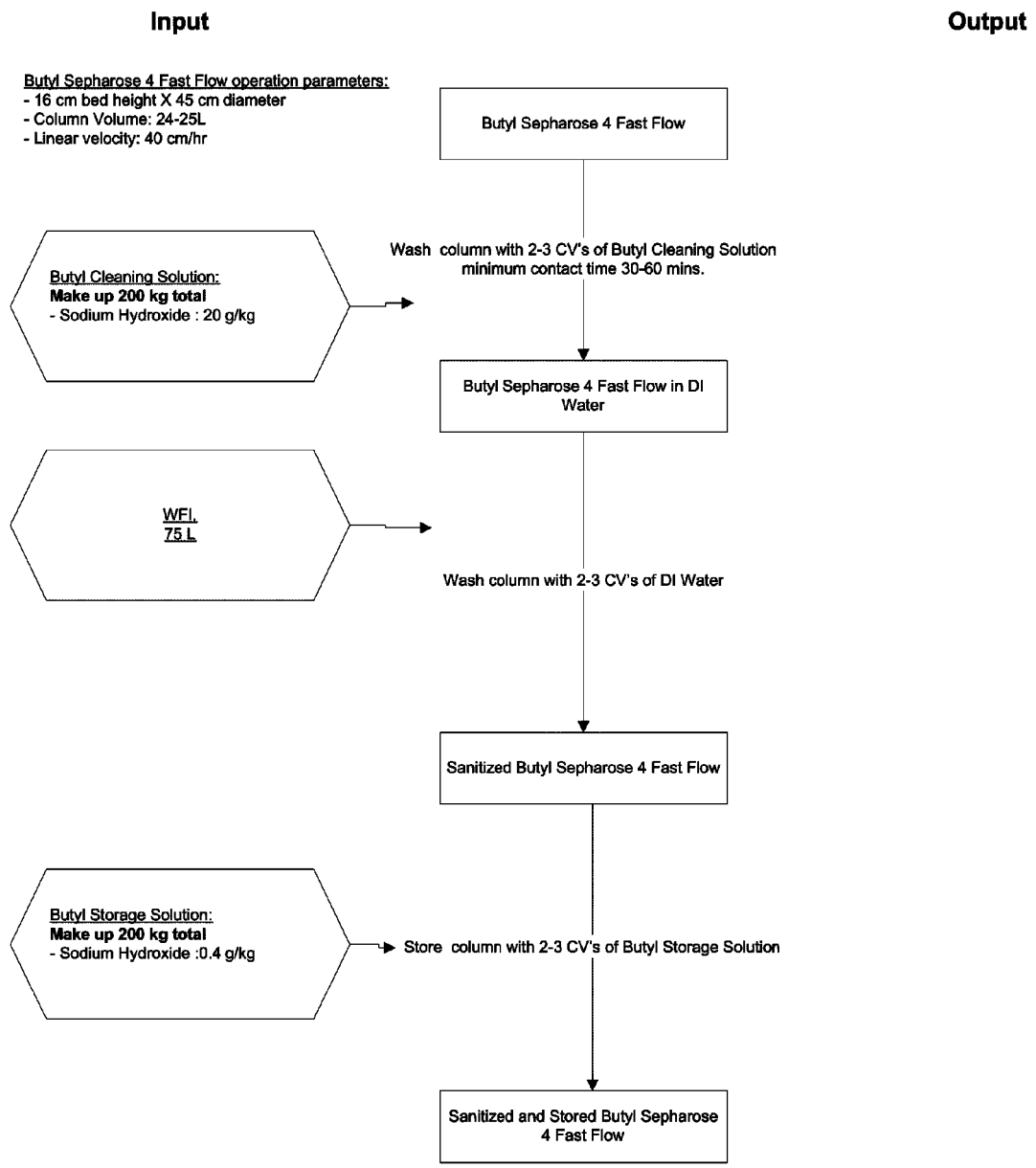
FIG 23B Butyl Sepharose 4 Fast Flow Cleaning Pre-Use

SEQUENCE LISTING

```
<160> NUMBER OF SEQ ID NOS: 5

<210> SEQ ID NO 1
<211> LENGTH: 336
<212> TYPE: DNA
<213> ORGANISM: Homo sapiens

<400> SEQUENCE: 1
gctttggaca ccaattactg cttccgcaac ttggaggaga actgctgtgt gcgcccctc      60 tacattgact tccgacagga tctgggctgg aagtgggtcc atgaacctaa gggctactat    120
gccaacttct gctcaggccc ttgcccatac ctccgcagtg cagacacaac ccacagcacg    180
gtgctgggac tgtacaacac tctgaaccct gaagcatctg cctcgccttg ctgcgtgccc    240
caggacctgg agccctgac catcctgtac tatgttggga ggaccccaa agtggagcag      300 ctctccaaca tggtggtgaa gtcttgtaaa tgtagc                              336

<210> SEQ ID NO 2
<211> LENGTH: 35
<212> TYPE: DNA
<213> ORGANISM: Artificial
<220> FEATURE:
<223> OTHER INFORMATION: Sense primer

<400> SEQUENCE: 2
gatataccat ggctttggac accaattact actgc                                35

<210> SEQ ID NO 3
<211> LENGTH: 37
<212> TYPE: DNA
<213> ORGANISM: Artificial
<220> FEATURE:
<223> OTHER INFORMATION: Sense primer

<400> SEQUENCE: 3
cagccggatc cggtcgactc agctacattt acaagac                              37

<210> SEQ ID NO 4
<211> LENGTH: 20
<212> TYPE: DNA
<213> ORGANISM: Artificial
<220> FEATURE:
<223> OTHER INFORMATION: T7 promoter primer

<400> SEQUENCE: 4
taatacgact cactataggg                                                 20

<210> SEQ ID NO 5
<211> LENGTH: 19
<212> TYPE: DNA
<213> ORGANISM: Artificial
<220> FEATURE:
<223> OTHER INFORMATION: T7 terminator primer

<400> SEQUENCE: 5
gctagttatt gctcagcgg                                                  19
```

PROTEIN FOLDING

CROSS-REFERENCE TO RELATED APPLICATIONS

This application is the national stage of International (PCT) Patent Application Serial No. PCT/GB2007/000814, filed Mar. 9, 2007, which claims priority to Great Britain Patent Application No. 0604964.7, filed Mar. 11, 2006; the contents of each application is incorporated herein by reference in its entirety.

The present invention relates to a method for folding, or refolding, proteins into an active form. The invention particularly relates to folding of members of the Transforming growth factor beta superfamily.

The Transforming growth factor beta (TGF-Beta) superfamily of growth factors are involved in the regulation of many cellular processes including proliferation, migration, apoptosis, adhesion, differentiation, inflammation, immunosuppression and expression of extracellular proteins. The TGF-Beta superfamily include: TGF-Beta 1, TGF-Beta 2, TGF-Beta 3, TGF-Beta 4, TGF-Beta 5, bone morphogenetic proteins (BMPs 1-16) growth and differentiation factors (GDFs 1-16), and activins/inhibins.

There are three mammalian isoforms of TGF-Beta, termed TGF-Beta 1, 2 and 3. TGF-Betas are produced by virtually all cell types (e.g., epithelial, endothelial, hematopoietic, neuronal, and connective tissue cells). TGF-Betas are secreted as 100-kDa latent inactive precursor molecules (LTGF-Beta). The LTGF-Beta molecules consist of: (a) a C-terminal 25 kDa dimer signal peptide (active fragment) and (b) the latent-associated peptide (LAP). LTGF-Beta is activated by cleavage of LAP from the active fragment by endopeptidases such as furin, plasmin, thrombin and acidification of the pericellar space. The liberated active TGF-Beta dimeric fragment is stabilized by hydrophobic interactions and by an inter-subunit disulfide bridge. Furthermore each monomer comprises several extended beta strands interlocked by three of the four intra-disulfide bonds and forms a tight structure known as the "Cysteine knot".

TGF-Beta family proteins have been proposed for a number of medical purposes. These include the reduction of scarring, promotion of wound healing and the stimulation of the replacement of damaged or diseased tissue at a variety of sites. These sites include the skin, bone, cartilage, neural tissue, connective tissue (e.g. tendons and ligaments), ocular tissue, liver and blood vessels etc. TGF-Beta 1 and TGF-Beta 2 have been shown to accelerate wound healing in experimental animal models, whilst their inhibition reduces subsequent scar formation. TGF-Beta 3 also significantly reduces scarring both in animal models and in humans and, in 2006, represents one of the members of the superfamily that is closest to gaining regulatory approval for use as a medicament.

It will be appreciated that such clinical uses of members of the TGF-Beta superfamily requires that efficient methods for producing significant quantities of active growth factors are made available.

Members of the TGF-Beta superfamily have been isolated or produced by recombinant means for a number of years. By way of example TGF-Beta 3 was originally purified from human platelets, human placenta and bovine kidney during the 1980s. In view of the therapeutic potential of TGF-Beta 3, numerous attempts have been made to produce this protein by recombinant methods. Due to the complexity of native biologically active TGF-Beta molecules (homodimeric protein with 8 intra-chain disulfide bonds and one inter-chain disulfide bond) they were originally expressed in eukaryotic organisms (e.g. see EP0200341B1). However, eukaryotic expression resulted in relatively low expression levels and was also associated with high process costs.

Prokaryotic hosts were therefore investigated. However it was found that microbial hosts were unable to correctly form the multiple disulfide bonds required for the growth factors to fold into an active form. The misfolded protein formed as insoluble inclusion bodies within the host cell and these bodies required solubilisation followed by renaturation to allow the protein to refold into its native biological active conformation.

A number of attempts have been made to overcome the problems associated with the formation of active growth factors from prokaryotic hosts. For instance, U.S. Pat. Nos. 5,922,846, 5,650,494 and EP-B-0433 225 propose methods for the renaturation of TGF-Beta family proteins from inclusion bodies. However none of these methods provide quick and efficient methods for the production of clinical grade growth factors. For instance the inventors have found that many of the prior art refolding methods contemplated in the abovementioned patents are ineffective. Further, the inventors have found that with even the most preferred prior art refolding conditions (e.g. 0.05M Tris, 1M NDSB-201, 20% (v/v) DMSO, 2% (w/v) CHAPS, 1M NaCl, 1% (w/v) GSH, 0.2 mg/mL TGF-Beta 3, pH 9.3 at 2-8° C.) it can take about 7 days to refold growth factors. This folding time represents an unacceptable delay in cGMP manufacture and would result in undesirably high operational costs when large quantities of active growth factor are required.

It is therefore an object of the present invention to overcome the problems associated with prior art methods for folding, or refolding, members of the Transforming Growth Factor Beta superfamily.

According to a first aspect of the present invention there is provided a method for folding a Transforming Growth Factor Beta, or functional analogue thereof, into a dimeric, biologically active form comprising adding solubilized, unfolded monomeric growth factor to a solution containing:

(i) 2-(cyclohexylamino)-ethanesulfonic acid or a functional analogue thereof; and
(ii) a low molecular weight sulfhydryl/disulfide redox system; and incubating the growth factor in the solution until dimeric biologically active growth factor is formed.

The present invention is based on experiments conducted by the inventors that were conducted in an attempt to improve prior art folding methods.

The Transforming Growth Factor Beta (TGF-Beta) may be any TGF-Beta (e.g. TGF-β1, TGF-β2 or TGF-β3). However it is preferred that the TGF-Beta is TGF-Beta3 (TGF-β3).

By "functional analogue thereof" we mean variants of a TGF-beta that retain the biological activity of the wild type growth factor. The functional analogue is preferably a protein and, in mature form, may comprise a dimer of two monomeric polypeptides of about 112 amino acids in length although it will be appreciated that functional analogues may be truncated or elongated when compared to the wild-type. The term also encompasses mutants of wild-type TGF-beta and particularly of TGF-Beta 3 that retain, or even have improved, activity when compared to the wild-type. The inventors have found that the methods of the invention are also applicable to folding or refolding of such mutants.

It will be appreciated that "folding", as defined in the present invention, encompasses the "re-folding" of previously folded proteins, and indeed this re-folding of proteins constitutes a preferred subset of the broader folding encompassed by the invention.

EP 0 433 225 contemplates a wide variety of "refolding conditions" that are alleged to permit a denatured monomer to dimerise and assume a biological active form. EP 0 433 225 discloses that such conditions should include the presence of a "solubilizing agent" and a redox system which permits the continuous oxidation and reduction of the thiol/disulfide pairs. It further contemplates a long list of such solubilizing agents including detergents; organic, water miscible, solvents; and phospholipids or a mixture of two or more such agents. Examples of the detergents contemplated in the specification include: surface active compounds, such as sodium dodecylsulfate (SDS), Triton or Tween, non-ionic mild detergents (e.g. digitonin), cationic mild detergents (e.g. N-[2,3-(Dioleyloxy)-propyl]-N,N,N-trimethylammonium), anionic mild detergents (e.g. sodium cholate, sodium deoxycholate) and zwitterionic ones (e.g. sulfobetaines (Zwittergent), 3-(3-chlolamidopropyl)dimethylammonio-1-propane-sulfonate (Chaps), 3-(3-chlolamidopropyl)dimethylammonio-2-hydroxy-1-propane-sulfonate (Chapso).

The inventors decided to test out a variety of detergents, including those contemplated in EP 0 433 225, and were surprised to find that most of the detergents they tested were ineffective for folding or refolding members of the TGF-Beta superfamily whereas those that did work took an unacceptable amount of time to yield useful amount of active growth factor. Tables 1 and 2 of the Example illustrate that a number of such detergents were ineffective. However to the inventors' surprise they found that the use of 2-(cyclohexylamino)-ethanesulfonic acid (CHES), and analogues thereof, in combination with a low molecular weight sulfhydryl/disulfide redox system, in accordance with the first aspect of the invention, was particularly effective for producing correctly folded dimeric growth factor.

The inventors have found that the method according to the first aspect of the invention represents a significant improvement over prior art methods. The method results in significantly improved speed of the process compared to methods previously disclosed in the literature. In preferred embodiments of the method of the invention folding of the growth factor may be completed within 5 days; preferably within 3 days; more preferably within 2 days; and most preferably after approximately 24 hours of initiating the folding process.

By the term "2-(cyclohexylamino)-ethanesulfonic acid or analogues thereof" we mean the detergent CHES and chemical analogues thereof that retain the refolding properties of CHES.

Suitable analogues of CHES that may be used in accordance with the methods of the invention may be defined by the following formula:

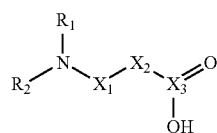

(I)

wherein:

$R_1$ and $R_2$ are the same or different and are selected from the group consisting of hydrogen, substituted or unsubstituted $C_{1-4}$ alkyl groups, substituted or unsubstituted $C_{3-8}$ cycloalkyl groups, or a substituted or unsubstituted aromatic nucleus, or $R_1$ and $R_2$ together form a ring system having up to 10 atoms;

$X_1$ and $X_2$ are independently selected from —O—, —S—, —S(O), —S(O_2)—, —NR_3—, —CHR_4— and CHR_5 where $R_3$, $R_4$, and $R_5$ are the same or different and are independently selected from the group consisting of hydrogen, substituted or unsubstituted $C_{1-4}$ alkyl groups, substituted or unsubstituted $C_{3-8}$ cycloalkyl groups, or a substituted or unsubstituted aromatic nucleus or any two of $R_3$, $R_4$ and $R_5$ may together form a ring system having up to 6 carbon atoms, subject to the proviso that at least one of $X_1$ and $X_2$ is —CHR_4— or —CHR_5—; and $X_3$ is selected from C, S, S=O, or P—OH If one or more of $R_{1-5}$ are alkyl groups then, depending on the number of carbon atoms they contain, they may be normal, secondary, tertiary or iso-groups. Examples of suitable alkyl groups for $R_{1-5}$ are Me, Et, n-Pr, i-Pr, n-Bu, sec-Bu and E-Bu groups.

If one or more of $R_{1-5}$ are cycloaliphatic then they are preferably a substituted or unsubstituted cyclohexyl group, most preferably unsubstituted.

If one or more of $R_{1-5}$ are aromatic then they are preferably a substituted or unsubstituted phenyl group.

Preferably $R_1$ is hydrogen and $R_2$ is cyclohexyl. Alternatively or additionally $X_1$ and $X_2$ are preferably —CH_2—, alternatively or additionally $X_3$ is —S=O.

Preferred examples of compounds of formula (I) that may be employed in the invention are:

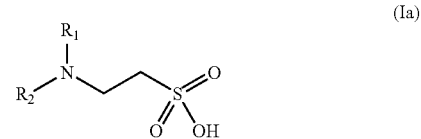

(Ia)

(i.e. a compound of formula (I) in which $X_1$ and $X_2$ are both —CH_2— and $X_3$ is S=O);

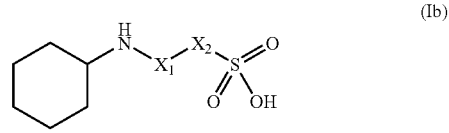

(Ib)

(i.e. a compound of formula (I) in which $R_1$ is hydrogen, $R_2$ is cyclohexyl and $X_3$ is S=O); and

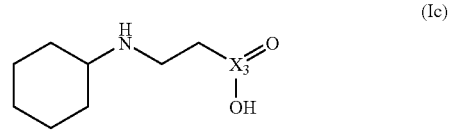

(Ic)

(i.e. a compound of formula (I) in which $R_1$ is hydrogen, $R_2$ is cyclohexyl, and $X_1$ and $X_2$ are both —CH_2—).

The preferred example of each of formula (Ia), (Ib) and (Ic) is CHES, i.e.

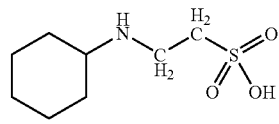

The inventors have established that CHES, and the low molecular weight sulfhydryl/disulfide redox system, may be used alone to fold the growth factor. However, in some embodiments of the invention, the inventors have found that CHES may also be advantageously combined with other agents that have detergent/folding activity. Examples of such agents include: Taurodeoxycholate, Isopropyl Alcohol, Arginine-HCl, Non-detergent Sulphobeatine-201 and Non-detergent Sulphobeatine-211.

It is preferred that the solution comprises a concentration of about 10 mM to 2.0 M CHES; more preferably 100 mM-1.0 M and most preferably about 0.7 M CHES.

The abovementioned concentrations of CHES may also be used when CHES is combined with other agents. For instance a preferred combination of agents that promote refolding is about 30 mM Taurodeoxycholate and 0.7 M CHES.

By the term "low molecular weight sulfhydryl/disulfide redox system" we mean systems that allow the formation of disulfide bonds in the solution. Suitable systems include reagent combinations such as Glutathione in its oxidized and reduced form, dithiothreitol in its oxidized and reduced form, beta-mercaptoethanol or beta-mercaptomethanol in its oxidized and reduced form, Cystine and its reduced form, and Cystamine and its reduced form. These reagents may be used at a concentration of about 1 µM to 250 mM, especially of about 100 µM to 10 mM. The molar ratio of such systems for the oxidized and the reduced forms may be between 100:1 and 1:100, especially between 6:1 and 1:6.

It is preferred that the low molecular weight sulfhydryl/disulfide redox system comprises the use of Glutathione in its reduced (GSH) and oxidised (GSSG) forms. Preferably the solution contains about 20 µM-200 mM reduced Glutathione; more preferably 200 µM-20 mM reduced Glutathione; and most preferably about 2 mM reduced Glutathione. The solution may also contain about 4 µM-40 mM oxidised Glutathione; more preferably 40 µM-4 mM oxidised Glutathione; and most preferably about 400 µM oxidised Glutathione.

Accordingly, preferred low molecular weight sulfhydryl/disulfide redox systems may comprise 200 µM-20 mM reduced Glutathione and 40 µM-4 mM oxidised Glutathione. The exact ratio of GSH:GSSH will depend on a number of factors including: which growth factor is being folded; the pH of the solution and the CHES analogue employed in the method of the invention. By way of example, preferred low molecular weight sulfhydryl/disulfide redox systems for folding TGF-Beta 3 comprises about 2 mM reduced Glutathione and either about 400 µM or about 2 mM reduced Glutathione.

As explained in more detail below, in preferred embodiments of the invention the low molecular weight sulfhydryl/disulfide redox system may be "aged" before used to refold the TGF-Beta.

Preferred methods for folding the growth factors involve the use of CHES in combination with GSH and GSSG as the low molecular weight sulfhydryl/disulfide redox system. Examples of preferred conditions include exposing unfolded growth factor to:

(a) 0.7M CHES, 2 mM GSH and 0.4 mM GSSG;
(b) 30 mM Taurodeoxycholate, 0.7 M CHES, 2 mM GSH and 0.4 mM GSSG; or
(c) 30 mM Taurodeoxycholate, 0.7 M CHES, 2 mM GSH and 2 mM GSSG.

It will be appreciated that the abovementioned agents may be dissolved in water to make a solution according to the invention. However it will also be appreciated that the agents may be dissolved in a solution comprising a number of other compounds. For instance, the solution may also further comprise salts. Salts that can be used in the solution include salts of sodium, potassium, and calcium with chloride, sulphate, phosphate, acetate etc. It is preferred that the solution is a sodium chloride solution at a concentration of 0.5 to 2 M. The solution may, for example, be phosphate buffered saline.

During their investigations the inventors also established that folding conditions could be optimised by adjusting the pH and the temperature at which folding is encouraged to proceed.

Optimal temperature depended on a number of factors such as the agents used, the pH and also the amount of growth factor to be refolded. Under most circumstances a temperature of below about 15° C. is preferred (for example 2-8° C. or about 10° C.). However higher temperatures (e.g. room temperature) were also effective for some conditions.

The inventors discovered that it was generally preferable to carry out the method of the invention at an alkaline pH. The pH is preferably above about pH 8.0. and more preferrably above a pH of about pH 8.5. A most preferred pH for the solution is a pH of about 9.5.

The amount of unfolded growth factor added to the solution was also found to influence the efficiency of the folding. In general about 0.005-0.75 mg/mL of a growth factor may be added to the solution; preferably 0.01-0.5 mg/mL; more preferably about 0.12-0.25 mg/mL of the growth factor; and most preferably about 0.25 mg/mL (i.e. 250 µg/ml).

The methods of the invention may be employed to fold any monomer of the Transforming Growth Factor Beta superfamily into a dimeric, biologically active form. It is preferred that the method is used to fold a TGF-Beta per se (for example TGF-Beta 1, TGF-Beta 2, or TGF-Beta 3).

It is also preferred that the method is used to fold monomeric precursors (into active dimer growth factor) that have been produced in prokaryotic hosts that have been transformed to express the growth factor. For instance the method is particularly useful for folding growth factors that are located within inclusion bodies of bacteria that have been transformed with an expression vector encoding a recombinant growth factor.

It is most preferred that the methods of the invention are used to fold monomeric TGF-Beta 3 that is located in an inclusion body of a bacterium transformed with a TGF-Beta 3 expression vector (e.g. as described in Example 1 or as known to the art). It is most preferred that the TGF-Beta 3 is human TGF-Beta 3, recombinant human TGF-Beta 3, or human TGF-Beta 3 that contains mutations that optimise the growth factor for clinical use in humans.

Examples of most preferred conditions employed to fold TGF-Beta 3 include:

(a) 0.7 M 2-(cyclohexylamino) ethanesulfonic acid (CHES), 2 mM reduced Glutathione (GSH), 0.4 mM oxidised Glutathione (GSSG), 0.12 mg/mL TGF-Beta 3, pH 9.5 at 2-8° C.;
(b) 30 mM taurodeoxycholate, 0.7 M CHES, 2 mM GSH, 0.4 mM GSSG, 0.12 mg/mL TGF-Beta 3, pH 9.5 at 2-8° C.;
(c) 30 mM taurodeoxycholate, 0.7 M CHES, 2 mM GSH, 2 mM GSSG, 0.12 mg/mL TGF-Beta 3, pH 9.5 at 2-8° C.; or
(d) 0.7 M CHES, 1 M NaCl, 2 mM GSH, 0.4 mM GSSG, 0.25 mg/mL TGF-Beta 3, pH 9.5 at 2-8° C./room temperature.

The inventors developed the folding methods according to the invention in a laboratory (as described in Example 1) and then went on to scale-up the methodology as described in Example 2. It will be appreciated that the scale-up of the methods represent an important feature of the invention. Therefore according to a second aspect of the invention there is provided a method of producing an active member of the Transforming Growth Factor Beta superfamily from a prokaryotic host, the method comprising:

(a) fermentation of prokaryotic organisms that have been transformed to express a member of the Transforming Growth Factor Beta superfamily;

(b) isolation of inclusion bodies and recovery of expressed protein from the inclusion bodies;

(c) refolding of the member of the Transforming Growth Factor Beta superfamily according to the first aspect of the invention; and (d) purification of the refolded member of the Transforming Growth Factor Beta superfamily.

It is preferred that step (a) involves the fermentation of bacteria that have been transformed with an expression vector encoding a member of the Transforming Growth Factor Beta superfamily. The vector preferably encodes a TGF-Beta and most preferably encodes a human TGF-Beta 3, or a functional analogue thereof. It will be appreciated that the transformed bacterium may be generated using molecular biology techniques known to the art. An example of such a bacterium is given in Example 1.

It is preferred that the organisms are fermented according to conventional techniques. This may involve fermentation of a cell paste and harvesting the cells by taking samples from the fermentation and centrifuging the sample to isolate the organisms.

Step (b) of the method of the second aspect of the invention may involve lysis of the organisms recovered by centrifugation. The inclusion bodies (IB) may then be recovered by further centrifugation and washing steps. Preferably the IBs are further processed by taking steps to solubilize the protein within the IBs and then clarifying them.

The protein (i.e. the unfolded growth factor) from the isolated IBs is then subjected to the folding methods of the first aspect of the invention according to step (c) of the method of the second aspect of the invention.

The refolded growth factor should then be further purified according to step (d). Purification may involve a number of biochemical purification steps such as ultrafiltration and chromatography. Preferred purification procedures are illustrated in 1.15, 1.16 and 1.17 of Example 1. In a preferred embodiment the growth factor is first filtered; further purified by hydrophobic interaction chromatography; and then finally purified by cation exchange chromatography.

Optionally the method of the second aspect of the invention may further comprise a step (e) wherein the growth factor is formulated at a desired concentration in a solution and placed in vials. This solution may be the final formulation for clinical use or may be formulated for storage and/or transported. The growth factor may then be finished to form the final clinical product at a later date.

The inventors have recognised that WO99/18196 discloses the use of CHES for refolding Bone Morphogenetic Proteins (BMPs). However the techniques disclosed in WO99/18196 would not be considered by a skilled man to be useful for refolding TGF-Beta, and TGF-Beta3 in particular, according to the methods of the first or second aspects of the invention. The skilled person would come to this conclusion for a number of reasons. These include:

(a) WO99/18196 discloses methods for the solubilisation of the BMP inclusion bodies should use denaturants such as Guanidine-HCL or by acidification with an acid such as Acetic Acid. The inventors have found that acidification resulted in low recoveries of TGF-Beta 3 from the inclusion bodies. They found that when TGF-Beta 3 was solubilised in acid and the pH was then titrated to 9.5 (the preferred pH for refolding according to the invention), that this change from acid to alkaline pH resulted in irreversible aggregation of TGF-Beta 3 (due to the TGF-Beta 3 crossing its isoelectric point (pH 6.4)). This resulted in very low TGF-Beta 3 yields. The Guanidine-HCL was also examined as a solubilisation agent, though it gave very good recoveries of TGF-Beta 3 from inclusion bodies it was too strong a denaturant and prevented TGF-Beta 3 from refolding. Accordingly the inventors found the solubilisation steps of the prior art unsuitable. Experimentation did establish that solubilisation of inclusion bodies using 6 M Urea and 0.1 M DTT gave good recoveries of TGF-Beta 3 and allowed the TGF-Beta 3 to refold once it was diluted in the refold buffer. Accordingly it is preferred that TGF-Beta 3 is solubilised from inclusion bodies using Urea and DTT.

(b) WO99/18196 also states that the BMP can be clarified using size exclusion chromatography (SEC) or reverse phase high performance liquid chromatography (RP-HPLC). Both these methods would be unsuitable for the commercial scale manufacture of TGF-Beta 3. In SEC, sample volume influences the resolution of the sample (the smaller the sample volume the better the purification resolution). Commercial scale methods according to the second aspect of the invention may produce about 50 L of solubilised inclusion bodies. It would be impractical to use SEC for such volumes because to process this volume in a single run would require a column (or multiple columns) with a single/combined bed-volume of 724 L. RP-HPLC is generally used as analytical tool due to the small column volume and again would be impractical to use in the commercial scale manufacture of TGF-Beta 3 for the same reasons. It is preferred that the method of the second aspect of the invention uses Tangential Flow Filtration (TFF) which gives TGF-β3 purities of 70% and above.

(c) It is known that purity of an expressed protein affects refold yields. As a general rule the higher the purity of the expressed protein the higher the refold yields. The inventors have found that TGF-β3 purities of 70% (of total protein) and above give high refold yields and that low TGF-β3 purities (<50% of total protein) gave low refold yields. Accordingly it is preferred that TGF-β3 used in methods of the invention are greater than 50% pure and more preferably about 70% (or more) pure. This purity may be achieved by including washing steps of the inclusion bodies and clarification of the solubilised TGF-Beta 3 using TFF (e.g. see Example 2).

(d) TGF-Beta 3 undergoes significant changes in conformation (secondary structure) and solubility at different pHs. As the pH of a TGF-Beta 3 containing solution is moved from acidic (<pH 3.8) to alkaline pH (<pH 8.0), aggregates appear, with an aggregation maximum occurring between pH 6.5 and pH 8.5. WO99/18196 states that the preferred pH of refolding BMPs to be approximately 8.5. However this would be unsuitable for the refolding of TGF-Beta 3 as this would cause TGF-Beta 3 to aggregate and therefore significantly reduce refold efficiency and yield. Accordingly it is preferred that the methods of the invention utilising a refolding buffer at pH greater than 8.5, preferably greater than pH 9.0 and most preferably a pH of about 9.5.

(e) The inventors have also found that the optimal concentrations of the Redox pair (e.g. reduced and oxidised Glutathione) in the Refold Buffer can be different for BMP and TGF-Beta 3. Preferred concentrations of Reduced Glutathione (GSH) and Oxidised Glutathione (GSSG) used in the manufacture of TGF-Beta 3 according to the invention is 2 mM and 0.4 mM respectively. Furthermore the inventors have found that it is most preferable, once the redox pair are dissolved in solution, that the buffer is aged for at least 2 hours, preferably at least 3-5 hours and most preferably for about 7 hours. The inventors do not wish to be bound by any hypothesis with regards the benefits of the redox pair "aging", they have noted that, in aqueous solutions GSH readily oxidises to produce GSSG and at physiological pHs the half-life of GSH is approximately 4 hrs. Furthermore the inventors suspect that the half-life of GSH in preferred TGF-Beta refolding buffer (pH 9.5) would be significantly lowered (at alkaline pHs there would be less hydrogen ions to protonate the reactive thiolate groups in GSH to produced unreactive thiols). A conservative estimation of half life of GSH at pH 9.5 would be 3 hrs. Therefore after 7 hours of buffer aging the concentrations of the redox pair would therefore be approximately 0.5 mM of GSH and 1.15 mM of GSSG. Accordingly these concentrations are preferred concentrations for refolding TGF-Beta3. WO99/18196 states the preferred concentration of the redox pair to be 2 mM of GSH and 1 mM of GSSG (for folding BMP). This increased concentration of GSH would significantly prolong the refolding of TGF-Beta 3, and may reduce yield (as GSH breaks the disulfide bonds in proteins). In addition WO99/18196 states the requirement of 5 mM EDTA in the refold buffer. The presence of chelating agents such as EDTA in the refold buffer would stabilise GSH (i.e increase GSH half-life) this would further increase the refold time of TGF-Beta 3 and may reduce yield.

(f) WO99/18196 states the preferred concentration of BMP in the refold buffer to be 1-100 µg/mL, this is significantly lower than the concentrations the inventors have found is useful in the manufacture of TGF-Beta 3 (optimally 250 µg/mL). 250 µg/mL of TGF-Beta 3 gave a higher refold efficiencies than 100 µg/mL of TGF-Beta 3. It is therefore preferred that the methods of the invention utilise more that 100 µg/mL of TGF-Beta 3 in the refolding step and preferably about 250 µg/mL of TGF-Beta 3.

(g) WO99/18196 states the preferred temperature of the refold of BMPs to be 20° C. The inventors have observed that refolds of TGF-Beta 3 done at room temperature (22° C.) results in the aggregation of TGF-Beta 3 and that refolding of TGF-Beta 3 should occur below 15° C. (preferably 2-8° C. or about 10° C.) to support the productive folding pathway of TGF-Beta 3 and the suppression of hydrophobic interaction.

Figure 10:
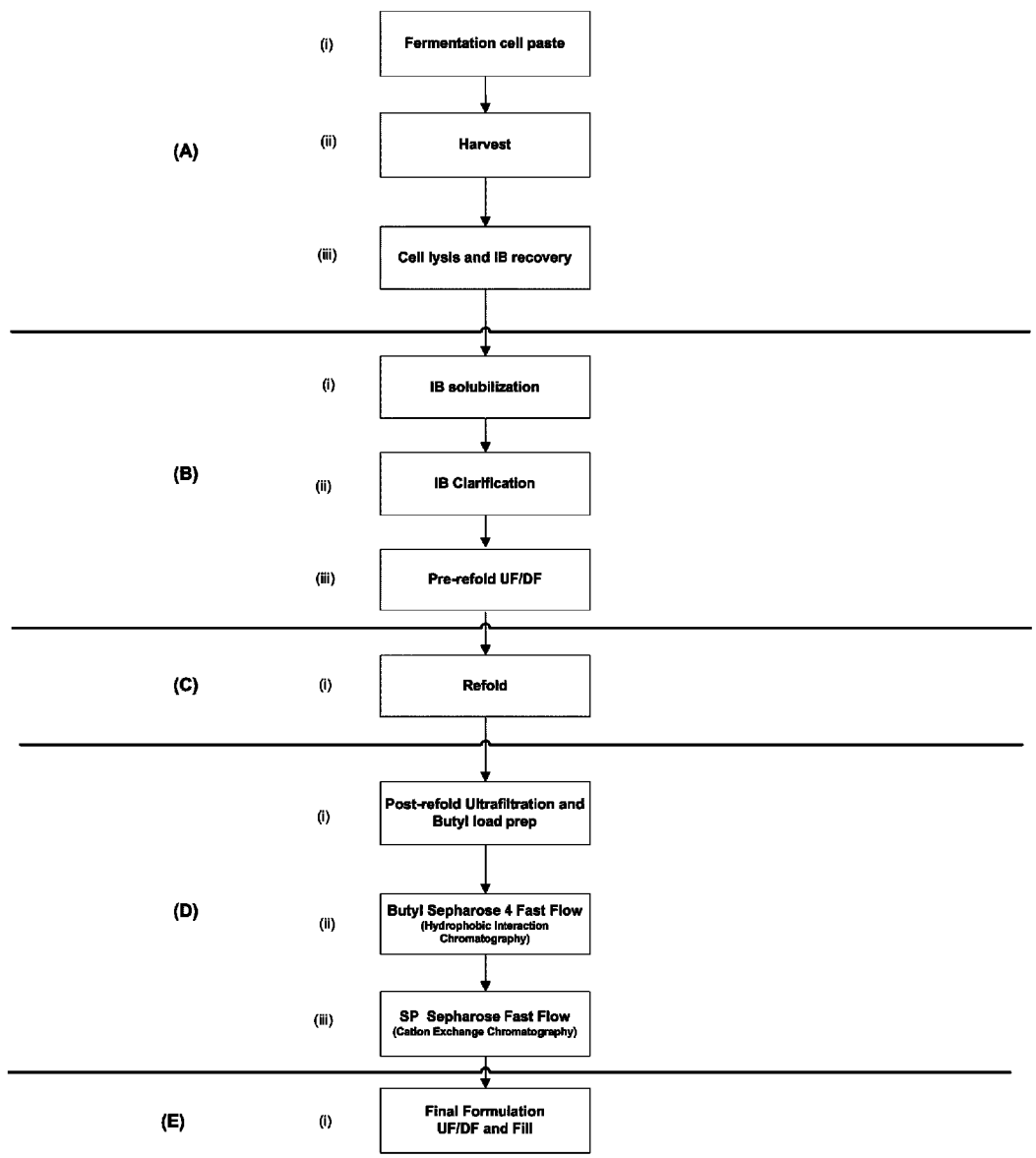

A most preferred method according to the second aspect of the invention is illustrated in FIG. 10. Details of conditions and protocols suitable for use in the preferred method illustrated in FIG. 10 are set out in FIGS. 11 to 26. It will be appreciated by the skilled person that, although the conditions and protocols set out in these Figures may preferably be used in the method illustrated in FIG. 10, they may, except for where the context requires otherwise, be used to effect any suitable folding method in accordance with the present invention.

Figure 2:
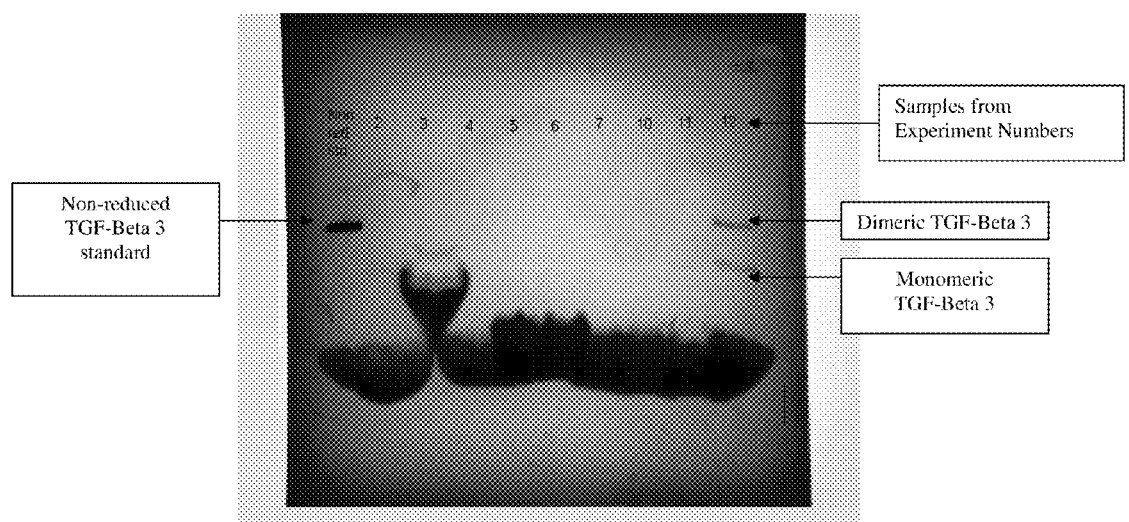
Figure 4:
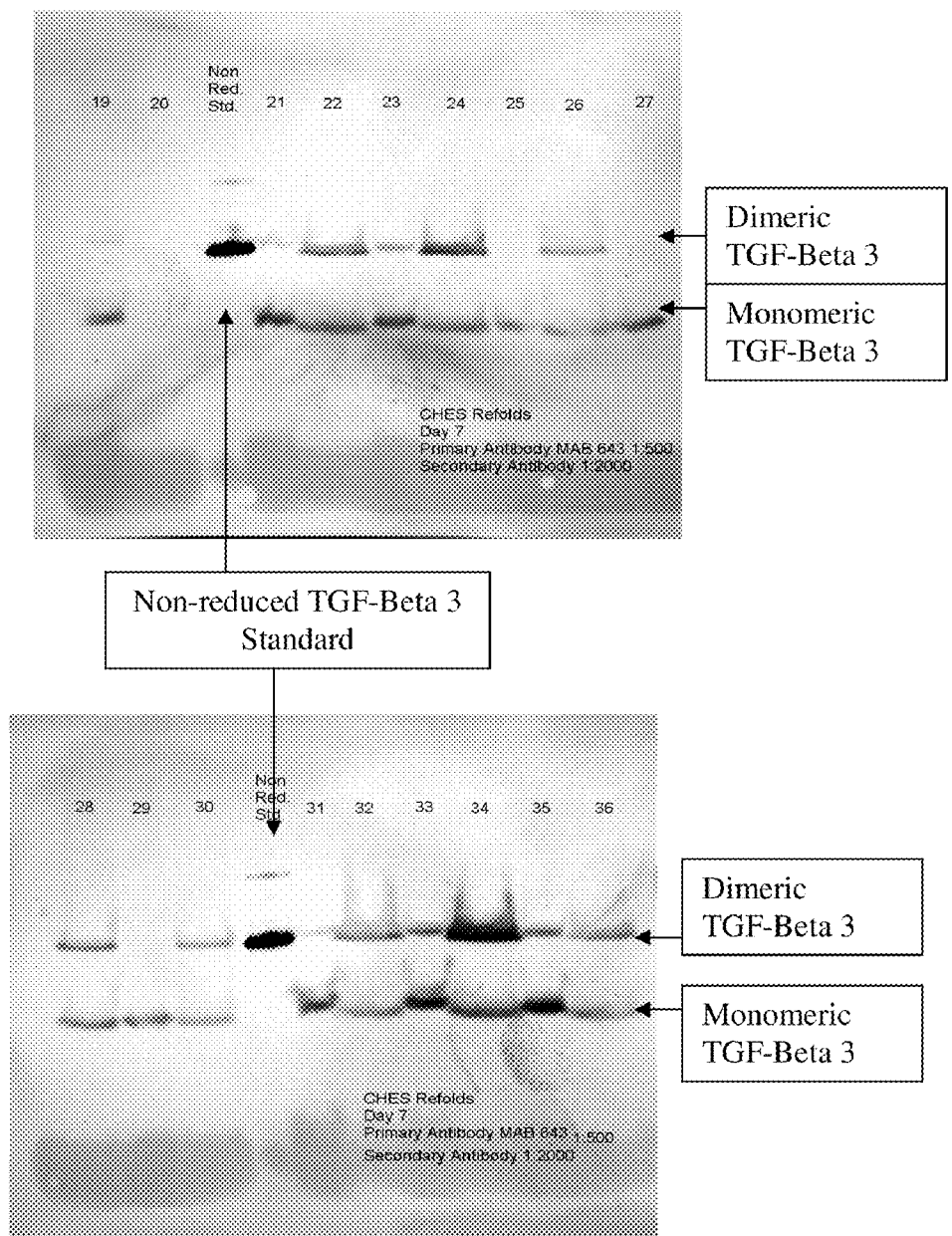
Figure 5:
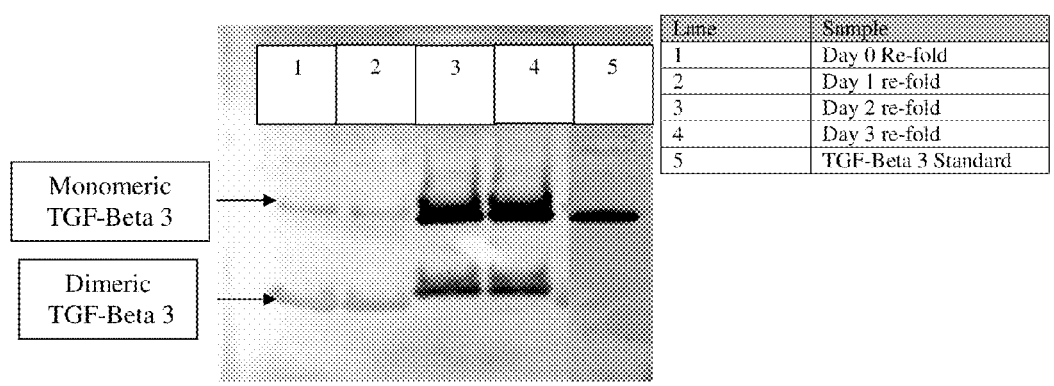
Figure 6:
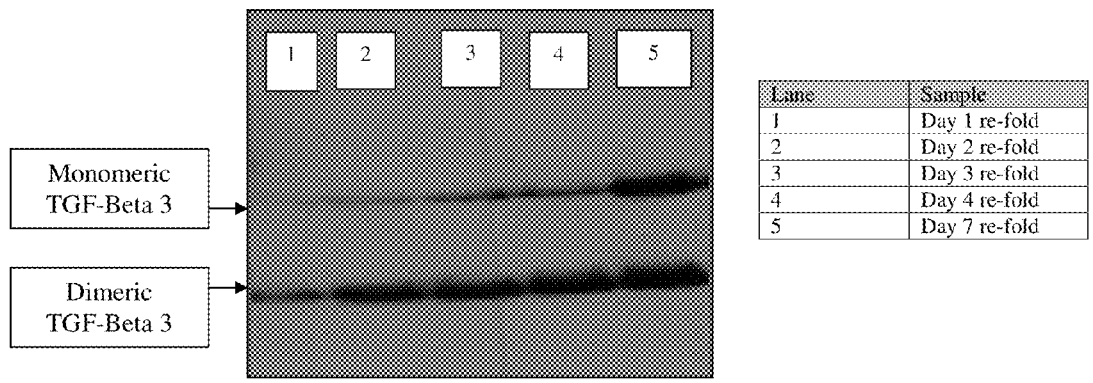

The invention will be illustrated further by Examples and with reference to the following drawings, in which:

FIG. 1: is a photograph of an illustrative SDS-PAGE gel of post-induction samples from shake flasks referred to in 1.4 of Example 1 wherein lane 1 & 6 are Mark 12 standards (Invitrogen); and lanes 2-5 are loaded with 3 µL of clones 1-4 respectively (3 hrs post induction);

FIG. 2: is a photograph of an illustrative Western blot wherein the first lane is a standard of non-reduced TGF-Beta 3 and lanes 2-12 correspond to Experimental conditions 2-12 in Table 1 of Example 1 and demonstrates that condition 12 was successful in producing correctly folded dimeric TGF-Beta 3;

FIG. 3: is a photograph of an illustrative Western blot demonstrating the folding of monomeric and dimeric TGF-Beta 3 as discussed at 1.14 of Example 1 wherein lanes 1-18 correspond to Experimental conditions 1-18 in Table 3 of Example 1 after 7 day incubations;

FIG. 4: is a photograph of an illustrative Western blot demonstrating the folding of monomeric and dimeric TGF-Beta 3 as discussed at 1.14 of Example 1 wherein lanes 19-36 correspond to Experimental conditions 19-36 in Table 4 of Example 1 after 7 day incubations;

FIG. 5: is a photograph of an illustrative Western blot demonstrating the folding of monomeric and dimeric TGF-Beta 3 for most preferred refolding conditions according to the invention as discussed at 1.14 of Example 1 wherein lane 1 represents refolding at day 0; lane 2 represents refolding after 1 day; lane 3 represents refolding after 2 days; lane 4 represents refolding after 3 days and lane 5 is a standard of non-reduced TGF-Beta 3;

FIG. 6: is a photograph of an illustrative Western blot demonstrating the folding of monomeric and dimeric TGF-Beta 3 utilising prior art refolding techniques as discussed at 1.14 of Example 1 wherein lane 1 represents refolding after 1 day; lane 2 represents refolding after 2 days; lane 3 represents refolding after 3 days; and lane 5 represents refolding after 7 days treatment;

FIG. 7: represents chromatograms illustrating the amount of dimeric TGF-Beta 3 produced by a most preferred refolding condition according to the invention as discussed at 1.14 of Example 1 after purification by cation exchange HPLC of refolded TGF-Beta 3 samples (a) on day 0, (b) after 1 day and (c) after 2 days.

Figure 8:
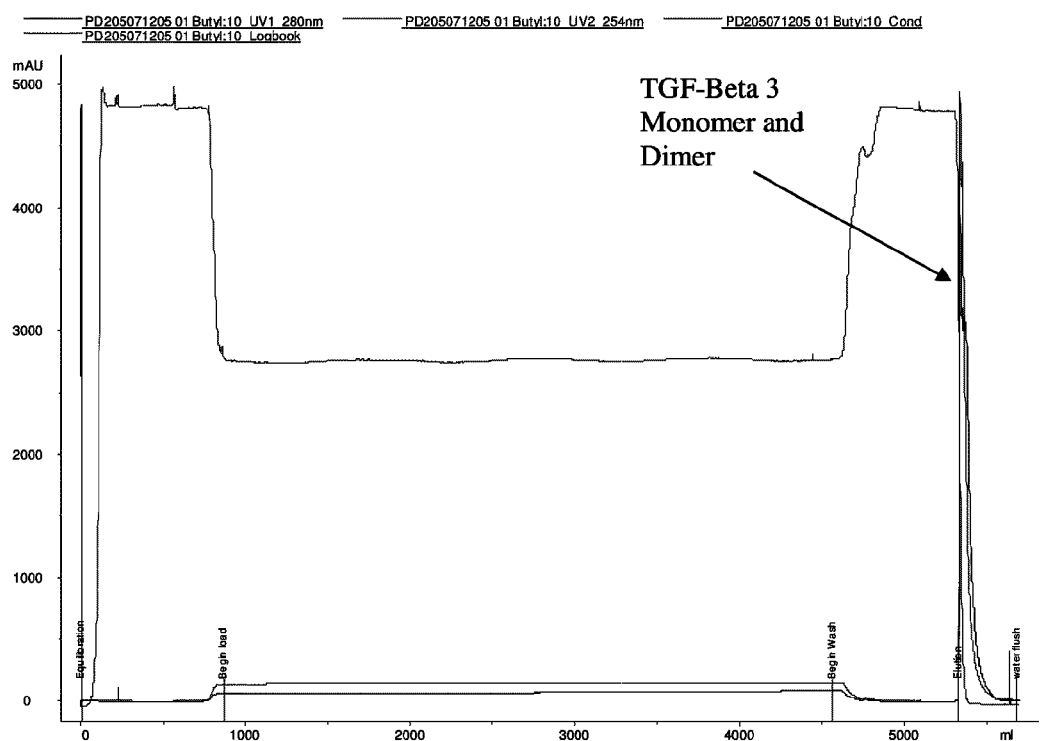
Figure 9:
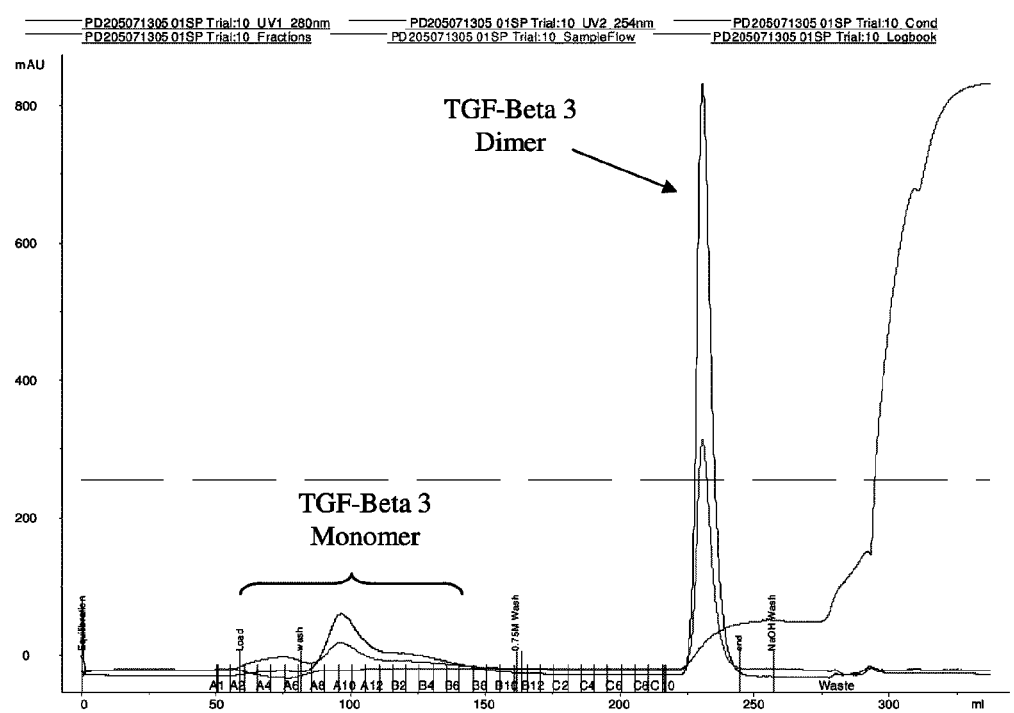

FIG. 8: represents a chromatogram illustrating the amount of monomeric and dimeric TGF-Beta 3 produced by a most preferred refolding condition according to the invention as discussed at 1.15 of Example 1 after purification by ultrafiltration and hydrophobic interaction chromatography on a Butyl-Sepharose column;

FIG. 9: represents a chromatogram illustrating the amount of dimeric TGF-Beta 3 produced by a most preferred refolding condition according to the invention as discussed at 1.16 of Example 1 after purification by cation exchange chromatography on a SP-Sepharose column;

FIG. 10: is a schematic flow diagram illustrating a preferred method according to the second aspect of the invention in which: (A) represents the fermentation and Inclusion Body (IB) recovery step; (B) represents the LB solubilization and clarification step; (C) represents a refold step according to the first aspect of the invention; (D) represents a purification step; and (E) represents a step for formulation and file of the drug product.

Figure 11:
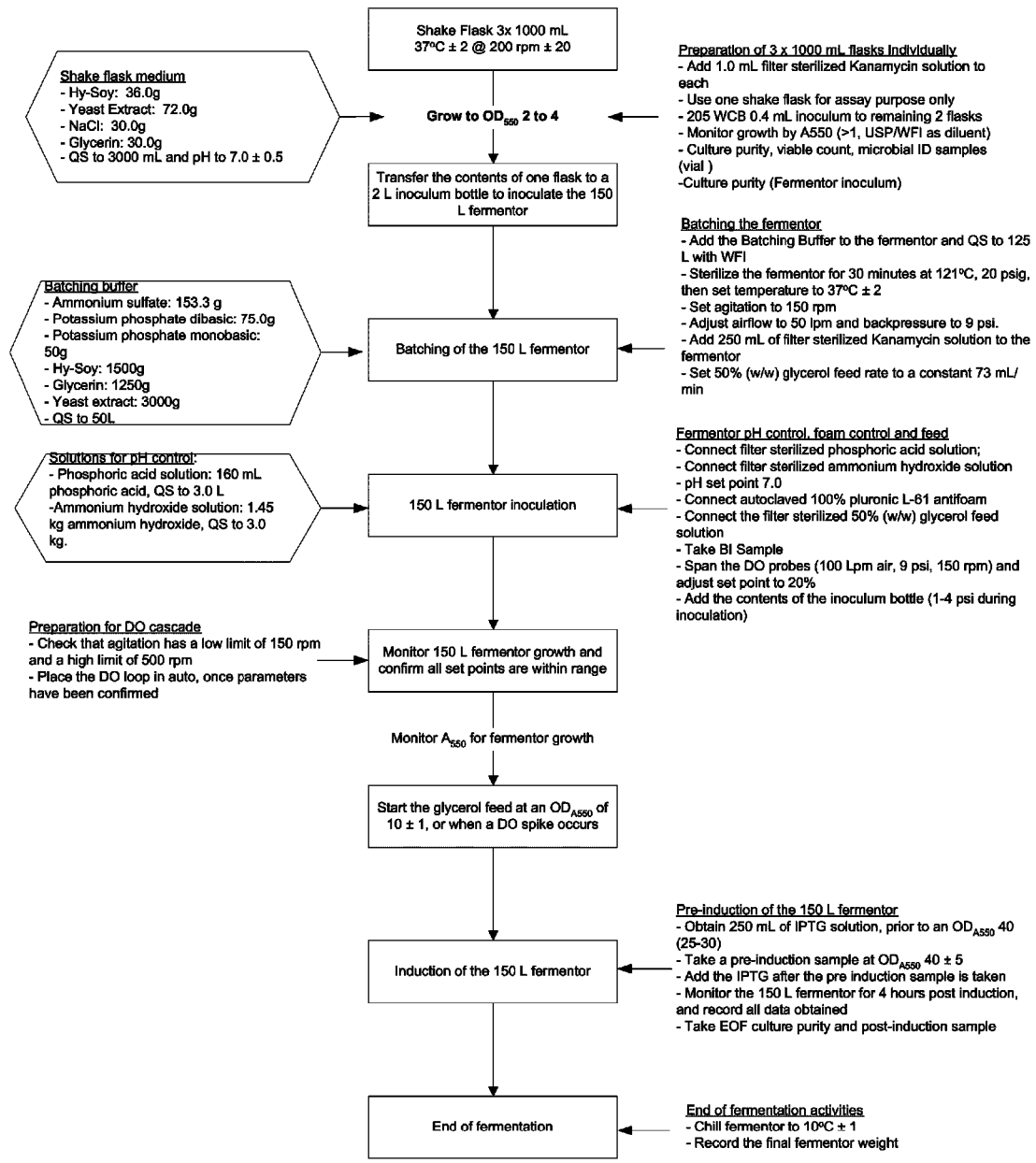
Figure 12:
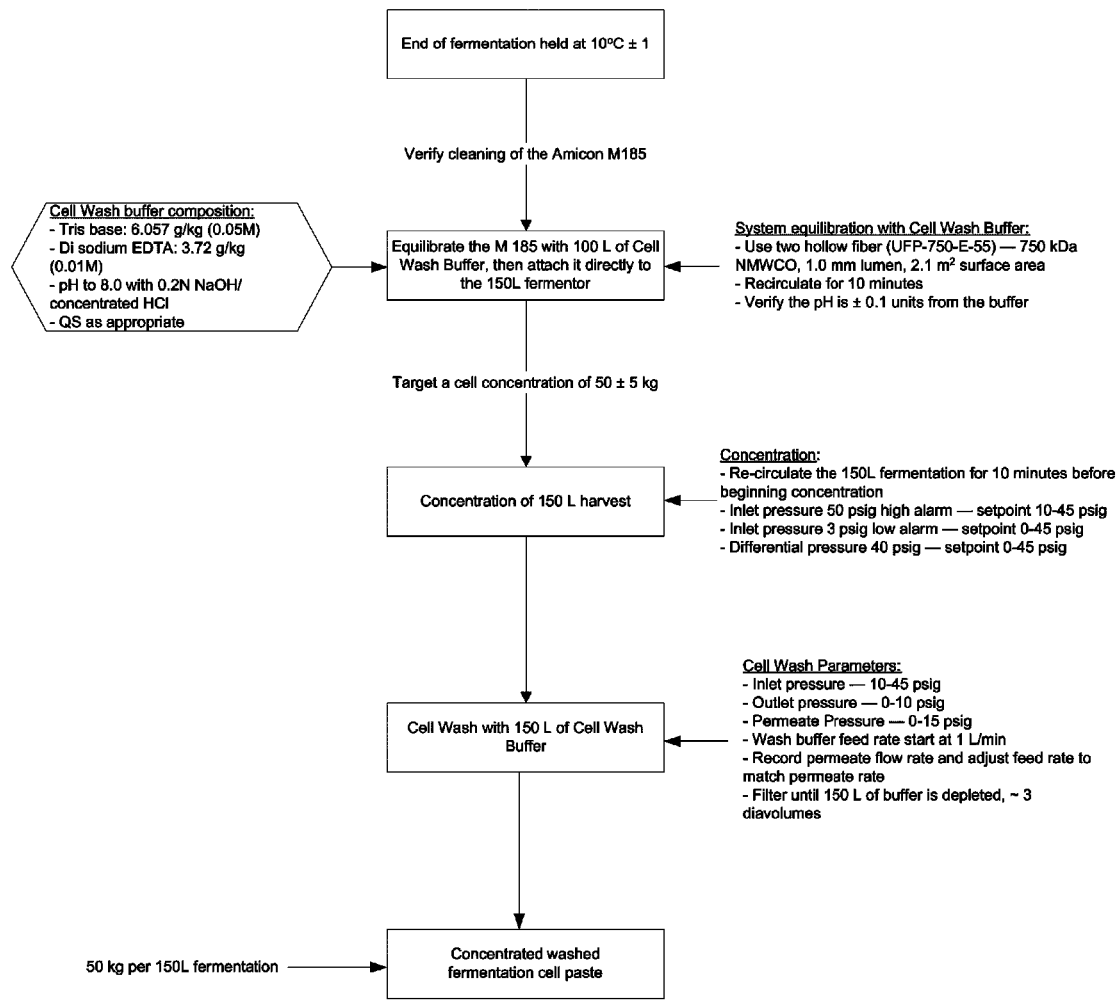
Figure 13:
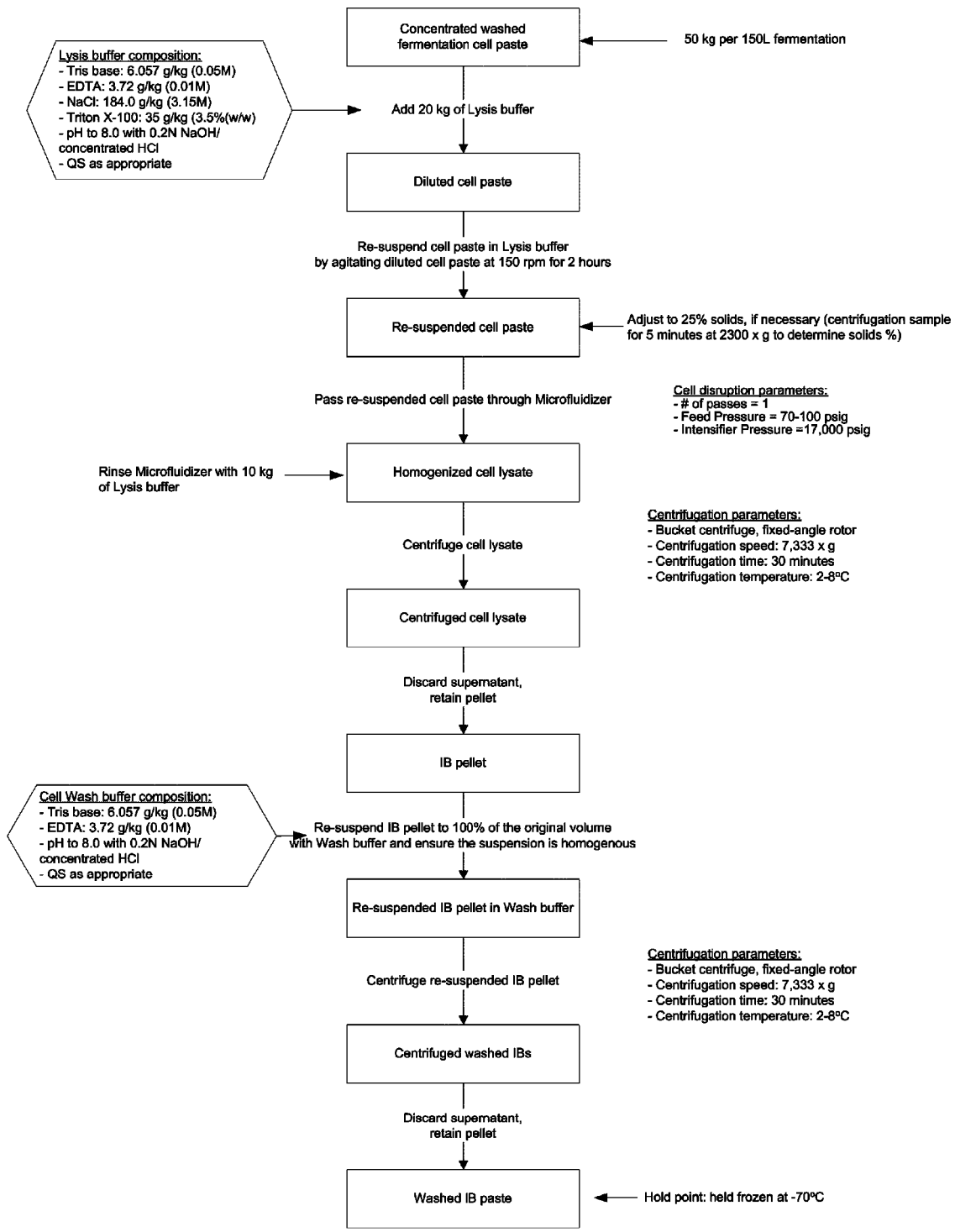
Figure 14:
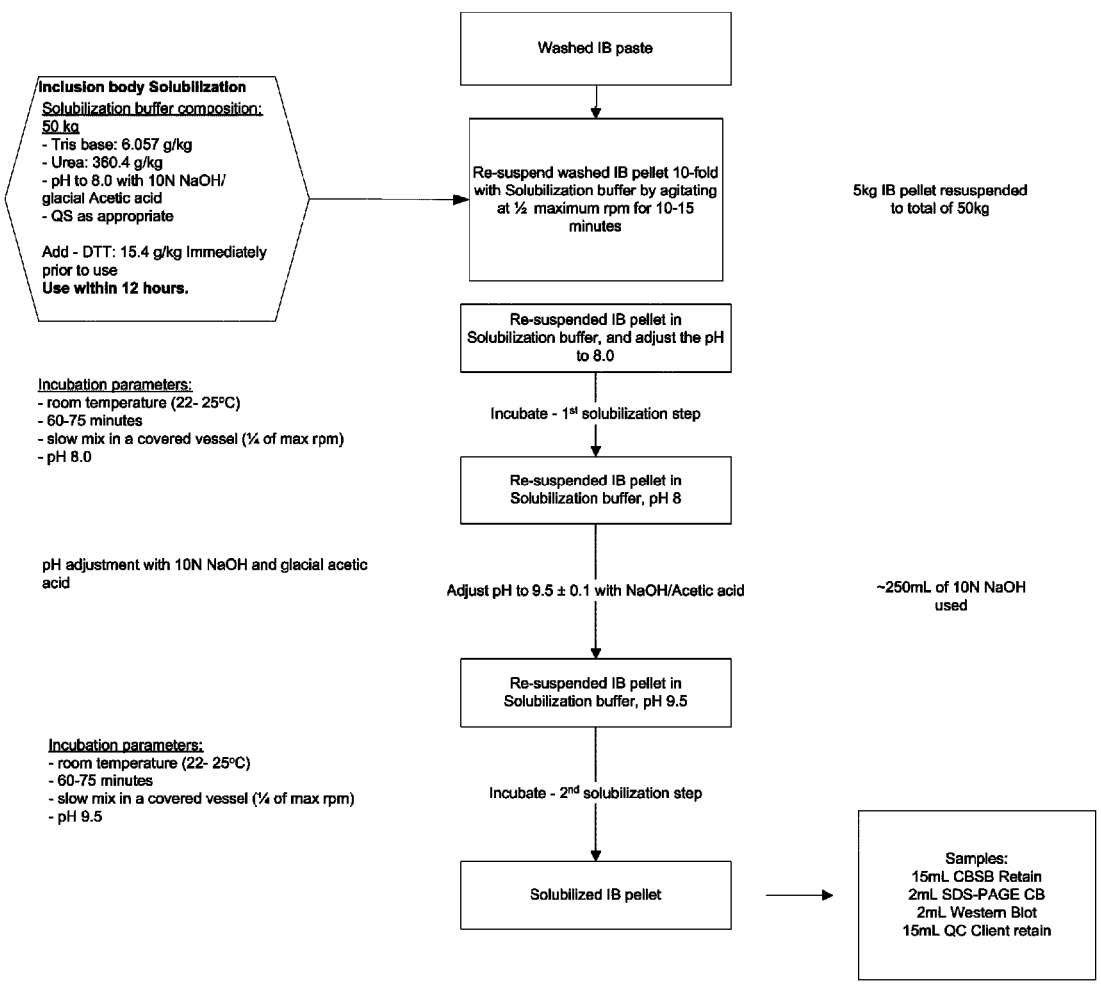
Figure 16A:
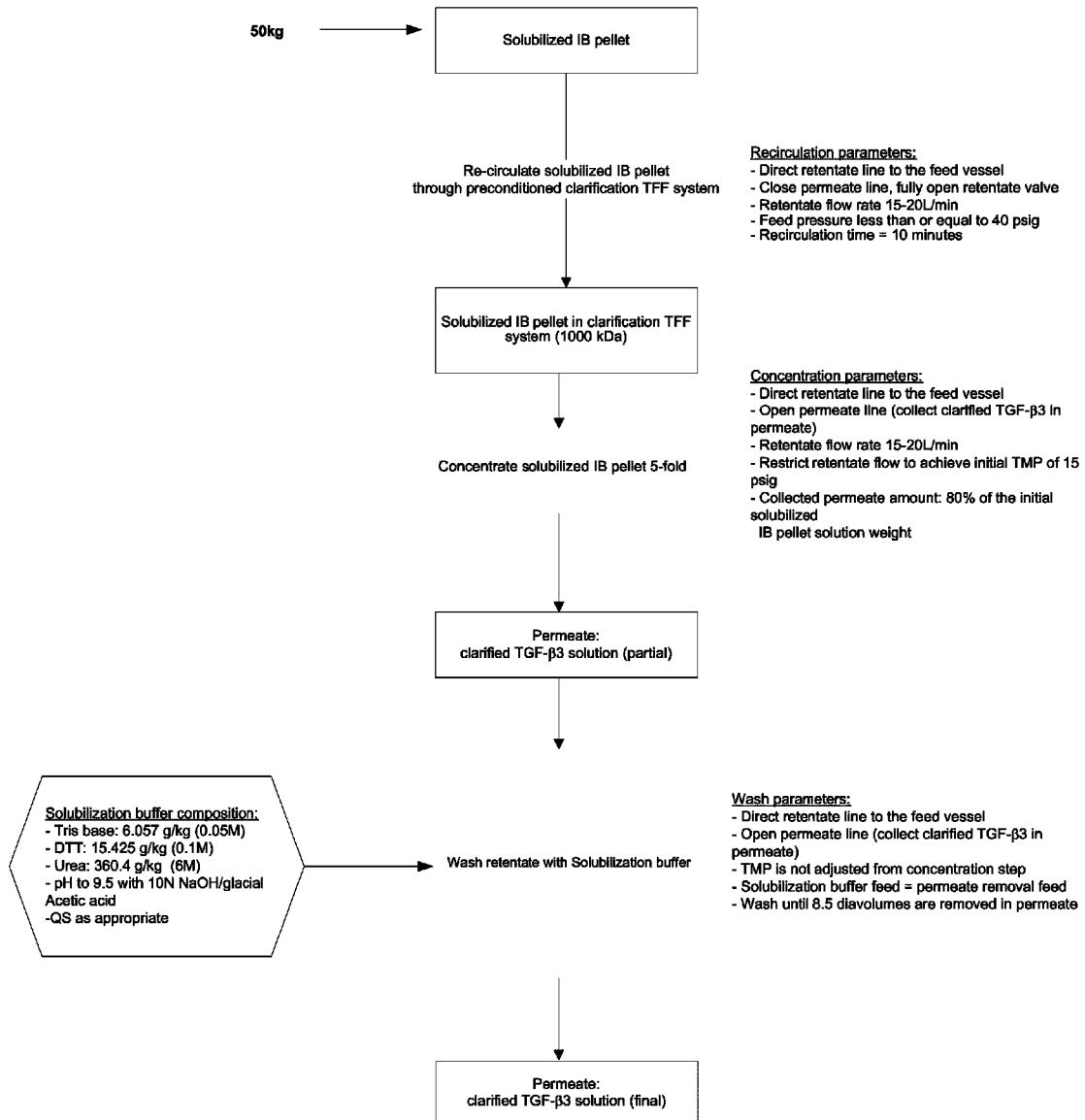
Figure 16B:
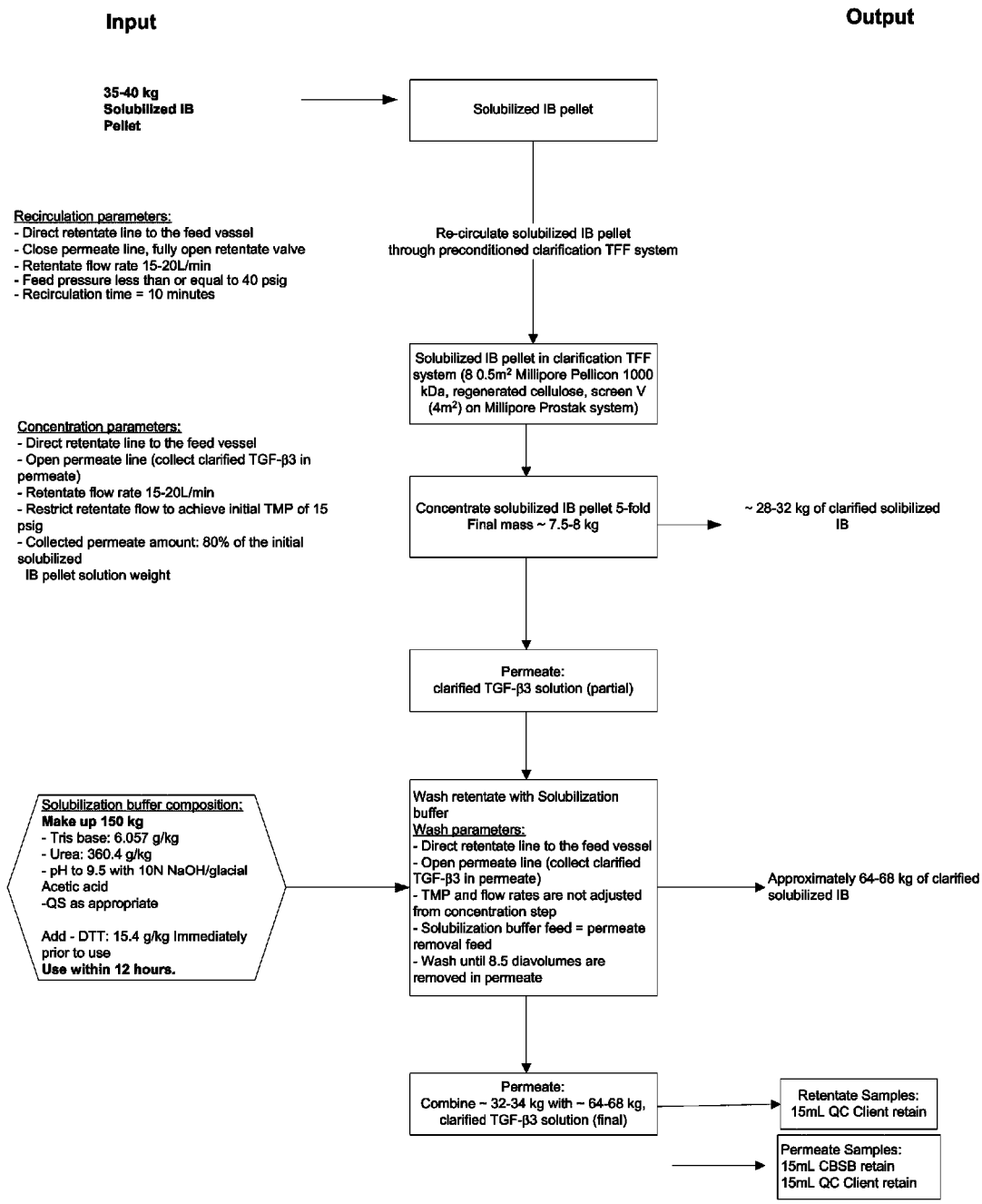
Figure 17A:
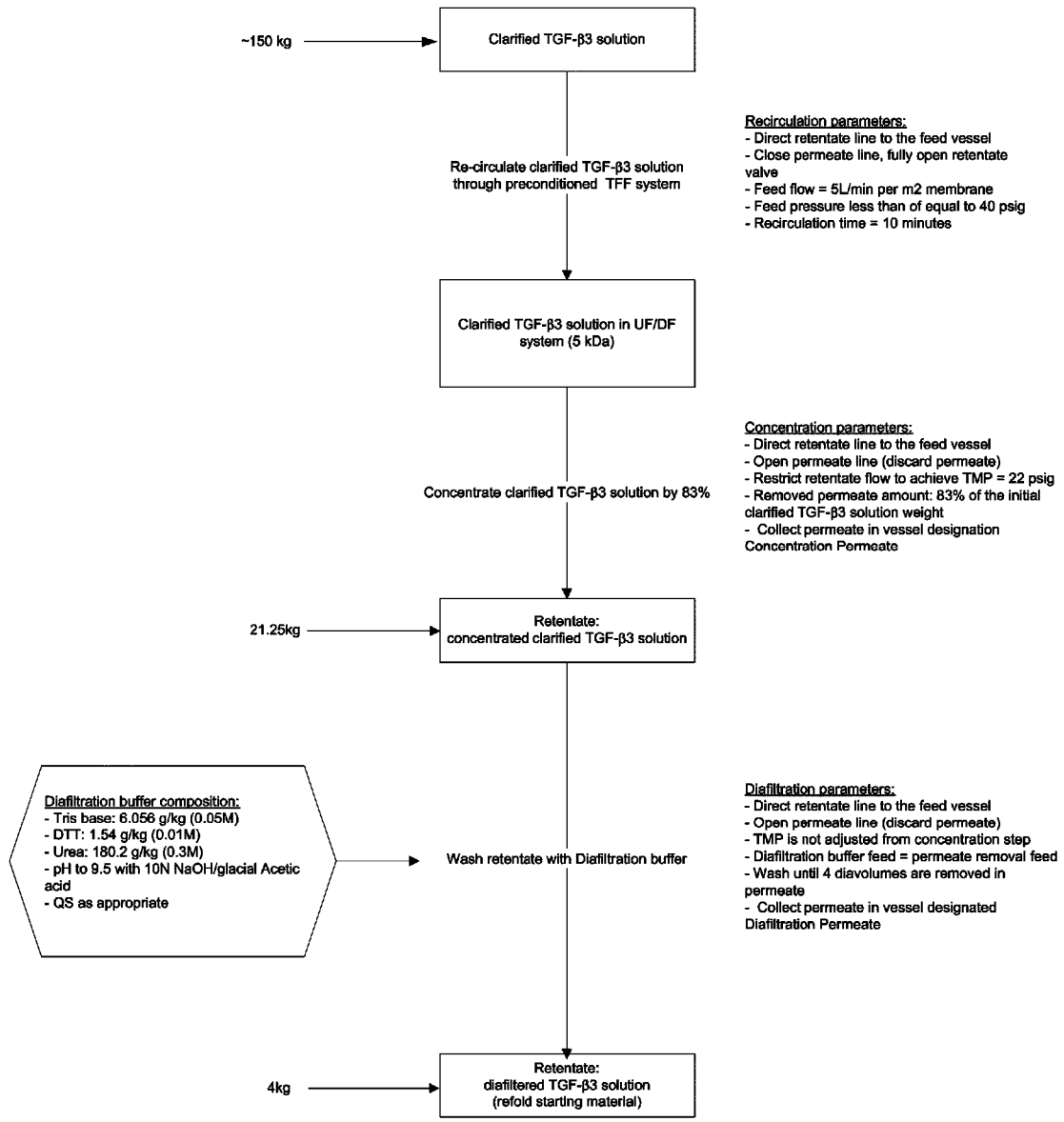
Figure 17B:
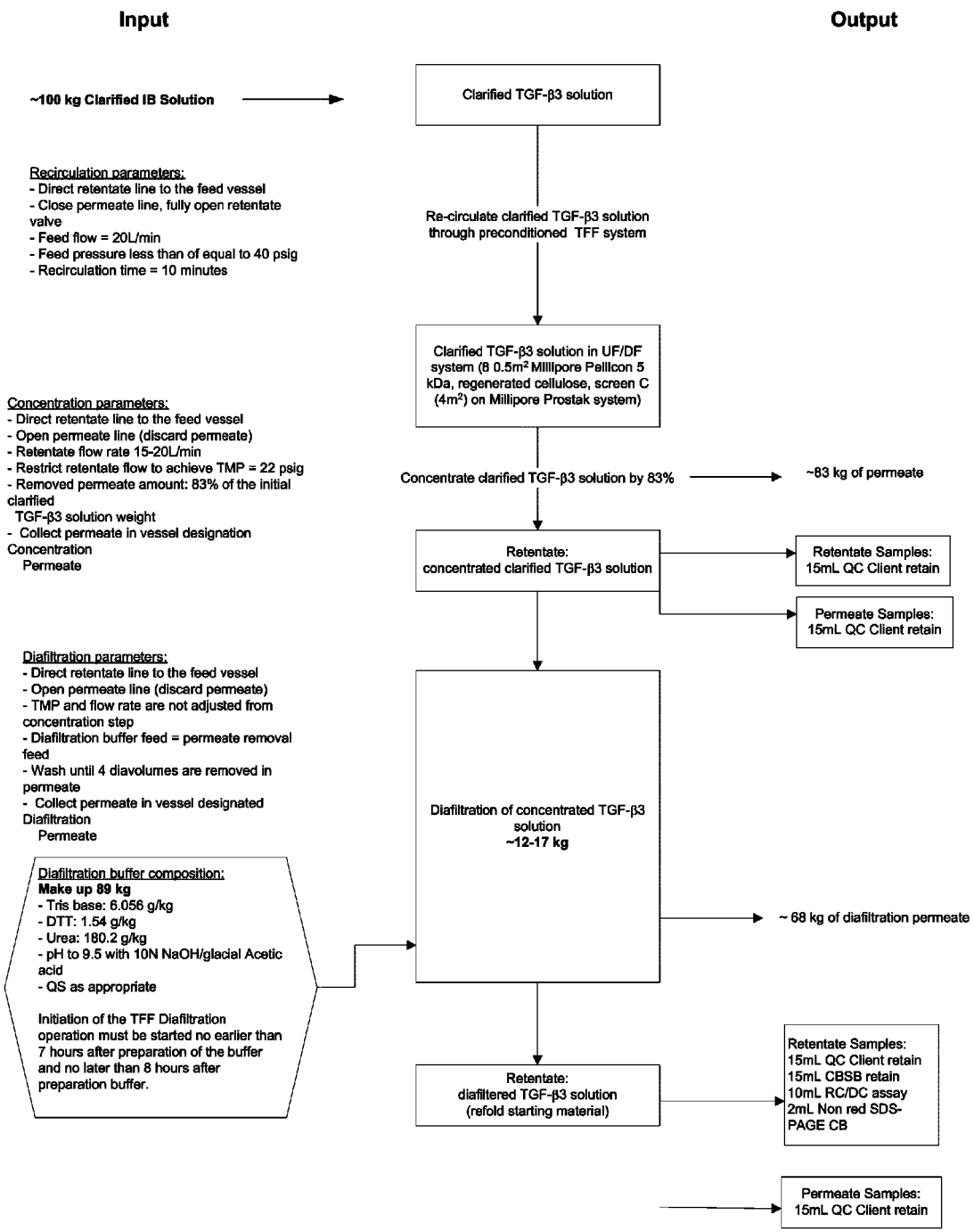
Figure 18A:
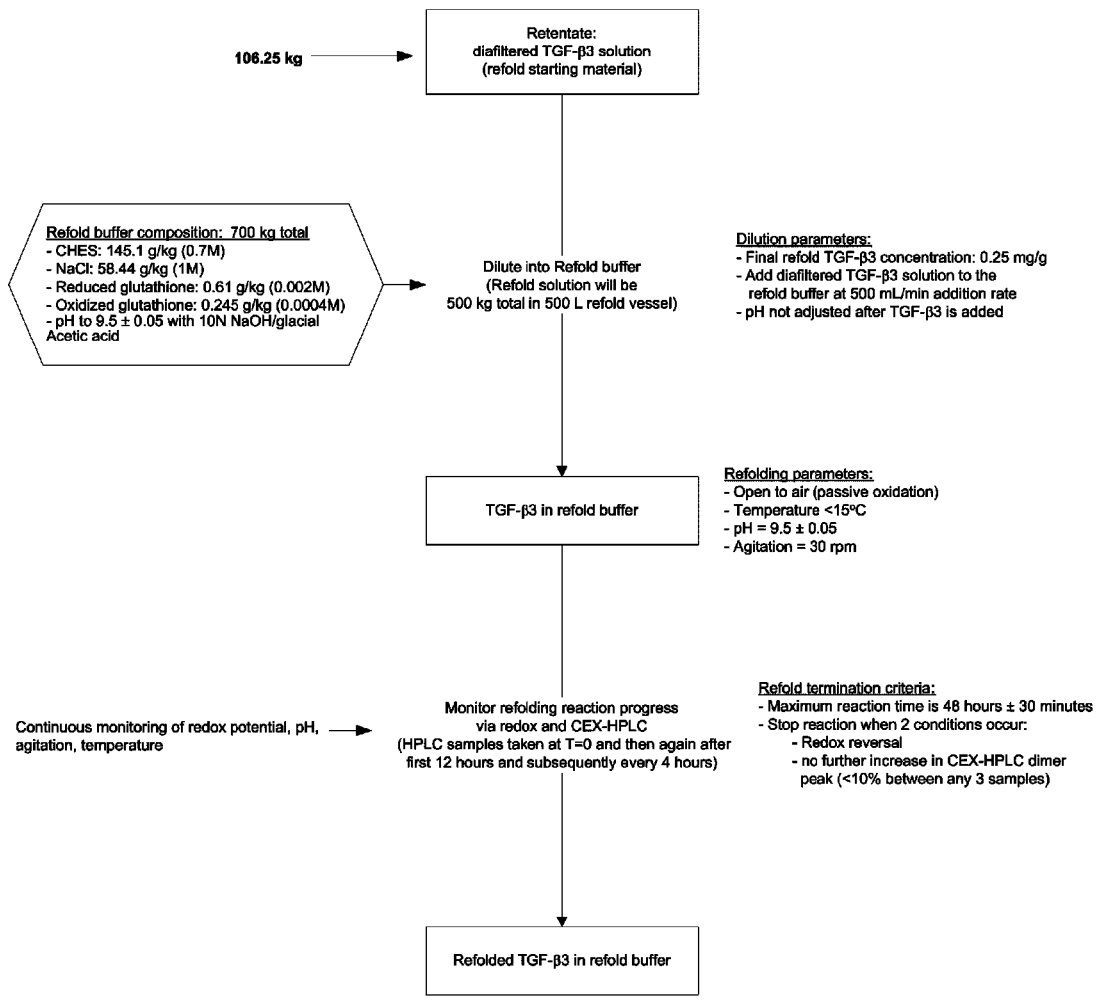
Figure 18B:
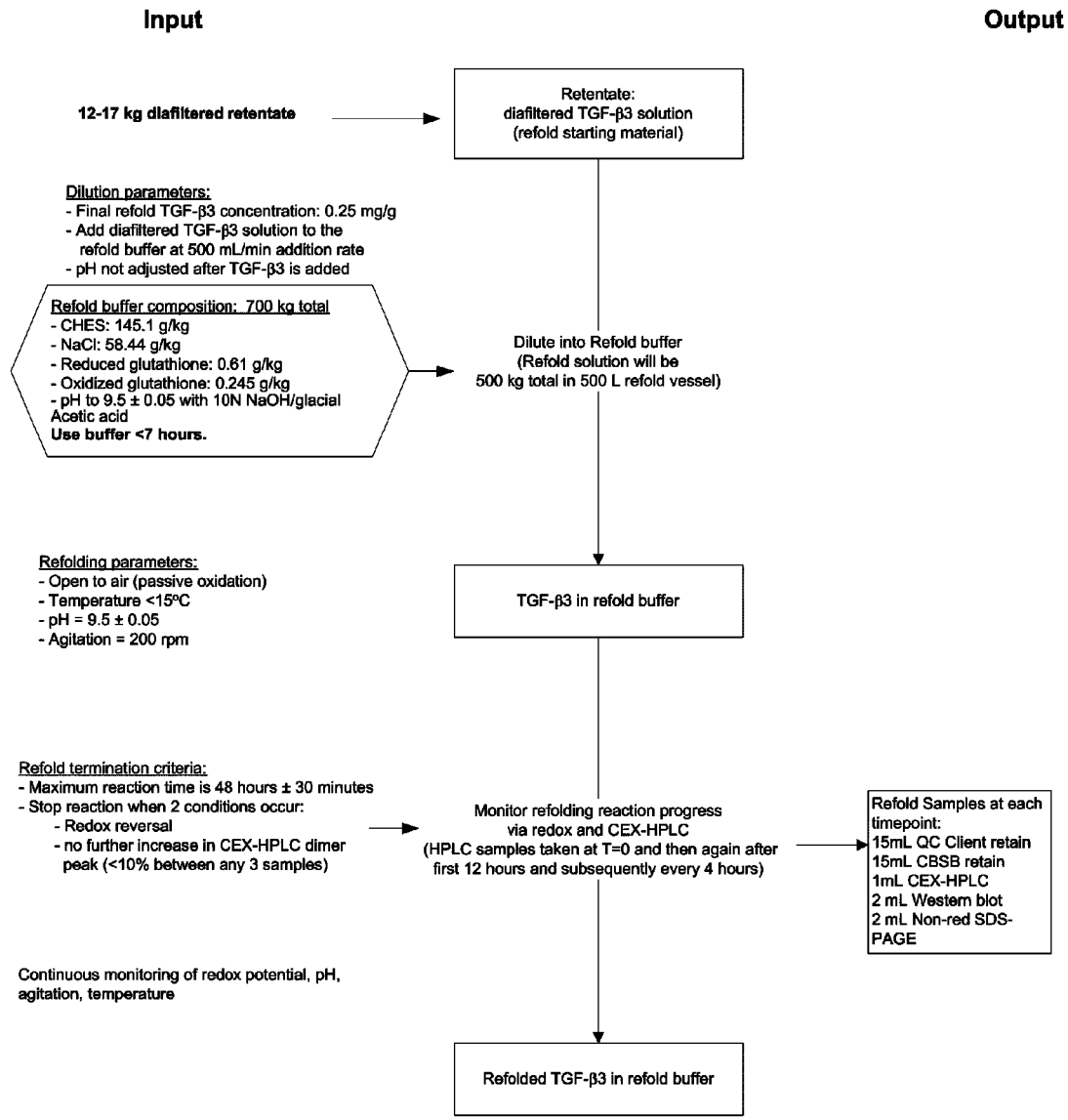
Figure 19:
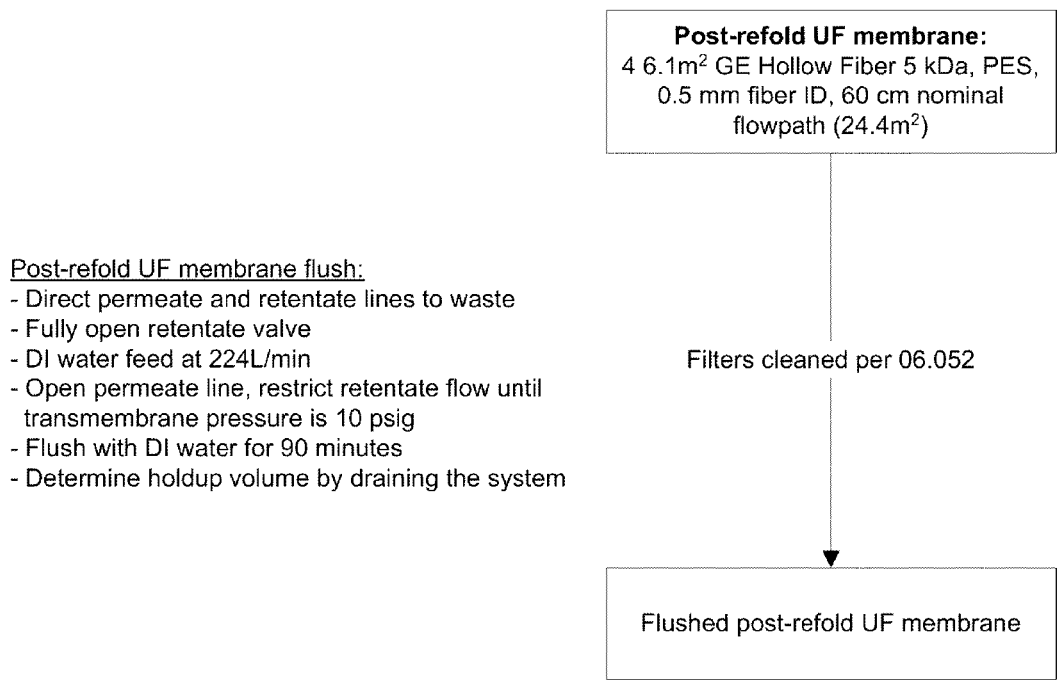
Figure 20A:
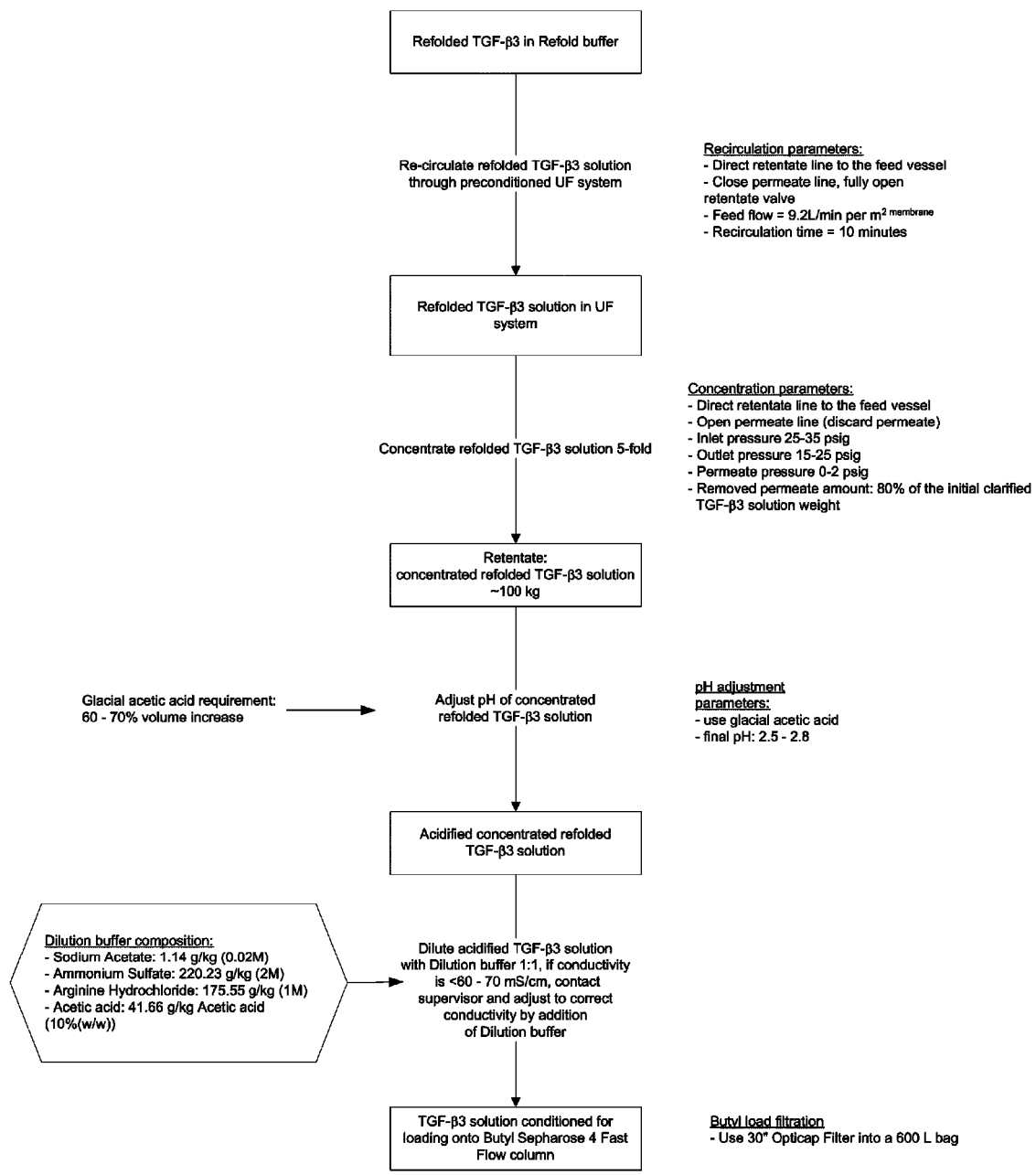
Figure 20B:
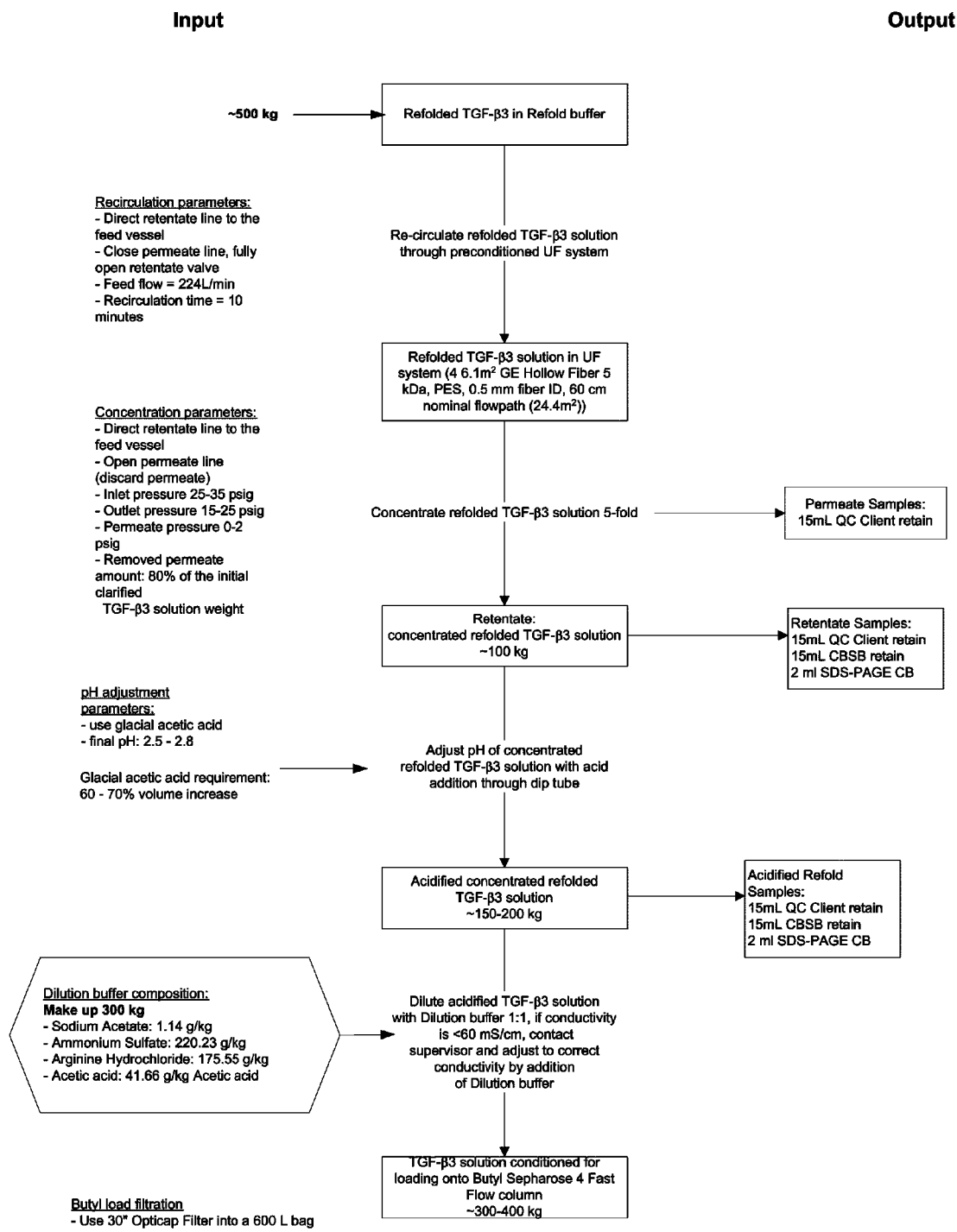
Figure 21A:
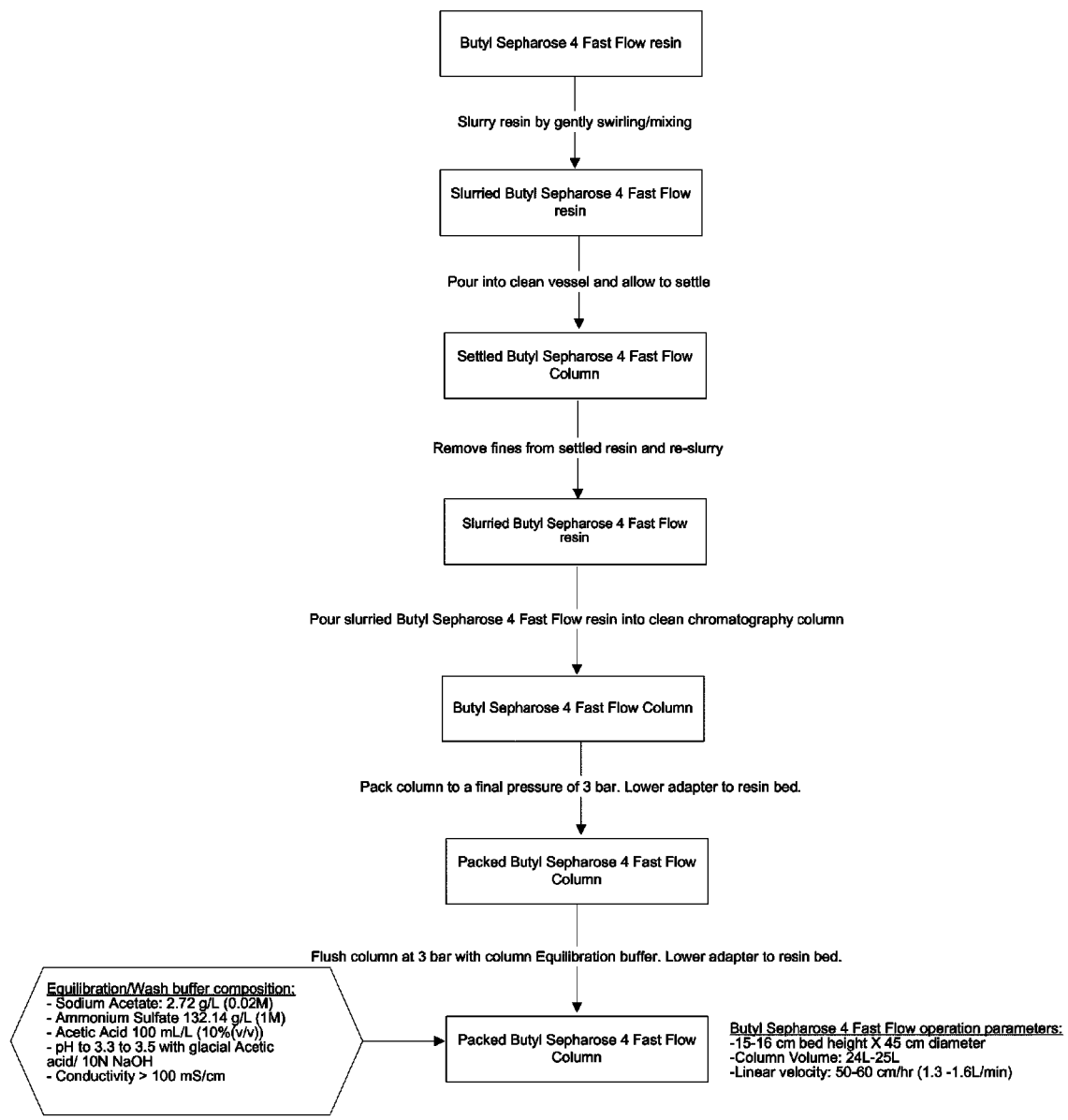
Figure 21B:
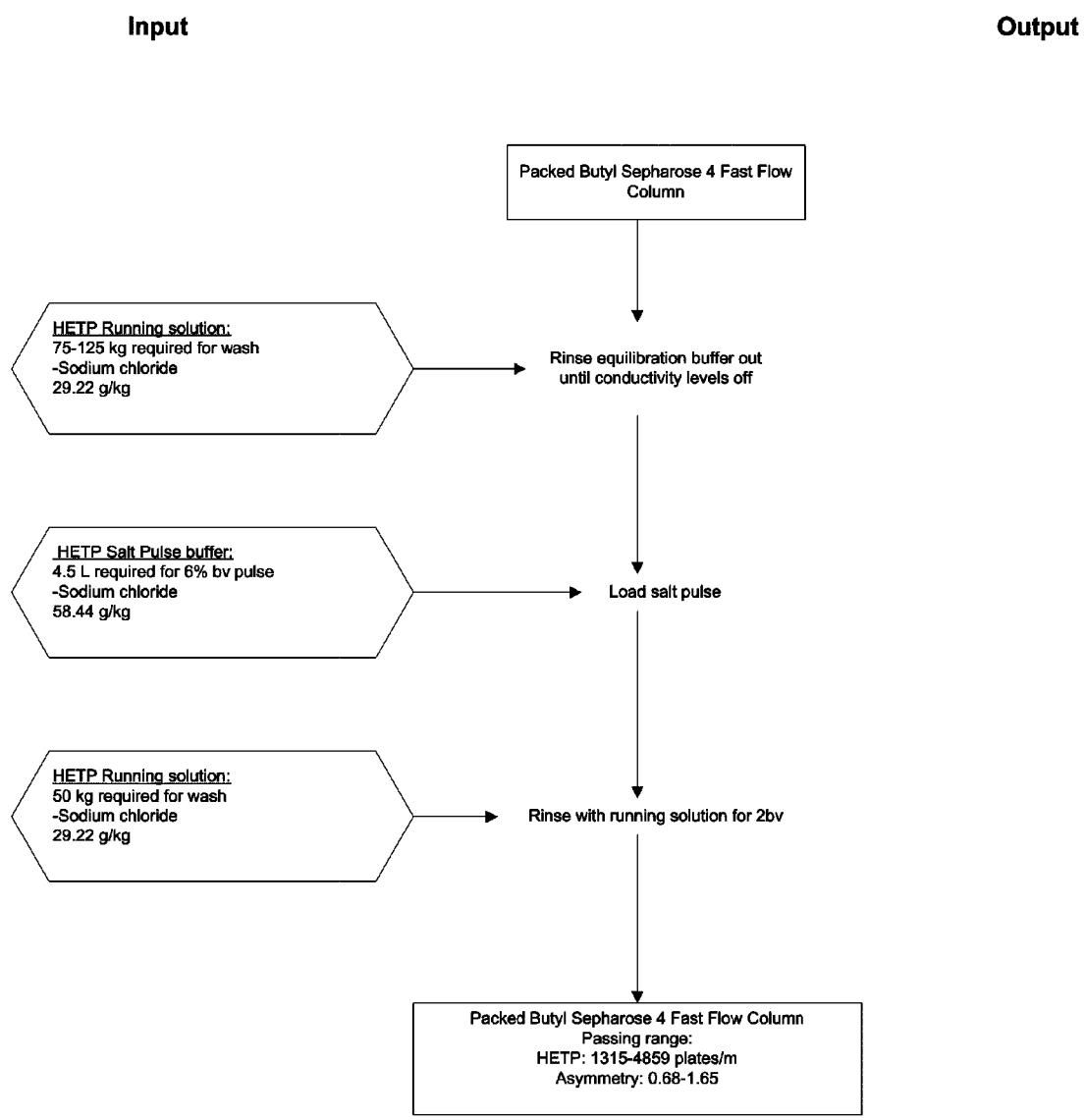
Figure 22B:
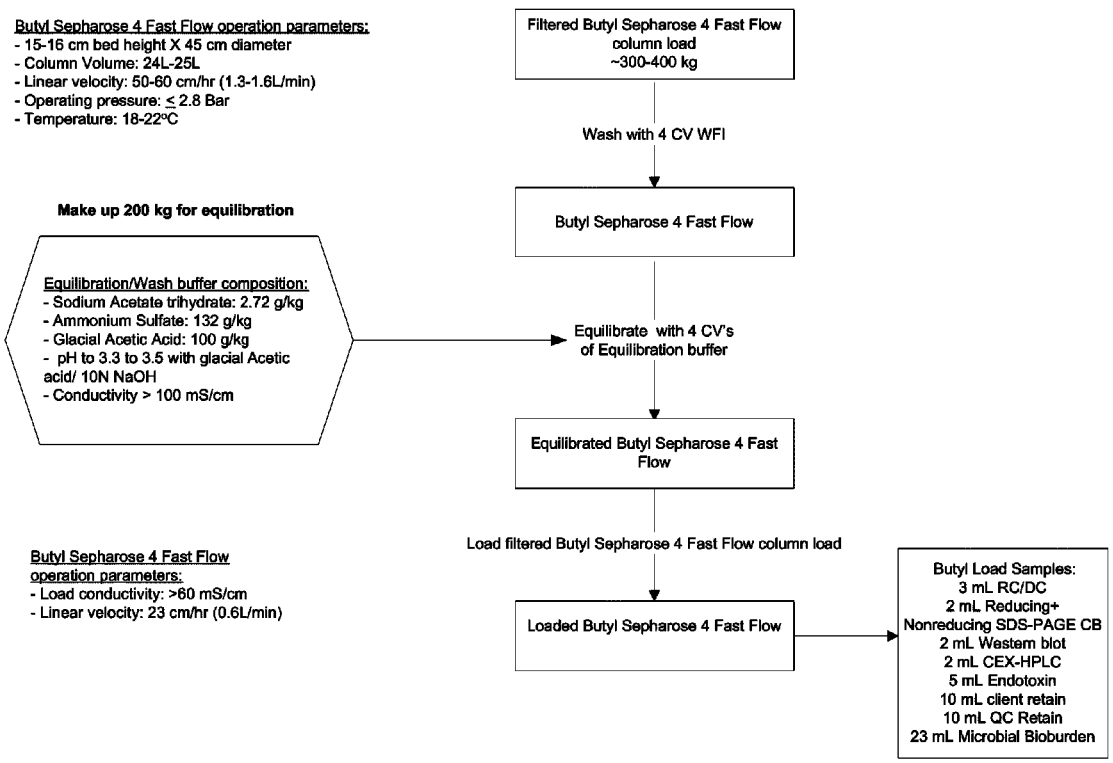
Figure 22B:
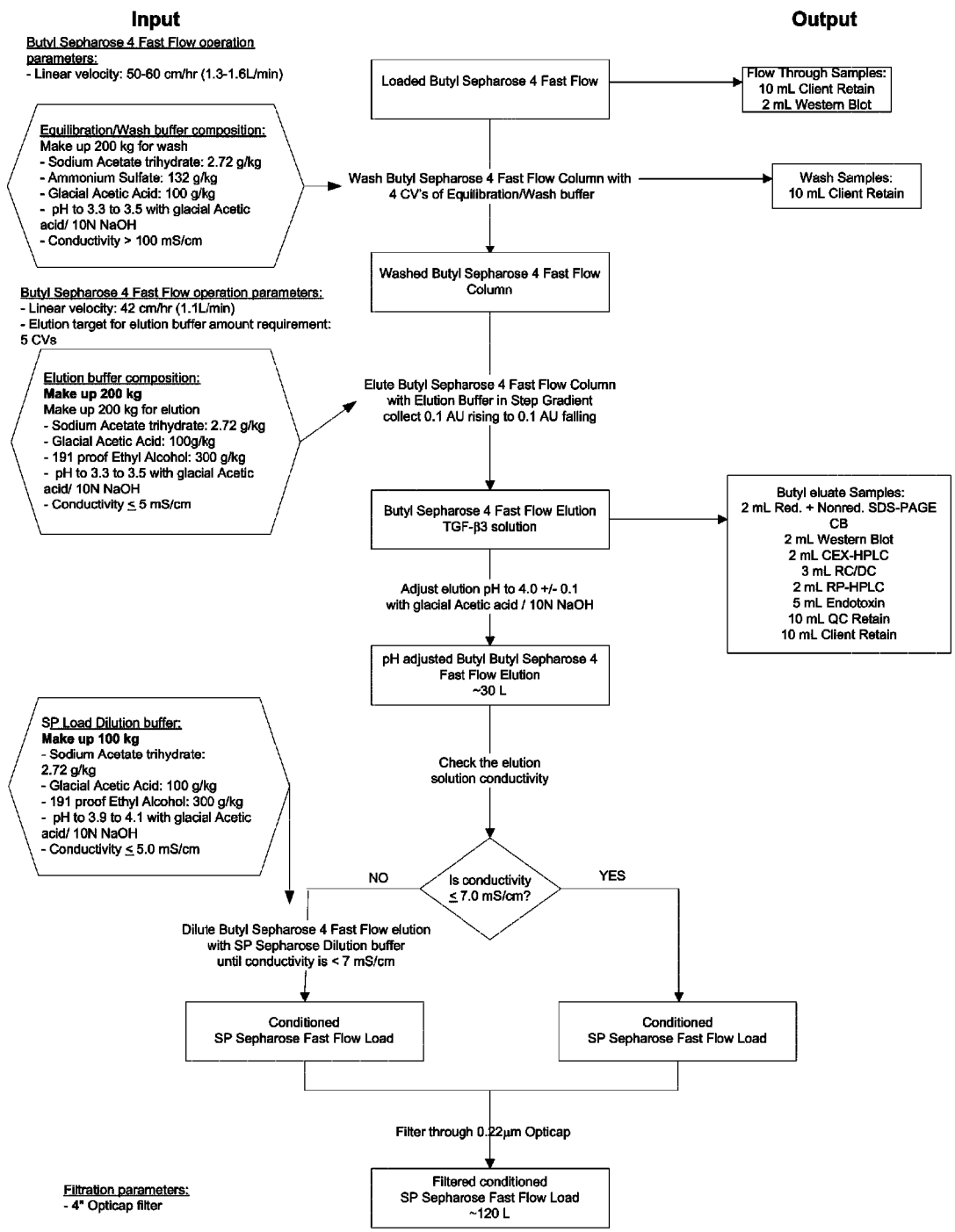
Figure 24:
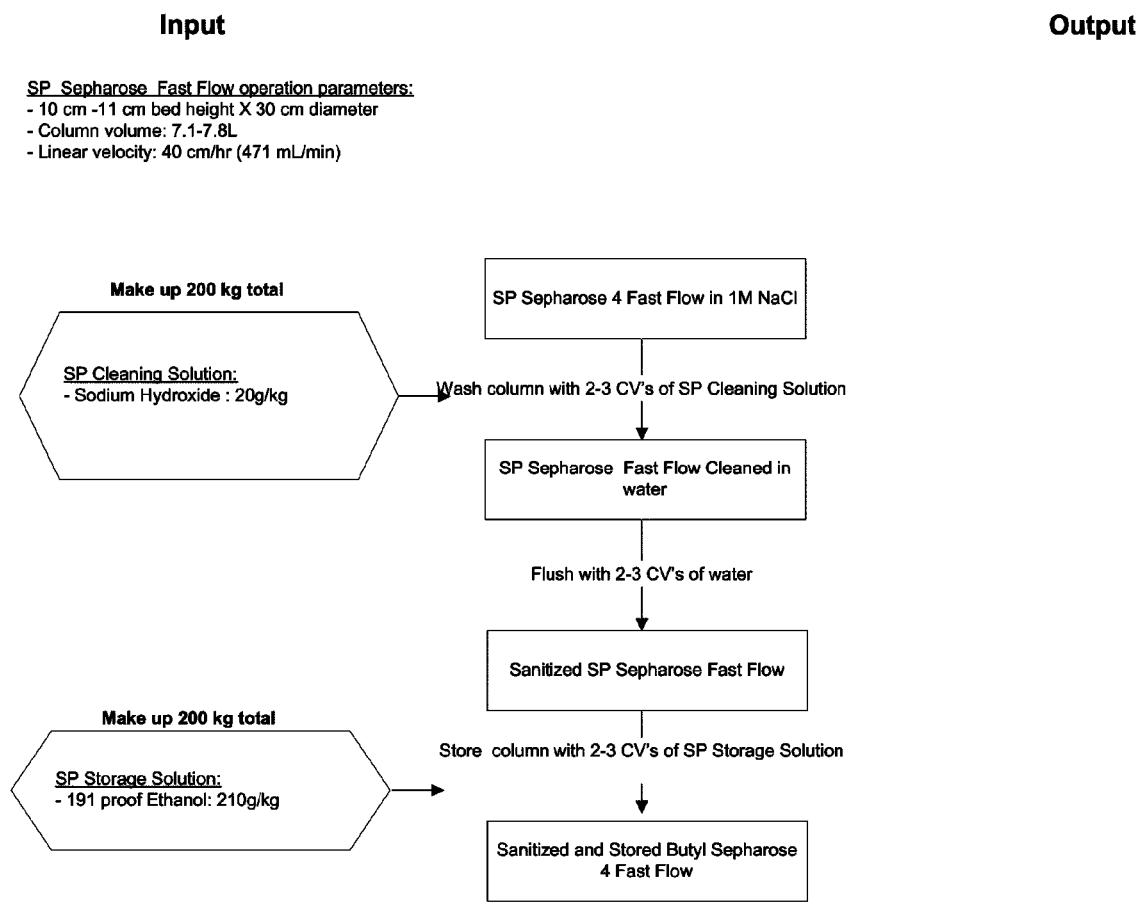
Figure 25:
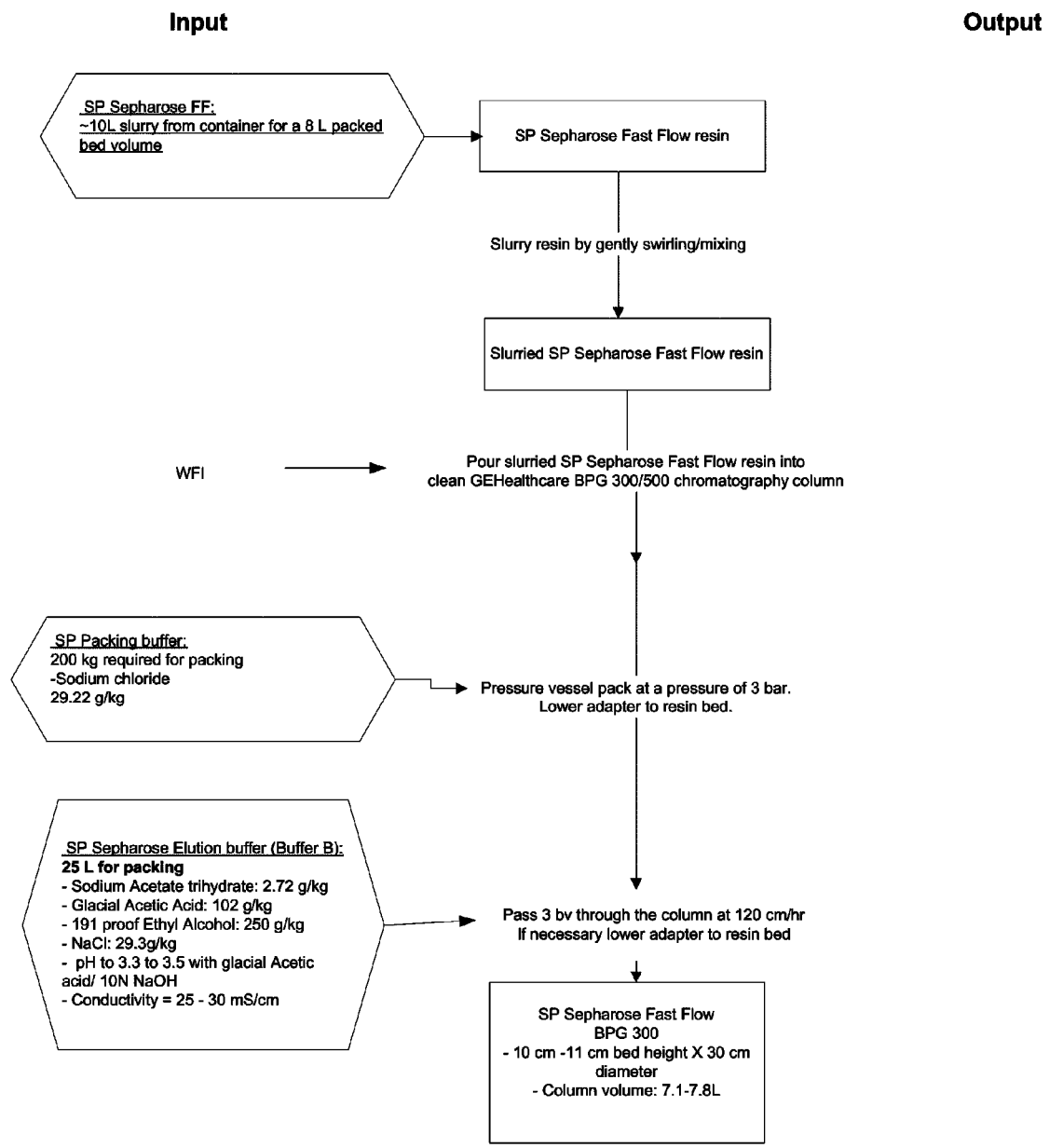
Figure 25:
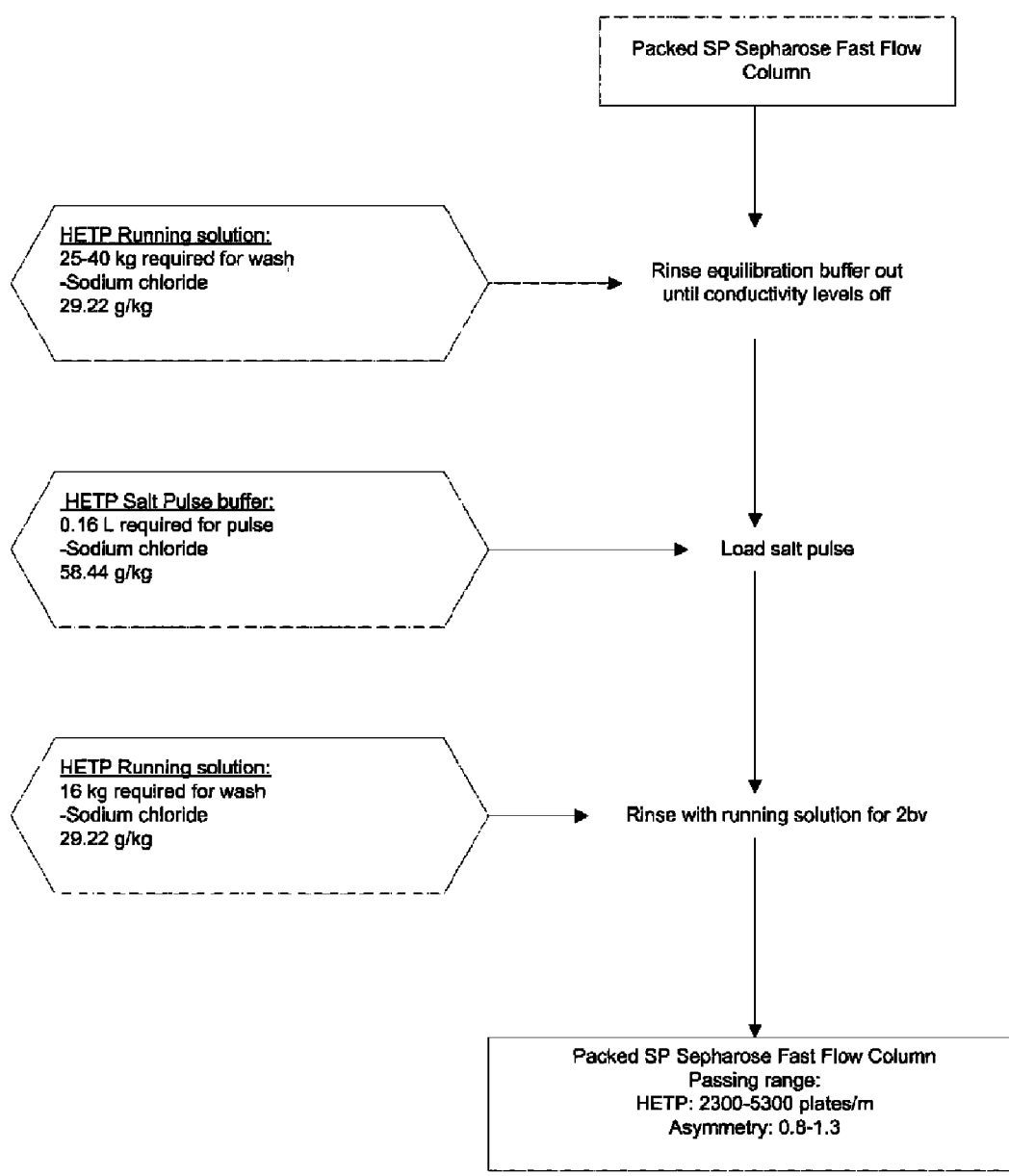
Figure 26A:
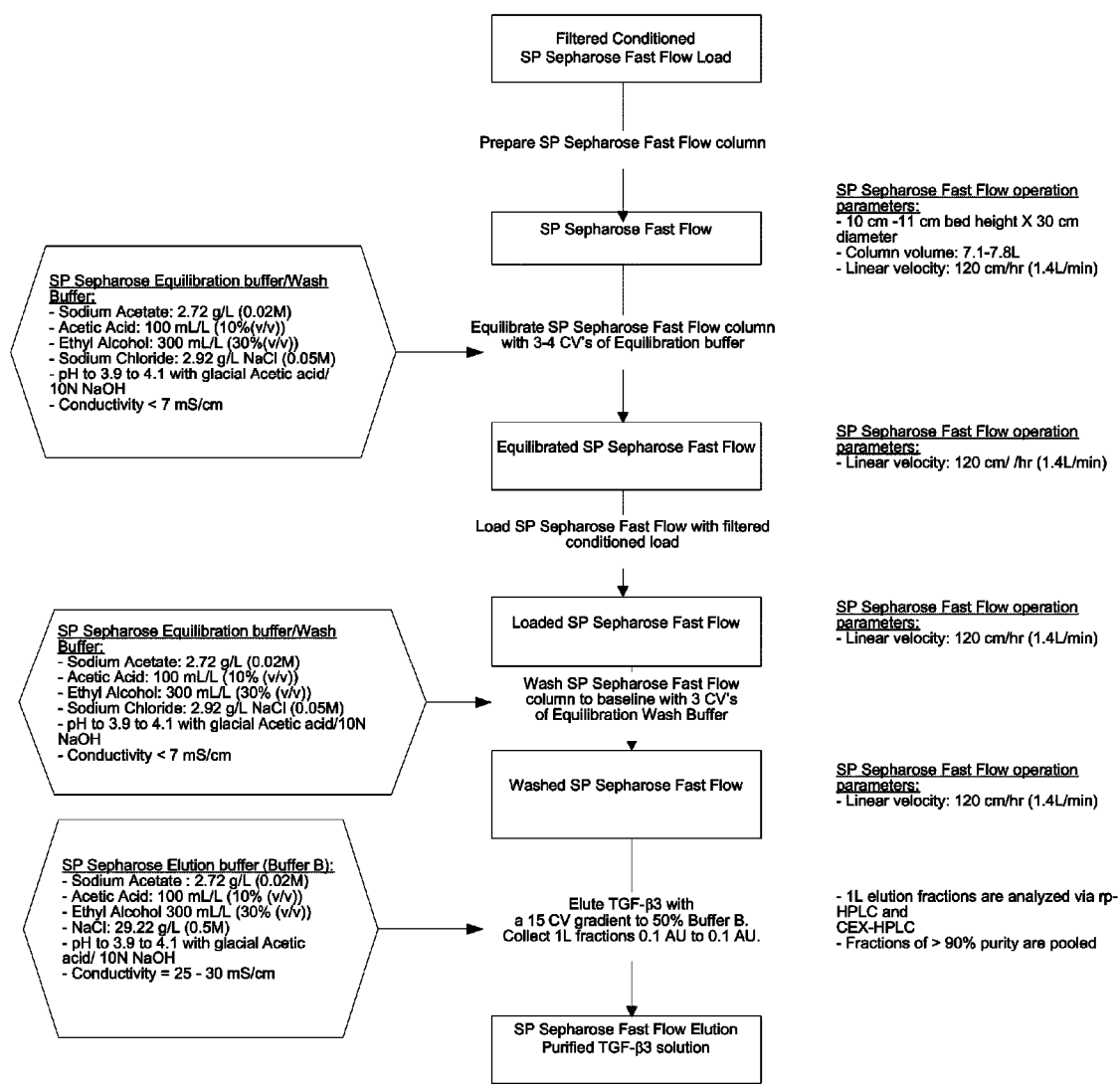
Figure 26B:
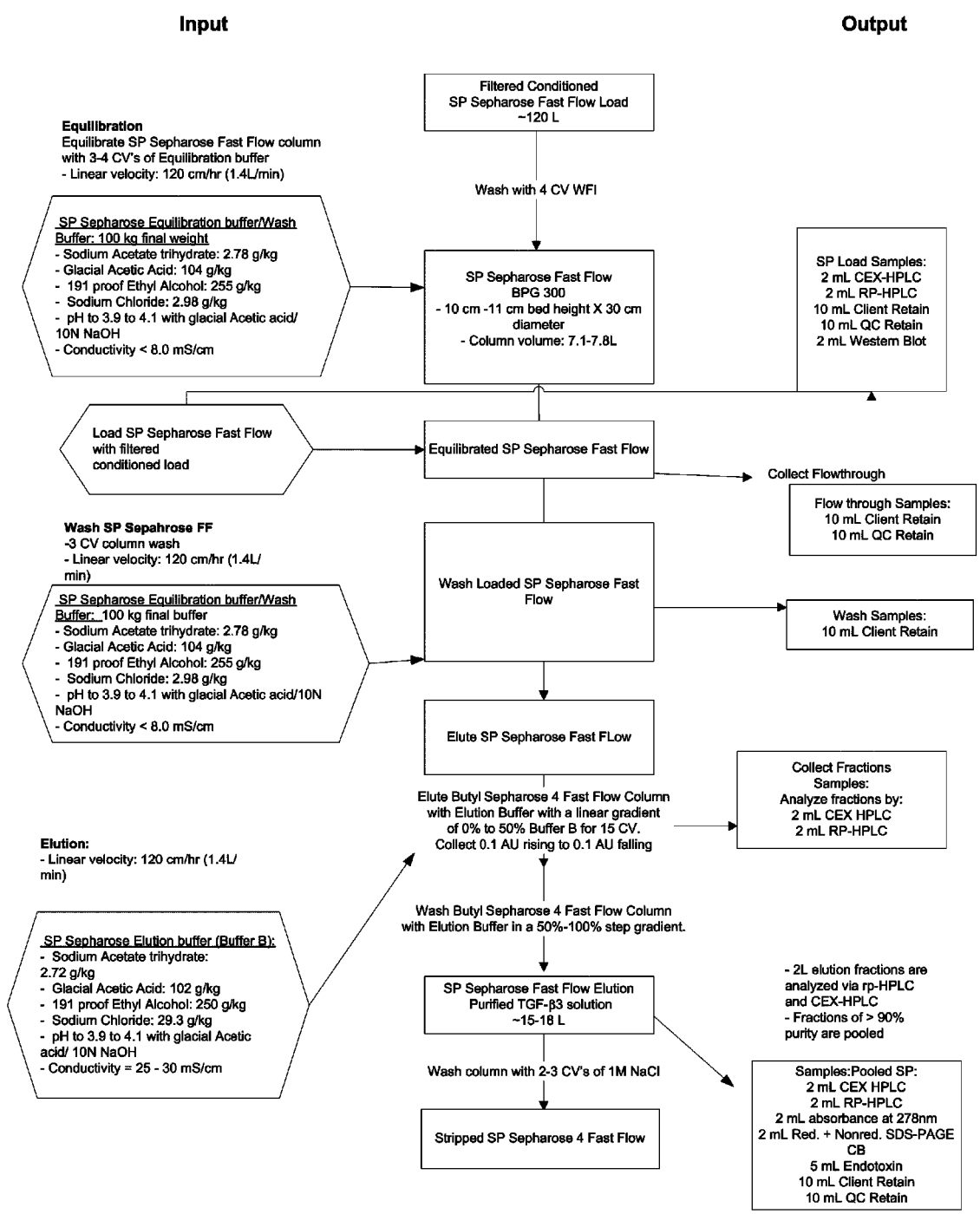
Figure 27:
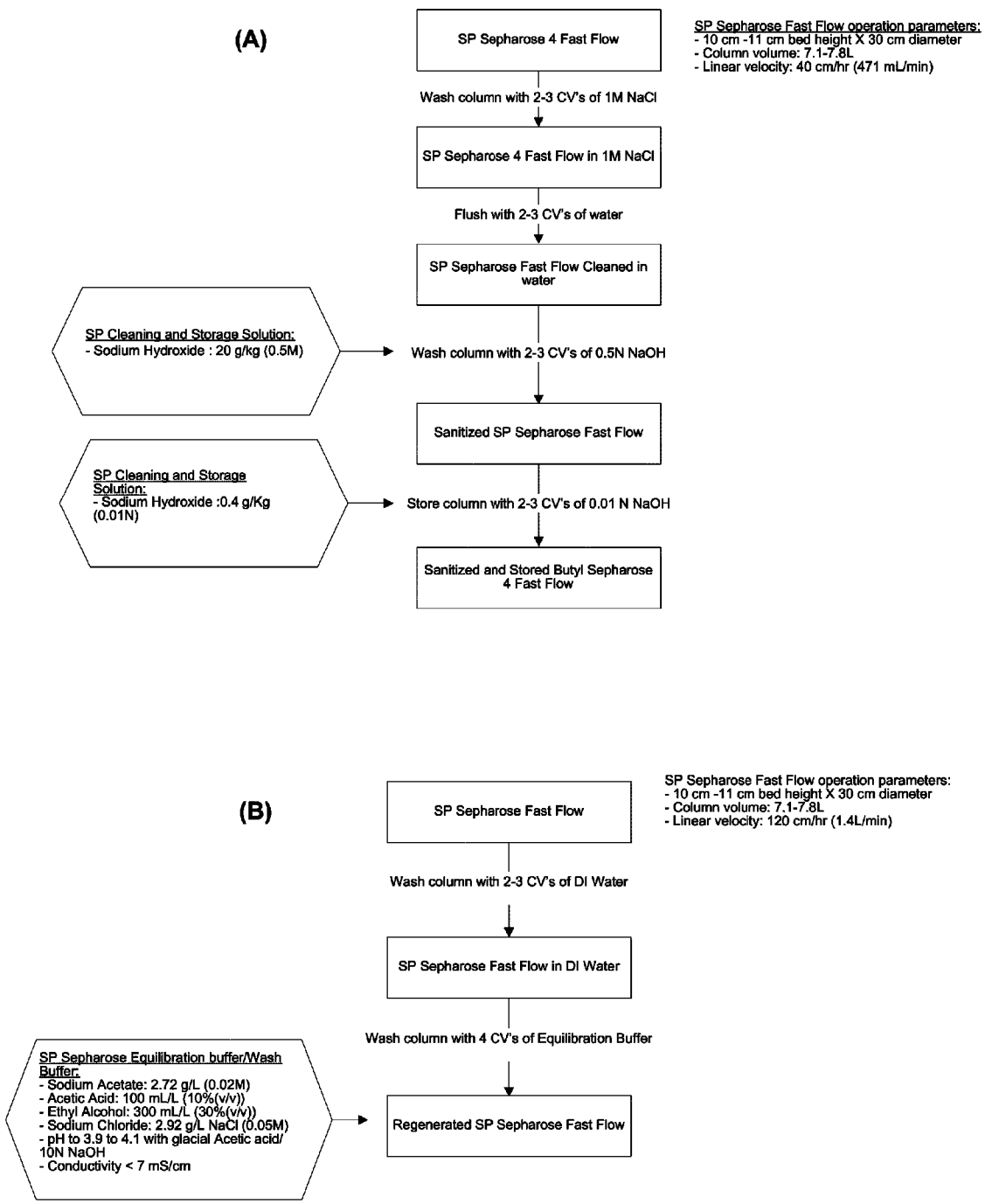
Figure 28A:
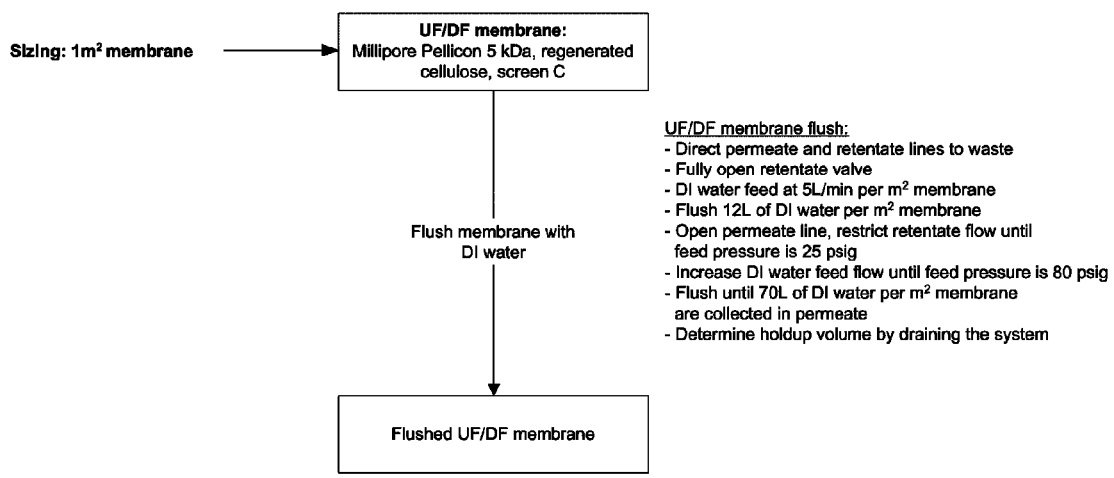
Figure 28B:
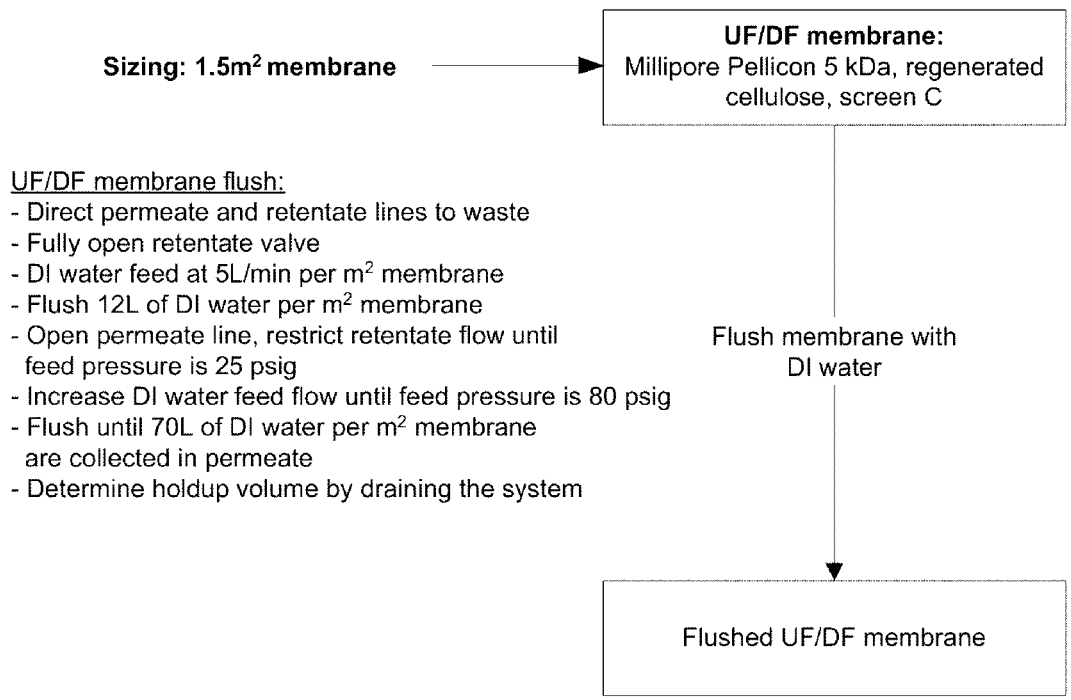
Figure 29A:
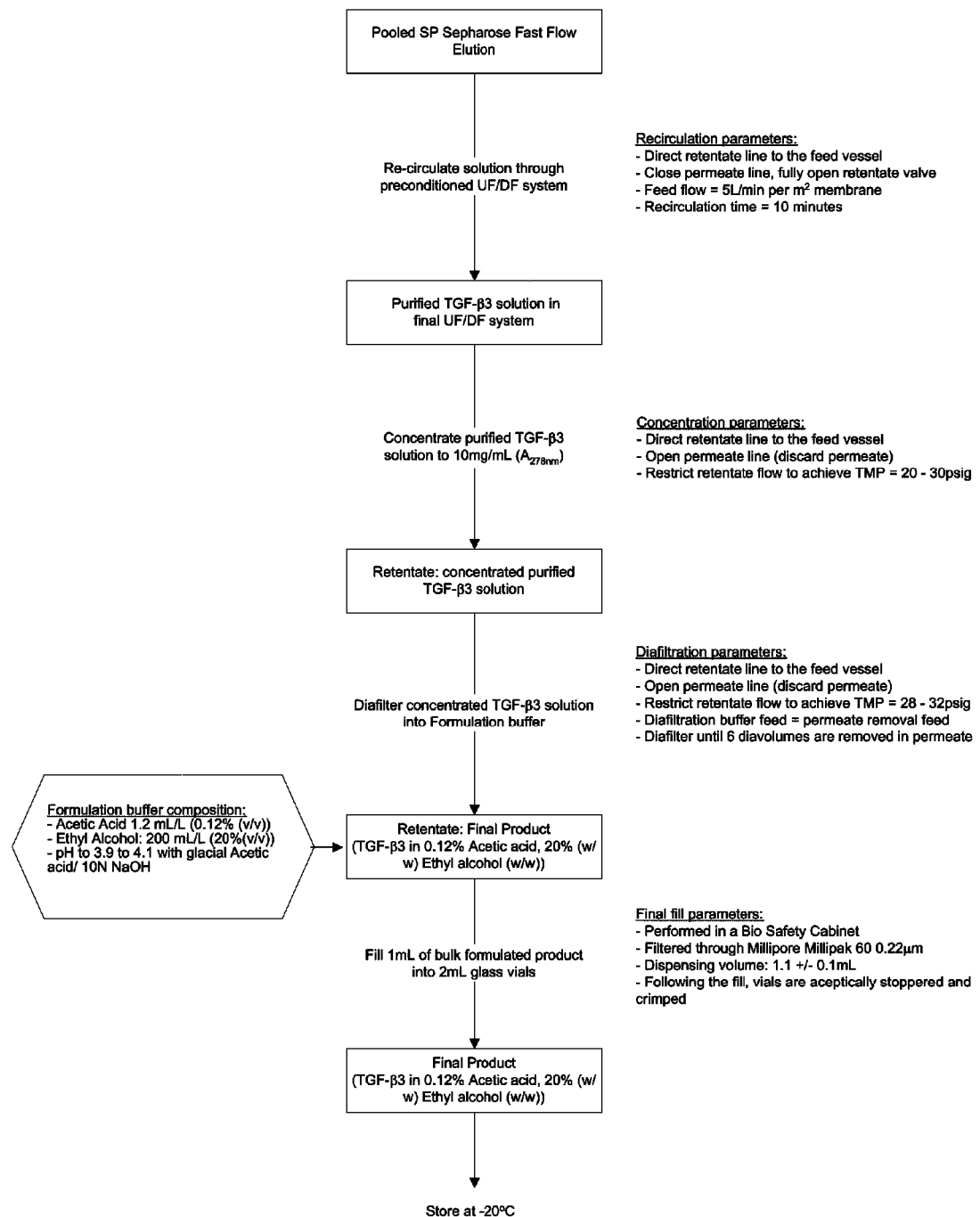
Figure 29B:
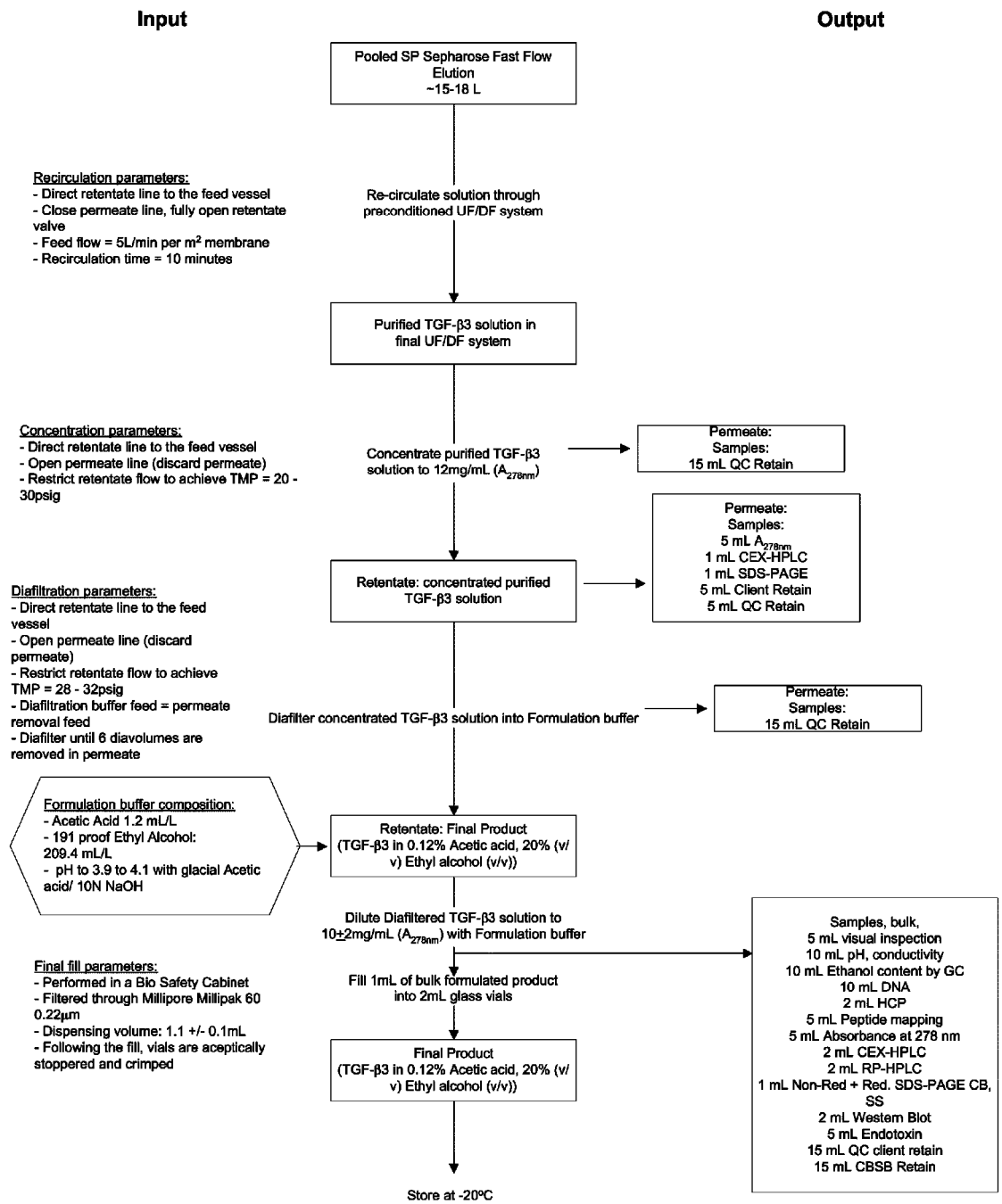

FIG. 11: illustrates preferred conditions and protocols for fermentation suitable for use in methods of the invention such as that set out in FIG. 10(A) (i);

FIG. 12: illustrates preferred conditions and protocols for harvest and centrifugation suitable for use in methods of the invention such as that set out in FIG. 10(A) (ii);

FIG. 13: illustrates preferred conditions and protocols for cell lysis and IB recovery suitable for use in methods of the invention such as that set out in FIG. 10(A) (iii);

FIG. 14: illustrates preferred conditions and protocols for inclusion body solubilisation suitable for use in methods of the invention such as that set out in FIG. 10(B) (i);

FIG. 15: illustrates preferred conditions and protocols for: (A) clarification membrane preparation (FIG. 10(B) (ii)); and (B) pre-refold UF/DF membrane preparation (FIG. 10(B) (iii)) suitable for use in methods of the invention;

FIG. 16: illustrates two preferred conditions and protocols (A and B) for inclusion body clarification suitable for use in methods of the invention such as that set out in FIG. 10(B) (ii);

FIG. 17: illustrates two preferred conditions and protocols (A and B) for pre-refold UF/DF suitable for use in methods of the invention such as that set out in FIG. 10(B) (iii);

FIG. 18: illustrates two preferred conditions and protocols (A and B) for protein refolding suitable for use in methods of the invention such as that set out in FIG. 10(C) (i);

FIG. 19: illustrates preferred conditions and protocols for post-refold ultrafiltration membrane preparation suitable for use in methods of the invention such as that set out in FIG. 10(D) (i);

FIG. 20: illustrates two preferred conditions and protocols (A and B) for post-refold ultrafiltration and butyl load preparation suitable for use in methods of the invention such as that set out in FIG. 10(D) (i);

FIG. 21: illustrates two preferred conditions and protocols (A and B) for packing Butyl Sepharose 4 Fast Flow resin suitable for use in methods of the invention such as that set out in FIG. 10(D) (ii);

FIG. 22: illustrates two preferred conditions and protocols (A and B) for using Butyl Sepharose 4 Fast Flow resin in a manner suitable for use in methods of the invention such as that set out in FIG. 10(D) (ii);

FIG. 23: illustrates two preferred conditions and protocols (A and B) for cleaning and regeneration of Butyl Sepharose 4 Fast Flow resin after use in methods of the invention such as that set out in FIG. 10(D) (ii), FIG. 24: illustrates preferred conditions and protocols for cleaning SP Sepharose Fast Flow resin before use in methods of the invention as that set out in FIG. 10(D) (iii);

FIG. 25: illustrates preferred conditions and protocols for packing SP Sepharose Fast Flow resin suitable for use in methods of the invention such as that set out in FIG. 10(D) (iii);

FIG. 26: illustrates two preferred conditions and protocols (A and B) for using SP Sepharose Fast Flow resin in a manner suitable for use in methods of the invention such as that set out in FIG. 10(D) (iii);

FIG. 27: illustrates preferred conditions and protocols for cleaning SP Sepharose Fast Flow resin: (A) after use; and (B) pre-use/regeneration as set out in FIG. 10(D) (iii);

FIG. 28: illustrates two preferred conditions and protocols (A and B) for final UF/DF membrane preparation suitable for use in methods of the invention as that set out in FIG. 10(E) (i); and FIG. 29: illustrates two preferred conditions and protocols (A and B) for UF/DF of SP Sepharose elution purified TGF-β3 solution, and final filling, that are suitable for use in methods of the invention such as that set out in FIG. 10(E) (i).

EXAMPLE 1

The inventors investigated whether or not improved methods of re-folding members of the TGF-Beta superfamily could be established. The following example is illustrative of the application of the methods of the invention to the re-folding of TGF-Beta 3.

First, a study was set up to first screen re-fold reagents (see 1.13). Reagents that were found to aid re-folding in the primary screen were then taken forward as described herein, for further optimisation to maximise yield and reduce refold timelines (see 1.14). Finally methods of purifying the refolded growth factor were investigated (1.15-1.17).

Methods employed to test the biological activity of TGF-Beta 3 are described at 1.18, These studies lead the inventors to realise that improved methods of folding members of the TGF-Beta superfamily into an active form may be established by following the method defined by the first aspect of the invention.

EXPERIMENTAL 1.1 Nucleotide Sequence

The nucleotide sequence coding for TGF-Beta 3 active fragment is as follows:

```
                                           (SEQ ID No. 1)
GCT TTG GAC ACC AAT TAC TGC TTC CGC AAC TTG GAG

GAG AAC TGC TGT GTG CGC CCC CTC TAC ATT GAC TTC

CGA CAG GAT CTG GGC TGG AAG TGG GTC CAT GAA CCT

AAG GGC TAC TAT GCC AAC TTC TGC TCA GGC CCT TGC

CCA TAC CTC CGC AGT GCA GAC ACA ACC CAC AGC ACG

GTG CTG GGA CTG TAC AAC ACT CTG AAC CCT GAA GCA

TCT GCC TCG CCT TGC TGC GTG CCC CAG GAC CTG GAG

CCC CTG ACC ATC CTG TAC TAT GTT GGG AGG ACC CCC

AAA GTG GAG CAG CTC TCC AAC ATG GTG GTG AAG TCT

TGT AAA TGT AGC
```

1.1 cDNA Generation

Total RNA from a human incisional wound (taken day 5 post-wounding) was treated with DNA-Free (Ambion) to remove any contaminating DNA. Using total RNA as a template, TGF-Beta3 cDNA was generated by Reverse Transciptase-Polymerase Chain Reaction (RT-PCR). The RT-PCR master mix was prepared from Brilliant® QRT-PCR Core Reagent Kit, 1-Step (Stratagene). One microgram of RNA was added to 50 μL of a solution containing: One-step QRT-PCR buffer, 0.2 mM dNTPs, 3.5 mM $MgCl_2$, 1 μL StrataScript reverse transcriptase, Taq Polymerse 2.5 units, 0.4 μM Sense primer (5' GAT ATA CCA TGG CTT TGG ACA CCA ATT ACT ACT GC 3') (SEQ ID No. 2), 0.4 μM Sense primer (5'-CAG CCG GAT CCG GTC GAC TCA GCT ACA TTT ACA AGA C 3') (SEQ ID No. 3). The reaction was placed in a thermal cycler (Hybaid PCR Express) and run under the following conditions: 30 min at 45° C., 10 min at 95° C., then 40 cycles of 95° C. for 30 sec, 65° C. for 1 min and 72° C. for 1 min. Final step of 72° C. for 10 min. PCR samples were nm on 2% (w/w) agarose gel to verify band size and purified using Wizard PCR Prep Kit (Promega).

1.2 Vector Cloning and Host Cell Transformation

The pET-24d vector is derived from pBR322 vector and contains a T7 promoter under LacUV5 control and a kanamycin resistant marker gene.

The TGF-Beta 3 cDNA fragments (generated in Section 1.1) were digested with 0.75 μL of Nco1 (New England Biolabs) and 0.75 μL of BamH1 (New England Biolabs) with 1×BamH1 Buffer (New England Biolabs) in a 15 μL reaction (Nuclease Free Water, Novagen) at 37° C. for 4 hours. One microliter of pET-24d plasmid (Novagen) was digested in the same manner. The digested cDNA and the large plasmid fragment were agarose gel purified and recovered using the SpinPrep Gel DNA extraction kit (Novagen).

The purified cDNA and plasmid fragments were ligated using T4 ligase kit (Novagen). The ligated cDNA/plasmid was transformed into HMS174 (DE3) (Novagen HMS174 (DE3) transformation kit). The transformants were selected by plating on Luria broth (LB) agar plates containing 50 µg/mL kanamycin (Invitrogen). Three clones were selected for restriction digest and/or expression.

1.3 Clone Screening for Product Expression

Clones were grown in shake flask cultures of half strength 'Terrific Broth' (6 g/L phytone peptone (Becton Dickinson), 12 g/L yeast extract (Becton Dickinson), 2 g/L glycerol (JT Baker), 1.16 g/L potassium phosphate monobasic (JT Baker), 6.25 g/L potassium phosphate dibasic (JT Baker), QS to 1 Litre with distilled water) and induced in exponential phase at $OD_{600}$ between 0.65 and 0.85 with 1 mM isopropyl beta-D-thiogalactopyranoside (IPTG). Post-induction samples were taken 3 hours after the addition of IPTG and analysed by sodium dodecylsulfate polyacrylamide gel electrophoresis (SDS-PAGE) for product induction and expression. Clones 1-4 pre/post induction sample aliquots and Mark 12 molecular weight standards (Invitrogen—molecular weight range 2.5-200 kDa) were run on NuPAGE® Novex 12% Bis-Tris Gel, 1.0 mm (Invitrogen) for approximately 40-50 minutes at 120 milliAmps and 200 Volts and then stained with Coomassie Blue. A protein whose size is between 6 and 14.4 kDa (i.e., TGF-Beta 3 monomer) is clearly induced in each of these cultures (see FIG. 1) with Clone 2 expressing the greatest amount of TGF-Beta 3 protein.

1.4 Frozen Cell Stock

Clones 1-4 were grown in shake flasks in half strength Terrific Broth to an $OD_{600}$ of approximately 1. and stored as glycerol stocks by the addition of glycerol to 20% (v/v). 1.2 mL of broth was aliquoted into 12×2 mL cryovials (which contained 0.3 mL of glycerol) and then stored at −70° C.

1.5 Sequence Confirmation of TGF-Beta 3 Gene

Samples of the cultures used for frozen cell stocks were taken before the addition of glycerol and used for plasmid isolation using a Qiagen MiniPrep Kit. The isolated plasmid was sequenced and verified using a T7 promoter primer (5'-TAA TAC GAC TCA CTA TAG GG-3') (SEQ ID No. 4) and a T7 terminator primer (5'-GCT AGT TAT TGC TCA GCG G-3') (SEQ ID No. 5).

1.6 Seed Culture

As Clone 2 expressed the highest amount of TGF-Beta 3 protein an ampoule of frozen stock (from Section 1.4) was recovered and inoculated into a 2 Litre baffled Erlenmeyer flask, containing 500 mL of HySoy medium (12 g/L Hy-Soy (Quest International), 24 g/L yeast extract (Becton Dickinson), 10 g/L NaCl (Sigma) and 10 g/L glycerol (Sigma) and 50 µg/mL of kanamycin. The flask was incubated with shaking at 37° C. and 200 rpm and sampled periodically to measure $OD_{550}$. When the OD of the culture reached 3.21 U/mL (after 7 hours) the cell broth was used to seed a 150 L fermenter (100 L working volume).

1.7 Fermentation

Nine hundred millilitres of cell broth (from Section 1.6) was used to inoculate a 150 L fermenter (WHE) containing 90 L of Batch Culture Media (0.6 g/L $K_2HPO_4$, 0.4 g/L $KH_2PO_4$, 1.25 g/L $NH_4SO_4$, 12 g/L HY-Soy, 24 g/L yeast extract and 10 g/L glycerol). The fermentation operating parameters were controlled as follows: temperature set point, 37° C.; pH set point, 7.0 (maintained using 4N ammonium hydroxide and 4N phosphoric acid), and; dissolved oxygen (DO) initially calibrated to 100%. The vessel head pressure was 7 psi, and the agitation and airflow were 200-400 rpm with one volume of air per volume of medium per minute (vvm or slpm), respectively. DO was maintained above 20% by adjusting the fermentation set point parameters in the following priority: Agitation (max 400 rpm), aeration (max 1.5 vvm), oxygen supplementation (max 33.3 lpm), and backpressure (max 12 psi). Foaming was controlled with Pluronic L-61 (25% v/v). When the OD of the culture reached 10 U/mL a glycerol feed (50% v/v) was initiated at a flowrate of 45 mL/min. When OD reached 40 U/mL, the cells were induced with the addition of IPTG to 0.2 mM final concentration.

1.8 Harvest

After 4 hours post-induction, the fermenter was chilled to 10° C. and the airflow and agitation were reduced to 0.3 vvm and 100 rpm respectively. Foam and pH controls were terminated and backpressure was adjusted to 3 psi. The culture was harvested by continuous centrifugation with a Westfalia CSA 8 continuous centrifuge at 10° C. The centrifuge was operated at 15,000 rpm and a flow rate of 3 litres per min and cell slurries collected.

1.9 Cell Lysis and IB Recovery

The fermentation cell paste (from Section 1.8) was diluted 1:5 with Lysis Buffer (6.1 g/L TrizmaBase (Tris), 3.7 g/L ethylenediaminetetraacetic acid(EDTA), 58.44 g/L NaCl and 10 g/L Triton X-100, pH 8.0) and re-suspended using a hand held homogenizer. The re-suspended cell paste was passed twice through a high-pressure homogenizer (parameters: pressure, 10,000 psig; flow rate, 450 mL/min; and temperature, 15° C.). The homogenised cell lysate was then centrifuged (bucket centrifuge, fixed-angle rotor) at 5,000×g for 20 minutes at 4° C. The supernatant was discarded leaving insoluble (inclusion bodies) TGF-Beta 3. The inclusion body (IB) pellet was re-suspended in Wash Buffer (6.1 g/L Tris and 3.72 g/L EDTA, pH 8.0) using a hand held homogenizer and centrifuged (5,000×g for 20 minutes at 4° C.).

1.10 Inclusion Body Solubilization

The sediment from Section 1.9 was diluted 1:10 with Solubilization Buffer (6.1 g/L Tris, 15.4 g/L DL-dithiothreitol (DTT) and 360.4 g/L urea, pH 8.0) and re-suspended using a hand held homogenizer. The suspension was covered and left stirring for 60-75 minutes, at room temperature to solubilize the inclusion bodies and reduce TGF-Beta 3 to its monomeric form. The pH of the re-suspended pellet was adjusted to pH 9.4-9.6 with NaOH/acetic acid before incubation for a second time for 60-75 minutes.

1.11 Clarification/Ultrafiltration and Diafiltration

Solubilized material from Section 1.10 was clarified, concentrated and dia-filtered in a Tangential Flow Filtration (TFF) system (Millipore). Initial clarification and concentration was achieved with a pre-conditioned clarification TFF membrane (Millipore Pellicon 1000 kDa, regenerated cellulose, screen V). The clarified TGF-Beta 3 was collected in the permeate. Switching to a Ultrafiltration/Diafiltration (UF/

DF) membrane (Millipore Pellicon 5 kDa, regenerated cellulose, screen C), the TGF-Beta 3 was then washed in 6 diavolumes of Solubilisation Buffer (6.1 g/L Tris, 15.4 g/L DTT and 360.4 g/L urea, pH 9.5).

1.12 Re-fold Screening Matrix 1

1.12.1 Methodology

TGF-Beta 3 protein content in the clarified material from Section 1.11 was quantified using the RC DC™ Protein Assay (BioRad) in conjunction with SDS-PAGE, Coomassie Blue Staining and densitometry. The TGF-Beta 3 material was diluted into a series of refold buffers (See Tables 1 and 2). 1 mL samples were taken daily over a 6-day timeline and analyzed under non-reducing conditions using SDS-PAGE. Sample aliquots and Mark 12 molecular weight standards (Invitogen—molecular weight range 2.5-200 kDa) were run on NuPAGE® Novex 12% Bis-Tris Gels, 1.0 mm (Invitrogen) for approximately 40-50 minutes at 120 milliAmps and 200 Volts. The protein samples were then electrophoretically transferred to nitrocellulose membrane (Invitrogen) using a Novex Blotting apparatus (Invitrogen). The membrane was blocked with 5% (w/v) skimmed milk powder, 1% (v/v) polyoxyethylenesorbitan monolaurate (Tween 20; Sigma) in phosphate buffered saline (PBS). The membrane was washed (PBS, 0.1% (v/v) Tween 20) and incubated for 1 hour in primary antibody (Anti-TGF-Beta 3, MAB643 (R&D systems) diluted 1:500 in PBS and 0.1 (v/v) Tween 20). Following incubation with the primary antibody, the nitrocellulose was washed in washing buffer (PBS, 1% (v/v) Tween 20). The nitrocellulose was then incubated for an additional 1 hour in the secondary antibody (Goat anti-mouse IgG conjugated with alkaline phosphatase (Abcam PO397) diluted 1:2000 with PBS, 0.1% (v/v) Tween 20). The membrane was again washed (PBS, 1% (v/v) Tween 20 before developing with Western Blue Stabilized Substrate for Alkaline Phosphatase (Promega).

The MAB 643 antibody detects correctly refolded monomeric and dimeric TGF-Beta 3 species.

1.12.2 Results

Tables 1 and 2 summarise the results obtained testing refolding of TGF-Beta 3 under 50 different experimental conditions The inventors established that the conditions described below (i.e. experimental conditions 12, 19, and 44) produced correctly refolded dimeric TGF-Beta 3:
1. 0.7 M 2-(cyclohexylamino) ethanesulfonic acid (CHES), 2 mM reduced glutathione (GSH), 0.4 mM oxidised Glutathione (GSSG), 0.12 mg/mL TGF-Beta 3, pH 9.5 at 2-8° C. (Experimental condition 12).
2. 30 mM Taurodeoxycholate, 0.7 M CHES, 2 mM GSH, 0.4 mM GSSG, 0.12 mg/mL TGF-Beta 3, pH 9.5 at 2-8° C. (Experimental condition 19).
3. 30 mM Taurodeoxycholate, 0.7 M CHES, 2 mM GSH, 2 mM GSSG, 0.12 mg/mL TGF-Beta 3, pH 9.5 at 2-8° C. (Experimental condition 44).

By way of example FIG. 2 illustrates the effectiveness of Experimental Condition 12.

TABLE 1

Re-fold Screening Matrix and Results

| Experimental Condition | Temp | Detergent | TGF-Beta 3 conc. | GSH conc. | GSSG Conc. | Presence of Correctly Re-folded dimeric TGF-Beta 3 by Western Blot (MAB643) analysis |
|---|---|---|---|---|---|---|
| 1 | 2-8° C. | 100 mM Zwittergent 3-08 | 0.12 mg/mL | 2 mM | 0.4 mM | None detected |
| 2 | 2-8° C. | 40 mM Taurocholate | 0.12 mg/mL | 2 mM | 0.4 mM | None detected |
| 3 | 2-8° C. | 40 mM Big CHAP | 0.12 mg/mL | 2 mM | 0.4 mM | None detected |
| 4 | 2-8° C. | 60 mM Hexyl glucopyranoside | 0.12 mg/mL | 2 mM | 0.4 mM | None detected |
| 5 | 2-8° C. | 0.5% (w/v) ASB-14 | 0.12 mg/mL | 2 mM | 0.4 mM | None detected |
| 6 | 2-8° C. | 0.5% (w/v) DDMAB | 0.12 mg/mL | 2 mM | 0.4 mM | None detected |
| 7 | 2-8° C. | 0.5% (w/v) CTAB | 0.12 mg/mL | 2 mM | 0.4 mM | None detected |
| 8 | 2-8° C. | 0.2% (w/v) SDS | 0.12 mg/mL | 2 mM | 0.4 mM | None detected |
| 9 | 2-8° C. | 0.1% (w/v) Dodecyl-b-D-maltoside | 0.12 mg/mL | 2 mM | 0.4 mM | None detected |
| 10 | 2-8° C. | 0.1% (w/v) Tween 20 | 0.12 mg/mL | 2 mM | 0.4 mM | None detected |
| 11 | 2-8° C. | 1M NDSB-201 | 0.12 mg/mL | 2 mM | 0.4 mM | None detected |
| 12 | 2-8° C. | 0.7M CHES | 0.12 mg/mL | 2 mM | 0.4 mM | Dimer |
| 13 | 2-8° C. | 20% (v/v) Sucrose | 0.12 mg/mL | 2 mM | 0.4 mM | None detected |
| 14 | 2-8° C. | 20% (v/v) Glycerol | 0.12 mg/mL | 2 mM | 0.4 mM | None detected |
| 15 | 2-8° C. | 20 mM Zwittergent 3-12 + 0.5M Arginine | 0.12 mg/mL | 2 mM | 0.4 mM | None detected |
| 16 | 2-8° C. | 20 mM Zwittergent 3-08 + 1M NDSB-221 | 0.12 mg/mL | 2 mM | 0.4 mM | None detected |
| 17 | 2-8° C. | 30 mM Taurodeoxycholate + 0.5M Arginine | 0.12 mg/mL | 2 mM | 0.4 mM | None detected |
| 18 | 2-8° C. | 30 mM Taurodeoxycholate + 1M NDSB-221 | 0.12 mg/mL | 2 mM | 0.4 mM | None detected |

TABLE 1-continued

Re-fold Screening Matrix and Results

| Experimental Condition | Temp | Detergent | TGF-Beta 3 conc. | GSH conc. | GSSG Conc. | Presence of Correctly Re-folded dimeric TGF-Beta 3 by Western Blot (MAB643) analysis |
|---|---|---|---|---|---|---|
| 19 | 2-8° C. | 30 mM Taurodeoxycholate + 0.7M CHES | 0.12 mg/mL | 2 mM | 0.4 mM | Dimer |
| 20 | 2-8° C. | 0.5M Arginine | 0.12 mg/mL | 2 mM | 0.4 mM | None detected |
| 21 | 2-8° C. | 40 mM Octyl-Thioglucopyranoside | 0.12 mg/mL | 2 mM | 0.4 mM | None detected |
| 22 | 2-8° C. | 60 mM Hexylglucopyranoside + 0.1% (w/v) PEG-6000 | 0.12 mg/mL | 2 mM | 0.4 mM | None detected |
| 23 | 2-8° C. | 30% (v/v) Ethanol | 0.12 mg/mL | 2 mM | 0.4 mM | None detected |
| 24 | 2-8° C. | 20% (v/v) Isopropyl Alcohol | 0.12 mg/mL | 2 mM | 0.4 mM | None detected |
| 25 | 2-8° C. | 30 mM Taurodeoxycholate | 0.12 mg/mL | 2 mM | 0.4 mM | None detected |

TABLE 2

Re-fold Screening Matrix and Results

| Experimental Condition | Temp | Detergent | TGF-Beta 3 conc. | GSH conc. | GSSG Conc. | Presence of Correctly Refolded dimeric TGF-Beta 3 by Western Blot (MAB643) analysis |
|---|---|---|---|---|---|---|
| 26 | 2-8° C. | 100 mM Zwittergent 3-08 | 0.12 mg/mL | 2 mM | 2 mM | None detected |
| 27 | 2-8° C. | 40 mM Taurocholate | 0.12 mg/mL | 2 mM | 2 mM | None detected |
| 28 | 2-8° C. | 40 mM Big CHAP | 0.12 mg/mL | 2 mM | 2 mM | None detected |
| 29 | 2-8° C. | 60 mM Hexyl glucopyranoside | 0.12 mg/mL | 2 mM | 2 mM | None detected |
| 30 | 2-8° C. | 0.5% (w/v) ASB-14 | 0.12 mg/mL | 2 mM | 2 mM | None detected |
| 31 | 2-8° C. | 0.5% (w/v) DDMAB | 0.12 mg/mL | 2 mM | 2 mM | None detected |
| 32 | 2-8° C. | 0.5% (w/v) CTAB | 0.12 mg/mL | 2 mM | 2 mM | None detected |
| 33 | 2-8° C. | 0.2% (w/v) SDS | 0.12 mg/mL | 2 mM | 2 mM | None detected |
| 34 | 2-8° C. | 0.1% (w/v) Dodecyl-b-D-maltoside | 0.12 mg/mL | 2 mM | 2 mM | None detected |
| 35 | 2-8° C. | 0.1% (w/v) Tween20 | 0.12 mg/mL | 2 mM | 2 mM | None detected |
| 36 | 2-8° C. | 1M NDSB-201 | 0.12 mg/mL | 2 mM | 2 mM | None detected |
| 37 | 2-8° C. | 0.7M CHES | 0.12 mg/mL | 2 mM | 2 mM | None detected |
| 38 | 2-8° C. | 20% (v/v) Sucrose | 0.12 mg/mL | 2 mM | 2 mM | None detected |
| 39 | 2-8° C. | 20% (v/v) Glycerol | 0.12 mg/mL | 2 mM | 2 mM | None detected |
| 40 | 2-8° C. | 20 mM Zwittergent 3-12 + 0.5M Arginine | 0.12 mg/mL | 2 mM | 2 mM | None detected |
| 41 | 2-8° C. | 20 mM Zwittergent 3-08 + 1M NDSB-221 | 0.12 mg/mL | 2 mM | 2 mM | None detected |
| 42 | 2-8° C. | 30 mM Taurodeoxycholate + 0.5M Arginine | 0.12 mg/mL | 2 mM | 2 mM | None detected |
| 43 | 2-8° C. | 30 mM Taurodeoxycholate + 1M NDSB-221 | 0.12 mg/mL | 2 mM | 2 mM | None detected |
| 44 | 2-8° C. | 30 mM Taurodeoxycholate + 0.7M CHES | 0.12 mg/mL | 2 mM | 2 mM | Dimer |
| 45 | 2-8° C. | 0.5M Arginine | 0.12 mg/mL | 2 mM | 2 mM | None detected |
| 46 | 2-8° C. | 40 mM Octyl-Thioglucopyranoside | 0.12 mg/mL | 2 mM | 2 mM | None detected |
| 47 | 2-8° C. | 60 mM Hexylglucopyranoside + 0.1% (w/v) PEG-6000 | 0.12 mg/mL | 2 mM | 2 mM | None detected |
| 48 | 2-8° C. | 30% (v/v) Ethanol | 0.12 mg/mL | 2 mM | 2 mM | None detected |
| 49 | 2-8° C. | 20% (v/v) Isopropyl Alcohol | 0.12 mg/mL | 2 mM | 2 mM | None detected |
| 50 | 2-8° C. | 30 mM Taurodeoxycholate | 0.12 mg/mL | 2 mM | 2 mM | None detected |

1.13 Refold Optimisation

The conditions from Experiment 12 (0.7 M CHES, 2 mM GSH, 0.4 mM GSSG, 0.12 mg/mL TGF-Beta 3 at pH 9.5 at 2-8° C.) resulted in particularly well-folded TGF-Beta 3. These conditions were therefore selected for further optimisation.

Parameters investigated were:
TGF-Beta 3 concentration (0.1 mg/mL, 0.25 mg/mL and 0.5 mg/mL)
pH (8.0, 9.0 and 9.5)
Temperature (2-8° C. and room temperature)
Addition of 1 M NaCl The TGF-Beta 3 material from Section 1.12 was diluted into a series of re-fold conditions (see Tables 3 and 4). 1 ml samples were taken daily over a 6-day timeline. Day 6 samples were analyzed under non-reducing conditions using SDS-PAGE and Western blotted (see Section 1.13 for methodology). Correctly re-folded TGF-Beta 3 monomer was detected by Western blot in all re-fold conditions. Correctly re-folded TGF-Beta 3 dimer was detected by Western Blot in all experiments containing 1.0 M NaCL (See FIGS. 3 and 4).

The conditions under which the greatest amount TGF-Beta 3 was re-folded into its dimeric state was experimental condition 34 (0.7 M CHES, 1 M NaCl, 2 mM GSH, 0.4 mM GSSG, 0.25 mg/mL TGF-Beta 3, pH 9.5 at 2-8° C./room temperature).

Day 0, 1, 2 and 3 samples from experimental condition 34 were run on non-reducing SDS-PAGE and Western blotted to determine the time points at which correctly refolded TGF-Beta 3 was produced. As shown in FIG. 5 the initial starting material and day 1 sample contained small amounts of correctly folded monomeric and dimeric TGF-Beta 3. There is a significant increase in the amount of correctly folded TGF-Beta 3 by day 2 and 3 of refolding.

FIG. 6 illustrates refolding achieved by prior art refolding conditions contemplated in U.S. Pat. No. 5,922,846, U.S. Pat. No. 5,650,494 and EP 0 433 225 (0.05 M Tris, 1 M NDSB-201, 20% (v/v) DMSO, 2% (w/v) CHAPS, 1 M NaCl, 1% (w/v) GSH, 0.2 mg/mL TGF-Beta 3, pH 9.3 at 2-8° C.), It can be seen that the amount of refolded TGF-Beta 3 is still increasing after 7 days treatment (contrast lanes 4 and 5 of FIG. 6) whereas, in contrast, the growth factor was fully folded after 2 days treatment when methods according to the invention are employed (compare lanes 3 and 4 of FIG. 5).

Re-folding of TGF-Beta 3 in experimental condition 34 was also monitored using Cation-Exchange (CEX) HPLC. A PolySulfoethyl-A HPLC column (200×4.6 mm, 5 μm, 1000A from PolyLC Inc.) was equilibrated with Mobile Phase A (10% (v/v) acetic acid, 30% (v/v) Isopropyl alcohol). Refold samples were acidified by mixing 1:1 with 20% acetic acid, 60% isopropyl alcohol. 100 μL of acidified re-fold sample was loaded onto the column at flow rate of 0.5 mL/min (this flow rate was used throughout the procedure). The column was washed with Mobile phase A for 5 minutes. A linear gradient was run over 10 minutes ending with a mixture of 60% Mobile Phase A and 40% Mobile Phase B (10% (v/v) acetic acid, 30% (v/v) isopropyl alcohol and 1 M NaCl). The application of this buffer was held for a further 5 minutes. A second linear gradient was applied over 10 minutes ending with 100% Mobile Phase B and maintained for 5 minutes. FIG. 7 illustrates that on Day 0 there are small amounts of correctly re-folded dimeric TGF-Beta 3 (see 7(a)) whereas by day 1 there is significant increase in concentration of correctly folded TGF-Beta 3 protein (see 7(b)). The concentration of dimeric TGF-Beta 3 on day 2 is similar to day 1, indicating that refolding is complete after 24 hours (see 7(c)). The completion of refolding after 24 hours is significantly faster than prior art techniques (see FIG. 6).

TABLE 3

Refold Optimisation Matrix and Results (Experimental Conditions 1-18)

| Experimental Condition | Temp | Detergent | NaCl Conc. (M) | TGF-Beta 3 conc. (mg/mL) | GSH conc. | pH | GSSG Conc. | Presence of Correctly Refolded TCP-Beta 3 by Western Blot (MAB643) analysis |
|---|---|---|---|---|---|---|---|---|
| 1 | 2-8° C. | 0.7M CHES | 0 | 0.1 | 2 mM | 8.5 | 0.4 mM | Monomer |
| 2 | 2-8° C. | 0.7M CHES | 1 | 0.1 | 2 mM | 8.5 | 0.4 mM | Monomer + dimer |
| 3 | 2-8° C. | 0.7M CHES | 0 | 0.25 | 2 mM | 8.5 | 0.4 mM | Monomer |
| 4 | 2-8° C. | 0.7M CHES | 1 | 0.25 | 2 mM | 8.5 | 0.4 mM | Monomer + dimer |
| 5 | 2-8° C. | 0.7M CHES | 0 | 0.5 | 2 mM | 8.5 | 0.4 mM | Monomer |
| 6 | 2-8° C. | 0.7M CHES | 1 | 0.5 | 2 mM | 8.5 | 0.4 mM | Monomer + dimer |
| 7 | 2-8° C. | 0.7M CHES | 0 | 0.1 | 2 mM | 9.5 | 0.4 mM | Monomer |
| 8 | 2-8° C. | 0.7M CHES | 1 | 0.1 | 2 mM | 9.5 | 0.4 mM | Monomer + dimer |
| 9 | 2-8° C. | 0.7M CHES | 0 | 0.25 | 2 mM | 9.5 | 0.4 mM | Monomer + dimer |
| 10 | 2-8° C. | 0.7M CHES | 1 | 0.25 | 2 mM | 9.5 | 0.4 mM | Monomer + dimer |
| 11 | 2-8° C. | 0.7M CHES | 0 | 0.5 | 2 mM | 9.5 | 0.4 mM | Monomer + dimer |
| 12 | 2-8° C. | 0.7M CHES | 1 | 0.5 | 2 mM | 9.5 | 0.4 mM | Monomer + dimer |
| 13 | RT | 0.7M CHES | 0 | 0.1 | 2 mM | 8.5 | 0.4 mM | Monomer |

TABLE 3-continued

Refold Optimisation Matrix and Results (Experimental Conditions 1-18)

| Experimental Condition | Temp | Detergent | NaCl Conc. (M) | TGF-Beta 3 conc. (mg/mL) | GSH conc. | pH | GSSG Conc. | Presence of Correctly Refolded TCP-Beta 3 by Western Blot (MAB643) analysis |
|---|---|---|---|---|---|---|---|---|
| 14 | RT | 0.7M CHES | 1 | 0.1 | 2 mM | 8.5 | 0.4 mM | Monomer + dimer |
| 15 | RT | 0.7M CHES | 0 | 0.25 | 2 mM | 8.5 | 0.4 mM | Monomer |
| 16 | RT | 0.7M CHES | 1 | 0.25 | 2 mM | 8.5 | 0.4 mM | Monomer + dimer |
| 17 | RT | 0.7M CHES | 0 | 0.5 | 2 mM | 8.5 | 0.4 mM | Monomer |
| 18 | RT | 0.7M CHES | 1 | 0.5 | 2 mM | 8.5 | 0.4 mM | Monomer + dimer |

Note:
RT = Room Temperature
2-8° C./RT = 3 days at 2-8° C. and 3 days at room temperature.

TABLE 4

Refold Optimisation Matrix and Results (Experimental Conditions 19-36)

| Experimental Condition | Temp | Detergent | NaCL Conc. (M) | TGF-Beta 3 conc. (mg/mL) | GSH conc. | pH | GSSG Conc. | Presence of Correctly Refolded TGF-Beta 3 by Western Blot (MAB643) analysis |
|---|---|---|---|---|---|---|---|---|
| 19 | RT | 0.7M CHES | 0 | 0.1 | 2 mM | 9.5 | 0.4 mM | Monomer |
| 20 | RT | 0.7M CHES | 1 | 0.1 | 2 mM | 9.5 | 0.4 mM | Non-detected |
| 21 | RT | 0.7M CHES | 0 | 0.25 | 2 mM | 9.5 | 0.4 mM | Monomer + dimer |
| 22 | RT | 0.7M CHES | 1 | 0.25 | 2 mM | 9.5 | 0.4 mM | Monomer + dimer |
| 23 | RT | 0.7M CHES | 0 | 0.5 | 2 mM | 9.5 | 0.4 mM | Monomer + dimer |
| 24 | RT | 0.7M CHES | 1 | 0.5 | 2 mM | 9.5 | 0.4 mM | Monomer + dimer |
| 25 | 2-8° C./RT | 0.7M CHES | 0 | 0.1 | 2 mM | 8.5 | 0.4 mM | Non-detected |
| 26 | 2-8° C./RT | 0.7M CHES | 1 | 0.1 | 2 mM | 8.5 | 0.4 mM | Monomer + dimer |
| 27 | 2-8° C./RT | 0.7M CHES | 0 | 0.25 | 2 mM | 8.5 | 0.4 mM | Monomer |
| 28 | 2-8° C./RT | 0.7M CHES | 1 | 0.25 | 2 mM | 8.5 | 0.4 mM | Monomer + dimer |
| 29 | 2-8° C./RT | 0.7M CHES | 0 | 0.5 | 2 mM | 8.5 | 0.4 mM | Monomer |
| 30 | 2-8° C./RT | 0.7M CHES | 1 | 0.5 | 2 mM | 8.5 | 0.4 mM | Monomer + dimer |
| 31 | 2-8° C./RT | 0.7M CHES | 0 | 0.1 | 2 mM | 9.5 | 0.4 mM | Monomer + dimer |
| 32 | 2-8° C./RT | 0.7M CHES | 1 | 0.1 | 2 mM | 9.5 | 0.4 mM | Monomer + dimer |
| 33 | 2-8° C./RT | 0.7M CHES | 0 | 0.25 | 2 mM | 9.5 | 0.4 mM | Monomer + dimer |
| 34 | 2-8° C./RT | 0.7M CHES | 1 | 0.25 | 2 mM | 9.5 | 0.4 mM | Monomer + dimer |
| 35 | 2-8° C./RT | 0.7M CHES | 0 | 0.5 | 2 mM | 9.5 | 0.4 mM | Monomer + dimer |
| 36 | 2-8° C./RT | 0.7M CHES | 1 | 0.5 | 2 mM | 9.5 | 0.4 mM | Monomer + dimer |

Note:
RT = Room Temperature
2-8° C./RT = 3 days at 2-8° C. and 3 days at room temperature.

Sections 1.14-1.16 describe experiments conducted to establish how TGF-Beta 3 refolded according to the first aspect of the invention may be purified.

1.14 Ultrafiltration/Hydrophobic Interaction Chromatography

The CHES refold solution identified as experimental condition 34 from Section 1.13 was concentrated 5 fold by ultrafiltration (the membrane was a flat-sheet Millipore Pellicon 5 kDa, 0.1 m$^2$, Regenerated Cellulose, screen). The pH of the concentrated re-fold material was then adjusted to a pH of 2.5-2.8 using glacial acetic acid before being diluted 1:1 in Dilution Buffer (2.72 g/L sodium acetate, 264.28 g/L ammonium sulfate, 100 g/L acetic acid, and 210.7 g/L arginine hydrochloride pH 3.3). A Butyl Sepharose 4 Fast Flow Column (Amersham, 16 cm Bed Height) was equilibrated with four column volumes of Buffer A (2.72 g/L sodium acetate, 132.14 g/L ammonium sulfate and 100 g/L acetic acid pH 3.3). The refold material was filtered through 0.22 µM membrane (Millipore Millipak filter) before being loaded onto the Butyl Sepharose column at a flow rate of 100 cm/hr (this flow rate was used throughout procedure). The column was then washed in Buffer A for four-column volumes. The TGF-Beta 3 proteins were eluted off the column using Buffer B (2.72 g/L sodium acetate, 100 g/L acetic acid and 300 g/L ethanol pH 3.3). The first peak, which contains TGF-Beta 3 proteins in both monomeric and dimeric forms, was pooled (see FIG. 8).

1.15 Cation Exchange Chromatography

Cation exchange chromatography was used to isolate the dimeric TGF-Beta 3 proteins from the monomeric proteins. The pooled TGF-Beta 3 fractions from Section 1.14 were diluted 5 fold in SP Load Dilution Buffer (2.72 g/L sodium acetate, 100 g/L acetic acid, 300 g/L Ethanol pH 4.0). A SP Sepharose Fast Flow Column (Amersham) was equilibrated with 4 column volumes of Buffer A (2.72 g/L sodium acetate, 100 g/L acetic acid, 300 g/L ethanol and 1.46 g/L sodium chloride pH 4.0). The diluted TGF-Beta 3 material was loaded onto SP Sepharose column at a flow rate of 169 cm/hr (this flow rate was used through out procedure). The column was then washed in Buffer B (2.72 g/L sodium Acetate, 100 g/L acetic acid, 300 g/L ethanol and 2.92 g/L sodium chloride pH 4.0) for four-column volumes. The TGF-Beta 3 proteins were eluted off the column using Buffer C (2.72 g/L sodium acetate, 100 g/L acetic acid, 300 g/L ethanol and 11.69 g/L sodium chloride pH 4.0). The first peak eluted is monomeric TGF-Beta 3 followed by the dimeric TGF-Beta 3. The fractions containing the TGF-Beta 3 dimer were pooled (see FIG. 9)

1.16 Ultrafiltration/Diafiltration

The fractions containing purified dimeric TGF-Beta 3 molecules from Section 1.15 underwent ultrafiltration/diafiltration to exchange the buffer to 20 mM acetic acid, 20% (v/v) ethanol and concentrate the sample to ~10 mg/mL (TGF-Beta 3 concentration was determined by U.V spectrometry).

1.17 Assay for Biological Activity

The cell growth inhibition assay (A Meager, 1991—Journal of immunological Methods; 141; pages 1 to 14) was used as an in vitro biological activity test for TGF-Beta molecules. The colorimetrical assay is based on the inhibitory effect of TGF-Beta molecules on the growth of Mink Lung Epithelial cells (MLEC). 50 µL of Dilution medium (Minimum Essential Medium with Glutamax I (Invitrogen) and 0.1% (w/v) bovine serum albumin (Sigma)) was added to each well of a 96 well plate. 50 µL serially diluted (5000 pg/mL to 9.75 pg/mL) of TGF-Beta 3 reference standard (National Institute of Biological Standards and Controls), 50 µL serially diluted (5000 pg/mL to 9.75 pg/mL) of TGF-Beta 3 (produced by methods disclosed in patents: U.S. Pat. No. 5,922,846, U.S. Pat. No. 5,650,494 and EP-B-0433 225) and 50 µL of serially diluted (5000 pg/mL to 9.75 pg/mL) of TGF-Beta 3 (CHES refolded growth factor purified according to section 1.17) protein were added to the plate(s). 50 µL of cell suspension containing: 1×10$^5$ MLEC cells/mL in Complete Medium (Minimum Essential Medium with Glutamax I (Invitrogen), 0.1% (w/v) bovine serum albumin (Sigma) and 10% (v/v) foetal bovine serum (Invitrogen) was added to each well. Plate(s) were incubated for 72 hours at 37° C. in 5% $CO_2$. The contents of each well were aspirated and washed three times with 200 µL phosphate buffered saline (Invitrogen). 100 µL of substrate solution (1M sodium acetate, 104 phosphatase substrate (Sigma) and 1% (v/v) Triton X-100 (Sigma)) was added to each well and incubated at 37° C. After 2 hours the reaction was quenched using 1 N sodium hydroxide. The plate(s) were read using a multichannel reader at 405 nm and a reference filter at 492 nm.

$IC_{50}$ values of the TGF-Beta 3 reference standard (NIBSC) and TGF-Beta 3 (produced by methods disclosed in patents: U.S. Pat. No. 5,922,846, U.S. Pat. No. 5,650,494 and EP-B-0433 225) were 242.33 pg/mL and 90 pg/mL respectively, which were similar to previously assayed standards. The material refolded according to the invention was found to have an $IC_{50}$ of 85.573 pg/mL, which indicates the TGF-Beta 3 refolded according to the invention, has at least an equivalent potency (biological activity) to TGF-Beta 3 produced by the prior art methods.

CONCLUSIONS

From the Refold screening matrix of the conditions described in tables 1 and 2, three conditions produced correctly re-folded dimeric TGF-Beta 3:

1. 0.7 M 2-(cyclohexylamino) ethanesulfonic acid (CHES), 2 mM reduced Glutathione (GSH), 0.4 mM oxidised Glutathione (GSSG), 0.12 mg/mL TGF-Beta 3, pH 9.5 at 2-8° C.
2. 30 mM taurodeoxycholate, 0.7 M CHES, 2 mM GSH, 0.4 mM GSSG, 0.12 mg/mL TGF-Beta 3, pH 9.5 at 2-8° C.
3. 30 mM taurodeoxycholate, 0.7 M CHES, 2 mM GSH, 2 mM GSSG, 0.12 mg/mL TGF-Beta 3, pH 9.5 at 2-8° C.

The refold experimental conditions containing CHES were further optimised to maximise yield and reduce timelines. The optimal re-fold conditions contained 0.7 M CHES, 1 M NaCl, 2 mM GSH, 0.4 mM GSSG, 0.25 mg/mL TGF-Beta 3 and pH 9.5, which completed refolding between 24-48 hours. This is significantly faster than 7 days using methods disclosed in patents: U.S. Pat. No. 5,922,846, U.S. Pat. No. 5,650,494 and EP-B-0433 225.

The optimised CHES re-fold was further purified and found to have comparable biological activity to a TGF-Beta 3 standard (NIBSC) and TGF-Beta 3 generated using the methodology disclosed in the prior art.

EXAMPLE 2

An industrial process was developed according to the second aspect of the invention.

FIG. 10 provides an overview of the process whereas FIGS. 11-29 provide further details, in the form of flow diagrams, of the individual steps described in FIG. 10.

The invention claimed is:

1. A method of forming a dimeric, biologically active transforming growth factor beta 3 comprising adding solubilized, unfolded monomeric transforming growth factor beta 3 to a solution comprising:

(i) 0.7 M 2-(cyclohexylamino)-ethanesulfonic acid (CHES);

(ii) a low molecular weight sulfhydryl/disulfide redox system comprising about 2 mM reduced glutathione and about 0.4 mM oxidized glutathione; and (iii) 1 M NaCl,
wherein the concentration of transforming growth factor beta 3 in the solution is about 0.25mg/mL and the solution is at a pH of about 9.5,
and incubating the unfolded monomeric transforming growth factor beta 3 in the solution until a dimeric biologically active transforming growth factor beta 3 is formed, wherein the forming of dimeric biologically active transforming growth factor beta 3 in the solution is completed within about 2 days.

* * * * *